US012202798B2

(12) United States Patent
Singhal et al.

(10) Patent No.: US 12,202,798 B2
(45) Date of Patent: Jan. 21, 2025

(54) ANTIMICROBIAL COMPOUNDS, COMPOSITIONS, AND ARTICLES OF MANUFACTURE FOR SELECTIVELY INHIBITING PATHOGENIC MICROBES

(71) Applicants: CFD RESEARCH CORPORATION, Huntsville, AL (US); THE BOARD OF REGENTS OF THE UNIVERSITY OF OKLAHOMA, Norman, OK (US)

(72) Inventors: Anuj Singhal, Huntsville, AL (US); Robert H. Cichewicz, Norman, OK (US); Lin Du, Norman, OK (US); JianLan You, Forest Hills, NY (US); Hanumantha Rao Paritala, Madison, AL (US); Abigail Grace Edwards, Hazel Green, AL (US)

(73) Assignees: CFD RESEARCH CORPORATION, Huntsville, AL (US); The Board of Regents of the University of Oklahoma, Norman, OK (US)

( * ) Notice: Subject to any disclaimer, the term of this patent is extended or adjusted under 35 U.S.C. 154(b) by 505 days.

(21) Appl. No.: 16/904,370

(22) Filed: Jun. 17, 2020

(65) Prior Publication Data

US 2020/0399218 A1 Dec. 24, 2020

Related U.S. Application Data

(60) Provisional application No. 62/863,027, filed on Jun. 18, 2019.

(51) Int. Cl.
| | |
|---|---|
| *C07D 209/30* | (2006.01) |
| *A01N 25/08* | (2006.01) |
| *A01N 43/38* | (2006.01) |
| *A01N 43/40* | (2006.01) |
| *A01N 43/90* | (2006.01) |
| *A01N 55/00* | (2006.01) |
| *A61K 47/54* | (2017.01) |
| *A61K 47/60* | (2017.01) |
| *C07D 401/12* | (2006.01) |
| *C07D 417/12* | (2006.01) |
| *C07D 471/04* | (2006.01) |
| *C07F 7/18* | (2006.01) |

(52) U.S. Cl.
CPC .......... *C07D 209/30* (2013.01); *A01N 25/08* (2013.01); *A01N 43/38* (2013.01); *A01N 43/40* (2013.01); *A01N 43/90* (2013.01); *A01N 55/00* (2013.01); *A61K 47/54* (2017.08); *A61K 47/545* (2017.08); *A61K 47/60* (2017.08); *C07D 401/12* (2013.01); *C07D 417/12* (2013.01); *C07D 471/04* (2013.01); *C07F 7/1804* (2013.01)

(58) Field of Classification Search
CPC .................................................. C07D 209/30
See application file for complete search history.

(56) References Cited

U.S. PATENT DOCUMENTS

| | | |
|---|---|---|
| 5,569,668 A | 10/1996 | Webster |
| 10,689,341 B2 | 10/2020 | Wang |
| 11,180,452 B2 * | 11/2021 | Singhal ................ C07D 471/04 |

FOREIGN PATENT DOCUMENTS

CN 108586310 A 9/2018

OTHER PUBLICATIONS

American Chemical Society. Chemical Abstract Service. RN 336189-99-2. First made available to the public/entered into STN: May 17, 2001. (Year: 2001).*
American Chemical Society. Chemical Abstract Service. RN 2134977-50-5. First made available to public/entered into STN: Oct. 15, 2017. (Year: 2017).*
American Chemical Society. Chemical Abstract Service. RN 2133417-83-9. Entered into STN: Oct. 10, 2017. (Year: 2017).*
Zhang, et al. "Iodine-catalysed versatile sulfenylation of indoles with thiophenols: controllable synthesis of mono-and bis-arylthioindoles" Tetrahedron, vol. 71, Issue 47, Nov. 25, 2015, pp. 8885-8891.
Prasa et al. "Metal free sulfenylation and bis-sulfenylation of indoles: persulfate mediated synthesis" Org. Biomol. Chem., 2013, 11, 8036-8040.
Saima et al. "Cooperative catalysis by bovine serum albumin-iodine towards cascade oxidative coupling-C(sp2)-H sulfenylation of indoles/hydroxyaryls with thiophenols on water" Org. Biomol. Chem., 2016, 14, 6111-3118.

(Continued)

*Primary Examiner* — John S Kenyon
(74) *Attorney, Agent, or Firm* — MASCHOFF BRENNAN

(57) ABSTRACT

A compound can have a structure of Formula A, or derivative thereof, salt thereof, or stereoisomer thereof, or having any chirality at any chiral center, or tautomer, polymorph, solvate, or combination thereof:

Formula A $$[R^2]_m \underset{Z^4}{\overset{Z^3}{\underset{\|}{\overset{Z^2}{\Big|}}}} Z^1 \underset{Z^6}{\overset{Z^5}{\Big|}} X - Y - \boxed{A} + [R^1]_n;$$

wherein ring A is a phenyl, indolyl, naphthyl, or benzothiazolyl; X is S, SO, or $SO_2$; Y is a linker or bond; Z is CH, $CR^2$, or N; $Z^1$ is C or N to form an imidazopyridine; each $Z^2$, $Z^3$, or $Z^4$ is independently CH, $CR^2$, or N; each $Z^5$ or $Z^6$ is C or CH; each $R^1$, $R^2$, and $R^3$ is independently a substituent, and at least one of $R^1$, $R^2$, or $R^3$ is a substituent other than a hydrogen; m is 0, 1, 2, 3, or 4; and n is 0 or a positive integer. The compounds can have specific substituent patterns.

20 Claims, 8 Drawing Sheets

(56) References Cited

OTHER PUBLICATIONS

Ohkado, et al. "Flavin-iodine coupled organocatalysis for the aerobic oxidative direct sulfenylation of indoles with thiols under mild conditions" Green Chem., 2018, 20, 984-988.
Khandekar, et al. "Identification, Substrate Specificity, and Inhibition of the *Streptococcus pneumoniae* β-Ketoacyl-Acyl Carrier Protein Synthase III (FabH)" The Journal of Biological Chemistry, vol. 276, No. 32, Issue of Aug. 10, pp. 30024-30030, 2001.
Williams et al. "5-Chloro-3-(phenylsulfonyl)indole-2-carboxamide: a novel, non-nucleoside inhibitor of HIV-1 reverse transcriptase" J. Med. Chem. 1993, 36, 9, 1291-1294.
Martino, et al. "Arylthioindoles, Potent Inhibitors of Tubulin Polymerization" J. Med. Chem. 2004, 47, 6120-6123.
La Regina et al "Indolylarylsulfones as HIV-1 Non-Nucleoside Reverse Transcriptase Inhibitors: New Cyclic Substituents at Indole-2-carboxamide" J. Med. Chem. 2011, 54, 6, 1587-1598.
Nair et al. "Marine Bacteria, XLVII—Psychrotolerant Bacteria from Extreme Antarctic Habitats as Producers of Rare Bis-and Trisindole Alkaloids" Planta Med 2016; 82(09/10): 910-918.

* cited by examiner

ANTIMICROBIAL COMPOUNDS, COMPOSITIONS, AND ARTICLES OF MANUFACTURE FOR SELECTIVELY INHIBITING PATHOGENIC MICROBES

CROSS-REFERENCE TO RELATED APPLICATIONS

This patent application claims priority to U.S. Provisional Application No. 62/863,027 filed Jun. 18, 2019, which provisional is incorporated herein by specific reference in its entirety.

GOVERNMENT RIGHTS

This invention was made with government support under W911NF-17-C-0076 and W911NF-17-P-0075 awarded by the U.S. Army. The government has certain rights in the invention.

BACKGROUND

Field

The present disclosure relates to compounds for use as antimicrobials. In some aspects, the compounds may selectively inhibit pathogenic microbes over commensal microbes.

Description of Related Art

Many diseases, ranging from more minor ailments, such as upper and lower respiratory tract infections, to potentially fatal infections are due to pathogenic microbes, including, for example, bacteria, viruses, and fungi. As a result, many compounds have been identified to be used in treatments against microbes. For example, chemical-based agents may be used for external treatment (e.g., on a hard surface) to prevent contamination and transmission to animals, and drugs may be used to treat an infected animal. While agents have been developed that are generally effective against various pathogens, there is increasing evidence that the use of such agents has certain limitations. Specifically, certain strains of pathogenic microbes have become increasingly resistant to one or more antimicrobials, thereby rendering the standard courses of treatment ineffective. Accordingly, higher doses of antimicrobial treatments may be required to achieve efficacy, which can result in undesirable side effects and toxicity to both animals and the environment.

Currently, the majority of antimicrobial compounds have been derived from natural products. Traditional antimicrobial compounds are mostly broad spectrum—inhibiting both pathogenic and commensal microbes. However, it may be beneficial to avoid inhibiting commensal microbes when inhibiting pathogenic microbes.

Therefore, it would be advantageous to have improved broad spectrum antimicrobial compounds, selective antimicrobial compounds that preferentially target pathogenic microbes, compositions, and corresponding articles of manufacture that include the antimicrobial compounds for use in methods of inhibiting microbial infections.

SUMMARY

In some embodiments, a method of selectively inhibiting pathogenic microbes can include: providing a compound that is functional as a selective antimicrobial having a structure of Formula 1, or derivative thereof, salt thereof, or stereoisomer thereof, or having any chirality at any chiral center, or tautomer, polymorph, solvate, or combination thereof; and contacting a pathogenic microbe with the compound such that the pathogenic microbe is selectively inhibited;

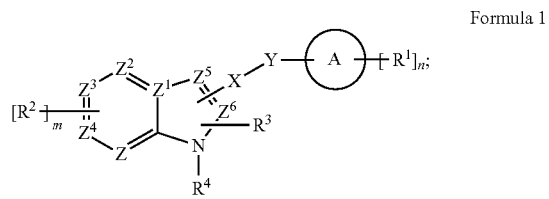

Formula 1 wherein: ring A is a cycloalkyl, heterocycloalkyl, aryl, heteroaryl, or polycycle combination thereof; X is NH, O, $CH_2$, $CH_2CH_2$, N=N, S, SO, or $SO_2$; Y is a linker or bond; Z is CH, $CR^2$, or N; $Z^1$ is C or N to form an imidazopyridine; each $Z^2$, $Z^3$, or $Z^4$ is independently CH, $CR^2$, or N; each $Z^5$ or $Z^6$ is C or CH; each $R^1$, $R^2$, $R^3$ and/or $R^4$ is independently a substituent; m is 0, 1, 2, 3, or 4; and n is zero or a positive integer. In some aspects, a composition can include the compound and a carrier having the compound. In some aspects, an article of manufacture can include: the compound and a material having the compound in a body of the material or in a surface of the material.

In some embodiments, a compound can have a structure of Formula A, or derivative thereof, salt thereof, or stereoisomer thereof, or having any chirality at any chiral center, or tautomer, polymorph, solvate, or combination thereof:

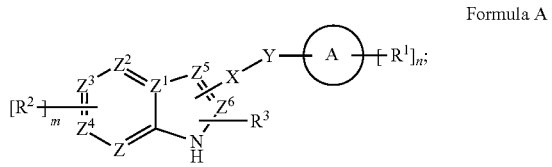

Formula A wherein ring A is a phenyl, indolyl, naphthyl, or benzothiazolyl; X is NH, O, $CH_2$, $CH_2CH_2$, N=N, S, SO, or $SO_2$; Y is a linker or bond; Z is CH, $CR^2$, or N; $Z^1$ is C or N to form an imidazopyridine; each $Z^2$, $Z^3$, or $Z^4$ is independently CH, $CR^2$, or N; each $Z^5$ or $Z^6$ is C or CH; each $R^1$, $R^2$, and $R^3$ is independently a substituent, and at least one of $R^1$, $R^2$, or $R^3$ is a substituent other than a hydrogen; m is 0, 1, 2, 3, or 4; and n is 0 or a positive integer, and: when X is S and ring A is a phenyl, $R^1$ is a substituent other than a hydrogen; when X is S and ring A is a benzothiazolyl and linked to the $Z^5$ carbon and $R^3$ is hydrogen or alkyl, $R^2$ is not only a substituent on the $Z^3$ carbon or only a hydrogen; when X is S and ring A is phenyl and linked to the $Z^5$ carbon and $R^2$ is only a substituent on the $Z^3$ carbon or hydrogen and $R^3$ is hydrogen or alkyl, $R^1$ is not a para-substituent when $R^1$ is a halogen, alkoxy, hydroxyl, or amine and $R^2$ is a halogen or alkoxy; when X is S and ring A is phenyl and linked to the $Z^5$ carbon and $R^2$ is only a halogen substituent on the $Z^3$ carbon or a hydrogen, $R^1$ is not a ortho-substituent when $R^1$ is an amine or halogen and $R^2$ is a halogen or alkoxy; when X is S and ring A is a naphthyl and linked to the $Z^5$ carbon, $R^2$ is not only a substituent on the $Z^3$ carbon or hydrogen, when X is S and ring A is phenyl and linked to the $Z^5$ carbon and $R^1$ is a para-substituent halogen, $R^3$ is not an alkyl or

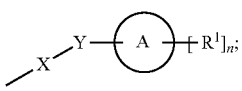

and when X is S and ring A is a phenyl and $Z^1$ is N and $R^2$ is hydrogen and $R^3$ is hydrogen, $R^1$ is not a para-substituent halogen. In some aspects, a composition can include the compound and a carrier having the compound. In some aspects, an article of manufacture can include the compound and a material having the compound.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 1A:
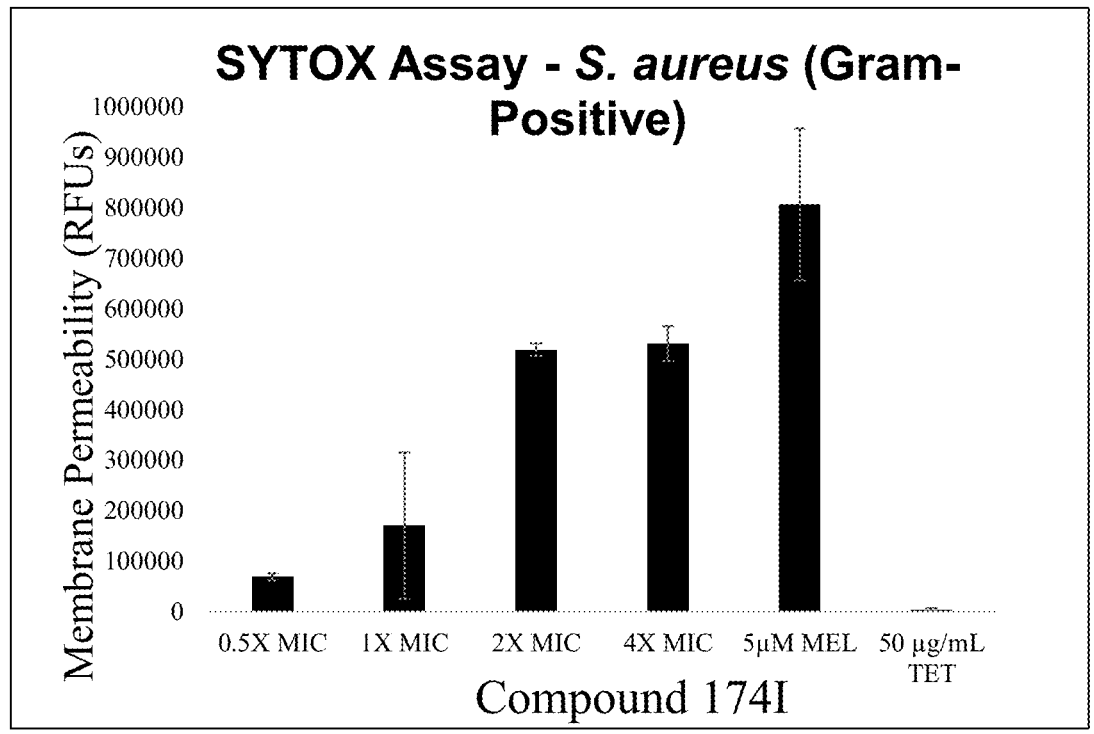
FIG. 1A includes a graph that shows the cytotoxicity of an antimicrobial Compound 174I by membrane permeability versus factors of the MIC.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology includes compounds for use as antimicrobials. In some aspects, the compounds can inhibit pathogenic microbes, such as bacteria, viruses, and fungi. The compounds can be used in methods for treating materials to be antimicrobial, and in methods of treating subjects infected with a microbe. The compounds can be prepared into various compositions, materials, or articles of manufacture for use as antimicrobials.

In some embodiments, the present technology includes compounds for use as selective antimicrobials. In some aspects, the compounds can selectively inhibit pathogenic microbes without significantly inhibiting commensal microbes. As used herein, a commensal microbe is considered to be any microbe that has commensalism, which is an association with another organism (e.g., subject), such as a human or other animals (e.g., mammals, birds, etc.) where the microbe receives a benefit for the association while the other organism may benefit and receives no harm from the association with the microbe. As used herein, a pathogenic microbe is considered to be any microbe that causes a disease state in a subject, such as a bacteria, virus, or fungus.

In some embodiments, the present invention relates to compounds that can be used as selective antimicrobials that selectively inhibit pathogenic microbes more than inhibiting commensal microbes. That is, the compounds can selectively inhibit pathogenic microbes in an amount or percent that is greater than commensal microbes are inhibited. While the commensal microbes can be inhibited by the compounds, such inhibition is significantly less than the inhibition of the pathogenic compounds. Thus, a greater degree of inhibition of the pathogenic microbes is achieved over inhibition of the commensal microbes.

In some embodiments, the selective antimicrobials can inhibit *Trichophyton rubrum* and *Trichophyton mentagrophytes*, which are the causative agents of athlete's foot and jock itch. As such, the pathogenic microbes can include *Burkholderia cenocepacia*, *Trichophyton rubrum* and *Trichophyton mentagrophytes*. However, it should be recognized that the pathogenic microbes may include other skin-disease causing microbes. The compounds have been shown to be selective antimicrobials against these pathologic microbes. It is thought that these compounds can also be selective against other pathogenic microbes for the inhibition thereof. Thus, a variety of pathogenic microbes that are fungi, bacteria, or viruses can be selectively inhibited over commensal microbes.

In some embodiments, the commensal microbes can include *Malassezia furfur*, *Micrococcus* sp., and *Staphylococcus epidermidis*. However, it should be recognized that the commensal microbes may include other microbes, such as those that live on the skin (e.g., skin commensal microbes). The compounds have been shown to have limited inhibition or effect on skin commensal microbes, such as those listed above. It is thought that these compounds can also be minimally active or have significantly reduced activity and inhibition against the skin commensal microbes, or other commensal microbes.

In some embodiments, the compounds described herein can be used as general antimicrobials. In some embodiments, the antimicrobial compounds can be used in any form and in any composition. The antimicrobial compounds can be included in pharmaceutically acceptable carriers and administered to a subject in need thereof. For example, the compounds can be included in a topical composition for use against topical pathogenic microbes, such as those that cause jock itch, athlete's foot, and others. The antimicrobial compounds can be included in various liquids, gels, pastes, emulsions, or other non-solid formats.

In some embodiments, the antimicrobials can be applied to a solid, whether particulate, porous, non-porous, or in any non-liquid, non-gel, or non-flowable format. The solids can be those that may come into contact with a skin of a subject, such as a human. The antimicrobials can be applied to a surface of a solid object, and/or be embedded, encapsulated, or otherwise included within the solid body. Some examples include fabrics, which may be used for various articles of manufacture, ranging from clothing (e.g., underwear, socks, pants, shorts, skirt, dress, shirt, blouse, jersey, hat, scarf, or other), bandages, tarps, floors, mats, carpets, towels, linens, furniture, mattress, cabinet, countertop, bathtub, sink, faucet, hot tub, toys, or the like, whether as a coating (e.g., in a paint, caulk, or coating) or within the material thereof. The antimicrobials may be generally added to baby products or children products to protect them from the pathogenic microbes. The antimicrobials may be applied to athletic products that are worn or used during a sport, such as to balls, bats, gloves, hats, uniforms, undergarments, shoes, or the like that come into contact with the skin of a subject. The antimicrobial may be applied to camping products, such as those worn or used that come into contact with the skin of a subject, such as tents, sleeping bags, walking sticks, ropes, bungee cords, or the like. Any article of manufacture can include the antimicrobial compound. Some examples that have antimicrobials include fabrics, which may be used for various articles of manufacture, ranging from clothing (e.g., underwear, socks, pants, shorts, skirt, dress, shirt, blouse, jersey, hat, scarf, or other), footwear (e.g., shoes, sandals, flip flops, boat shoes), bandages, surgical drapes, tarps, floors, mats, carpets, towels, linens, furniture, mattress, cabinet, countertop, bathtub, sink, faucet, hot tub, toys, or the like, whether as a coating (e.g., in a paint, caulk, or coating) or within the material thereof. Accordingly, the general antimicrobials can be applied to any liquid carrier or any solid member (e.g., to surface or within the material).

The antimicrobials may be generally added to baby products or children products to protect them from the pathogenic microbes while allowing the commensal microbes to be relatively unharmed (or significantly less harm). The selective antimicrobial may be applied to athletic products that are worn or used during a sport, such as to balls, bats, gloves, hats, uniforms, undergarments, shoes, or the like that come into contact with the skin of a subject. The selective antimicrobial may be applied to camping products, such as those worn or used that come into contact with the skin of a subject, such as tents, sleeping bags, walking sticks, ropes, bungee cords, or the like. Any article of manufacture can include the selective antimicrobial compound. Some examples that have selective antimicrobials include fabrics, which may be used for various articles of manufacture, ranging from clothing (e.g., underwear, socks, pants, shorts, skirt, dress, shirt, blouse, jersey, hat, scarf, or other), footwear (e.g., shoes, sandals, flip flops, boat shoes), bandages, surgical drapes, tarps, floors, mats, carpets, towels, linens, furniture, mattress, cabinet, countertop, bathtub, sink, faucet, hot tub, toys, or the like, whether as a coating (e.g., in a paint, caulk, or coating) or within the material thereof. Accordingly, the selective antimicrobials can be applied to any liquid carrier or any solid member (e.g., to surface or within the material).

In some embodiments, the antimicrobials can be used to treat or inhibit an active microbial infection or microbial colony on an object or in a liquid. That is, any antimicrobial can be applied used against microbes that are already present. However, the antimicrobials may also be used in a prophylactic therapy to provide the antimicrobial prior to there being a microbial infection or colony. Here, the antimicrobial can be administered to a person prior to being infected with the microbe in a prophylactic therapy. Also, the antimicrobial can be applied to objects so that the antimicrobial is present and functional when or if the object comes into contact with a microbe or otherwise inhibiting microbe colony formation on the object.

In some embodiments, the antimicrobials can be used as a treatment or prophylactic therapy for treating a biofilms or inhibiting or preventing formation of a biofilm. That is, the antimicrobial can be applied before, during, or after formation of a biofilm. As used herein, a "biofilm" is at least one type of microbe growing in a colony or group on a surface so as to form a film of the mirobe(s). Thus, the antimicrobials can inhibit formation or growth of biofilms.

In an aspect, the disclosure pertains to inhibitors of microbes, such as bacteria and fungi (antibacterials and antifungals) or viruses (e.g., antivirals) derived from a specific compound; pharmaceutical compositions comprising disclosed compounds and their derivatives; methods of treating growth of bacteria and/or fungi and/or viruses in or on mammals and objects.

In some embodiments, the antimicrobial can include a structure under Formulae 1, 1A, 1B, 1C, or 1D, or derivative, salt thereof, or stereoisomer thereof, or having any chirality at any chiral center, or tautomer, polymorph, solvate, or combination thereof, as presented herein:

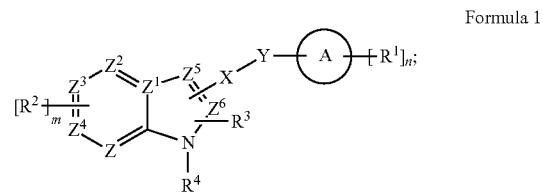

Formula 1

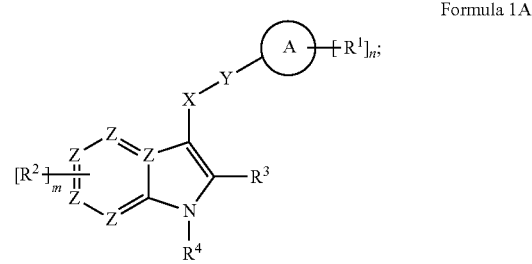

Formula 1A

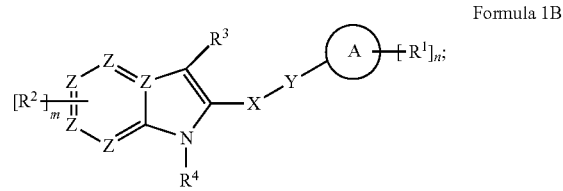

Formula 1B

Formula 1C

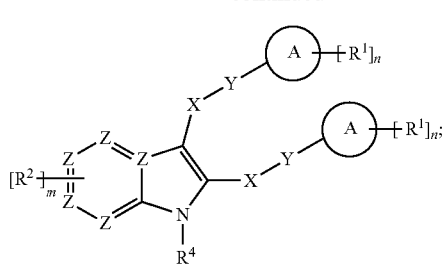

Formula 1D

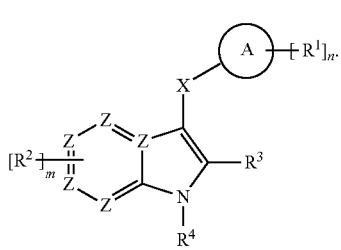

In some embodiments, the structure of Formulae 1-1D can include ring A being any aromatic ring, polyaromatic, or ring structure having at least one aromatic ring, any ring thereof with or without hetero atoms. Formula 1 can include any substituent R group for $R^1$, $R^2$, $R^3$ and/or $R^4$, such as those described herein or otherwise known. Each R group may be independently selected, and each $R^1$, $R^2$, $R^3$ and/or $R^4$ on the same ring may be independently selected from each other. As shown, "n" can be any zero or integer depending on the structure of ring A. The "m" may be 0, 1, 2, 3, or 4. X is NH, O, $CH_2$, $CH_2CH_2$, N=N, S, SO, or $SO_2$. The Y is a bond (e.g., no atom for Y) or a linker. Each Z is independently CH or N.

In some embodiments, ring A is a cycloalkyl, heterocycloalkyl, aryl, heteroaryl, or polycycle combination thereof; X is NH, O, $CH_2$, $CH_2CH_2$, N=N, S, SO, or $SO_2$; Y is a linker or bond; Z is CH, $CR^2$, or N; $Z^1$ is C or N to form an imidazopyridine; each $Z^2$, $Z^3$, or $Z^4$ is independently CH, $CR^2$, or N; each $Z^5$ or $Z^6$ is C or CH; each $R^1$, $R^2$, $R^3$ and/or $R^4$ is independently a substituent; m is 0, 1, 2, 3, or 4; and n is zero or a positive integer. In some aspects, a composition can include the compound and a carrier having the compound. In some aspects, an article of manufacture can include: the compound and a material having the compound in a body of the material or in a surface of the material.

In some embodiments of Formulae 1-1D, ring A is a cycloalkyl, heterocycloalkyl, aryl, heteroaryl, or polycycle combination thereof; X is S, SO, or $SO_2$; Y is a linker or bond; Z is CH, $CR^2$, or N; $Z^1$ is C or N to form an imidazopyridine; each $Z^2$, $Z^3$, or $Z^4$ is independently CH, $CR^2$, or N; each $Z^5$ or $Z^6$ is C or CH; each $R^1$, $R^2$, $R^3$ and/or $R^4$ is independently a substituent; m is 0, 1, 2, 3, or 4; and n is zero or a positive integer. In some aspects, ring A is an aromatic ring, polyaromatic, or ring structure having at least one aromatic ring, any ring thereof with or without hetero atoms.

In some embodiments, the compounds that can be general antimicrobials can include derivatives of 4-(1H-indol-3-yl-sulfanyl)phenol, and some derivatives can be selective antimicrobials. In some aspects, 4-(1H-indol-3-yl-sulfanyl)phenol and its close derivatives (e.g., para $R^1$ hydroxyl substituent) are specifically omitted as a general antimicrobial, or as a selective antimicrobial in some instances. In some aspects, the omitted compounds have an $R^1$ hydroxyl in the para position. In some aspects, the omitted compounds have an $R^1$ hydroxyl in any position. In some aspects, the included compounds include a $R^2$, $R^3$, or $R^4$ substituent other than hydrogen with $R^1$ is a hydroxyl, such as the para position.

In some embodiments, the antimicrobial can include a structure under Formulae 2, 2A, 2B, 2C, or 2D, or derivative, salt thereof, or stereoisomer thereof, or having any chirality at any chiral center, or tautomer, polymorph, solvate, or combination thereof, as presented herein:

Formula 2

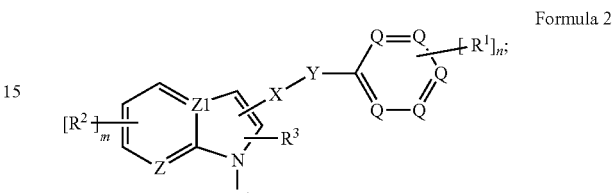

Formula 2A

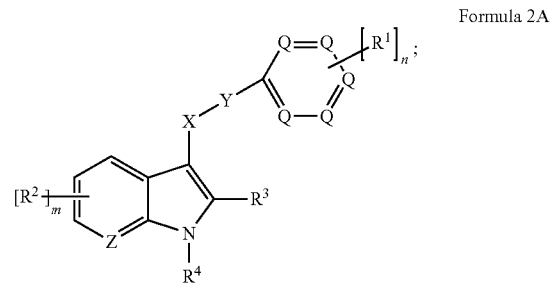

Formula 2B

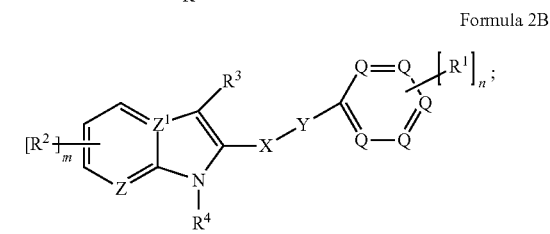

Formula 2C

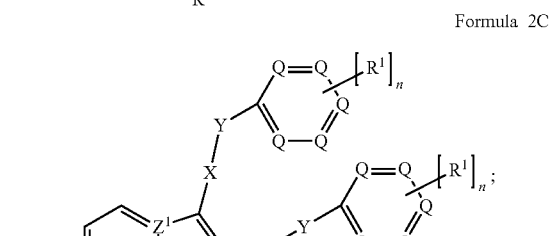

Formula 2D

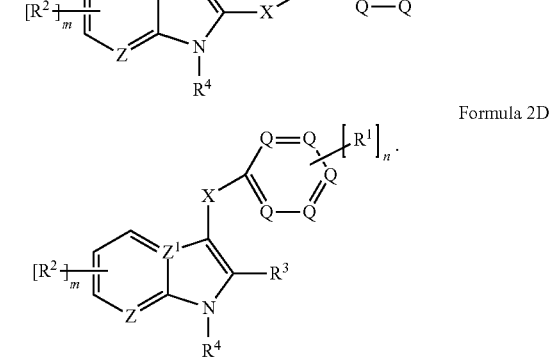

In Formulae 2, 2A, 2B, 2C, or 2D, or any other formula, each Q is independently a CH, $CR^1$, N, or $NH^+$. When $NH^+$, there can be a counter anion so as to form a salt.

In some embodiments, the antimicrobial has a structure of Formula A2, A2A, A2B, A2C, or A2D, or derivative, salt thereof, or stereoisomer thereof, or having any chirality at any chiral center, or tautomer, polymorph, solvate, or combination thereof;

Formula A2

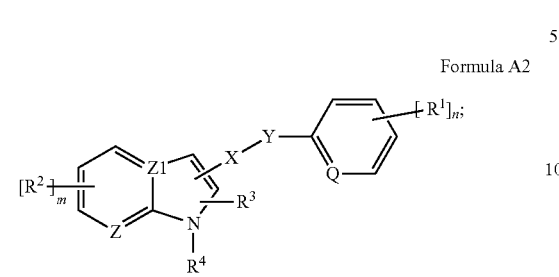

Formula A2A

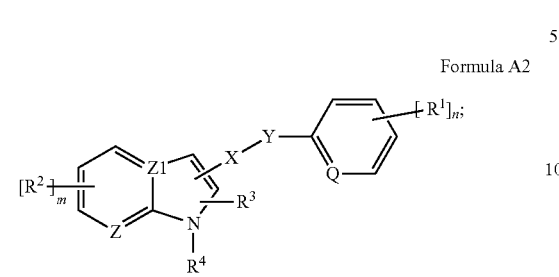

Formula A2B

Formula A2C

Formula A2D

In the Formula A2-A2D, Q is independently a CH, CR$^1$, N, or NH$^+$.

In some embodiments, the antimicrobial has a structure of Formula B2, B2A, B2B, B2C, or B2D, or derivative, salt thereof, or stereoisomer thereof, or having any chirality at any chiral center, or tautomer, polymorph, solvate, or combination thereof;

Formula B2

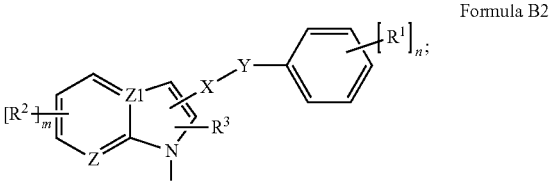

Formula B2A

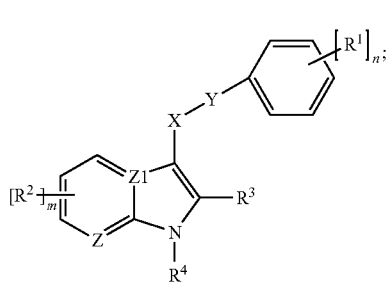

Formula B2B

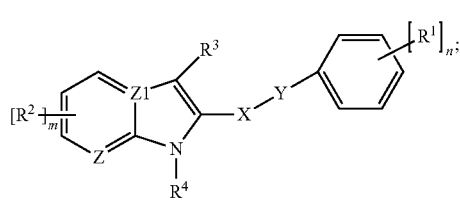

Formula B2C

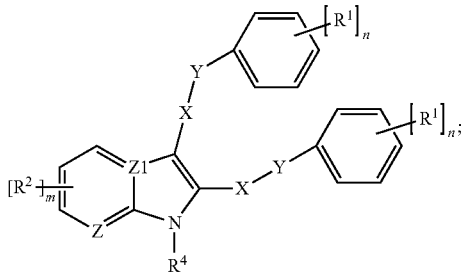

Formula B2D

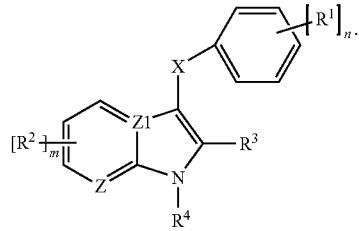

In some embodiments, the antimicrobial has a structure of Formula C2, C2A, C2B, C2C, or C2D, or derivative, salt thereof, or stereoisomer thereof, or having any chirality at any chiral center, or tautomer, polymorph, solvate, or combination thereof;

Formula C2

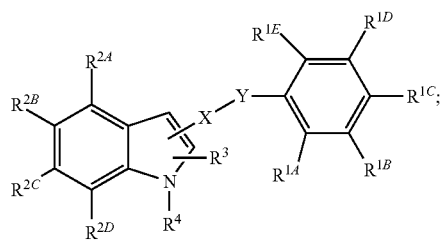

Formula C2A

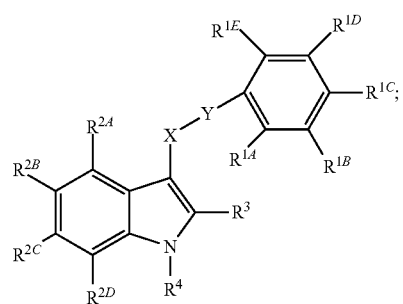

Formula C2B

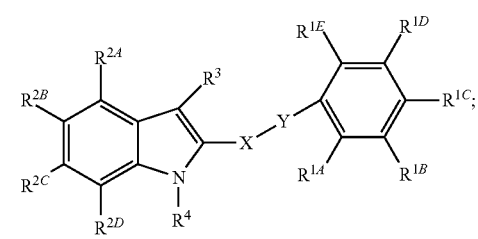

Formula C2C

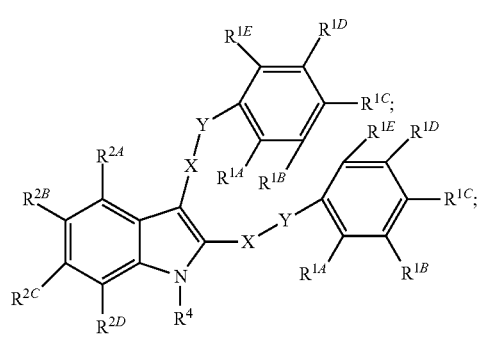

Formula C2D

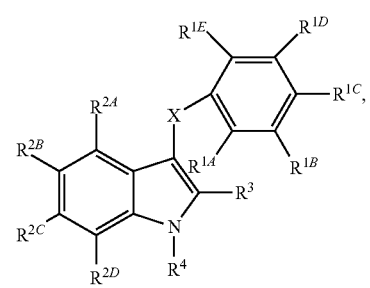

In the different Formulae, each $R^{1A}$, $R^{1B}$, $R^{1C}$, $R^{1D}$, and/or $R^{1E}$ is independently a substituent; and each $R^{2A}$, $R^{2B}$, $R^{2C}$, and/or $R^{2D}$ is independently a substituent. In some aspects, In the different Formulae, each $R^{1A}$, $R^{1B}$, $R^{1C}$, $R^{1D}$, and/or $R^{1E}$ is independently a substituent as defined for $R^1$. In some aspects, each $R^{2A}$, $R^{2B}$, $R^{2C}$, and/or $R^{2D}$ is independently a substituent as defined for $R^2$. In some aspects, $R^3$ is as defined herein. In some aspects, $R^4$ is as defined herein.

In some embodiments, Formula C2D includes: $R^{1A}$ being F, $CF_3$, $CH_3$, carboxy (e.g., carboxylic acid C(O)OH), or methanol; $R^{1C}$ being H or F; $R^{2B}$ being Br, $CH_3$, or $CF_3$; $R^3$ being methyl, ethyl, isopropyl, or tert-butyl; $R^4$ is H; the rest of the R groups are H; and X is NH, O, $CH_2$, $CH_2CH_2$, N═N, S, SO, or $SO_2$.

In some embodiments, the antimicrobial can include a structure under Formula 3, 3A, 3B, 3C, or 3D, or derivative, salt thereof, or stereoisomer thereof, or having any chirality at any chiral center, or tautomer, polymorph, solvate, or combination thereof, as presented herein:

Formula 3

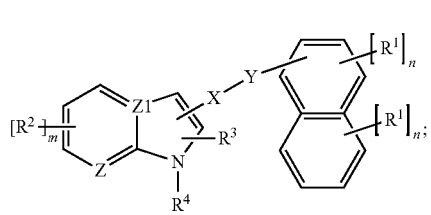

Formula 3A

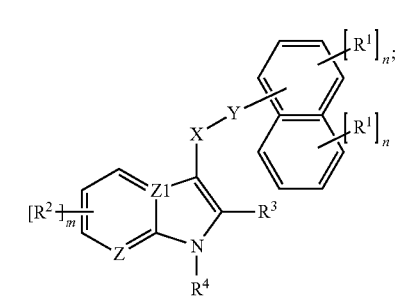

Formula 3B

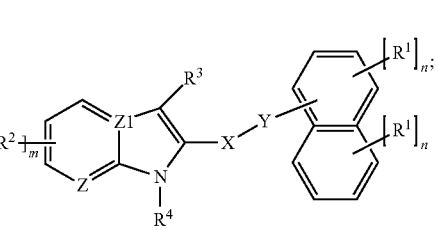

Formula 3C

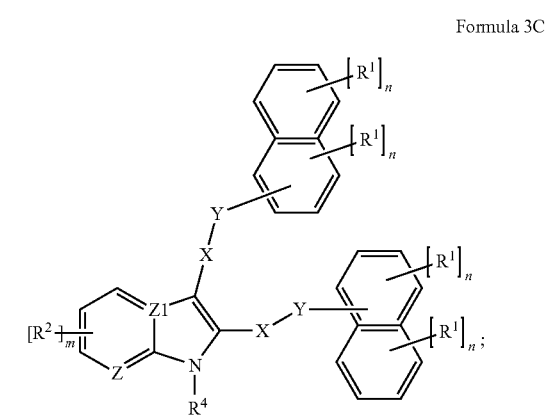

-continued

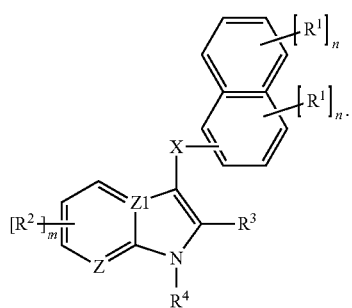
Formula 3D

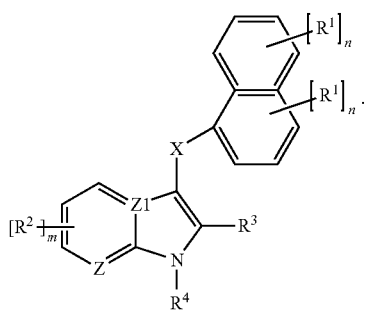
Formula A3D

In some embodiments, the antimicrobial can include a structure under Formula A3, A3A, A3B, A3C, or A3D, or derivative, salt thereof, or stereoisomer thereof, or having any chirality at any chiral center, or tautomer, polymorph, solvate, or combination thereof, as presented herein:

In some embodiments, the antimicrobial can include a structure under Formula 4, 4A, 4B, 4C, or 4D, or derivative, salt thereof, or stereoisomer thereof, or having any chirality at any chiral center, or tautomer, polymorph, solvate, or combination thereof, as presented herein.

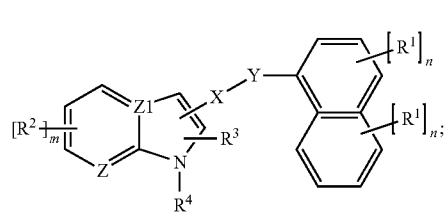
Formula A3

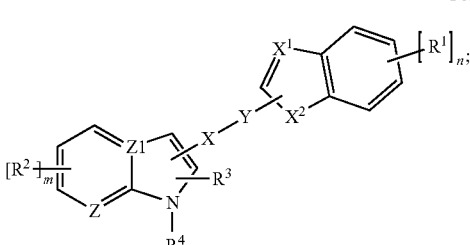
Formula 4

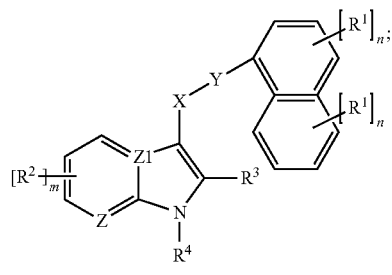
Formula A3A

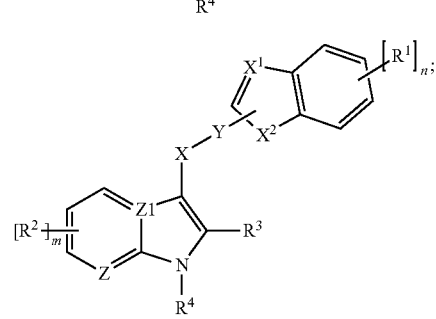
Formula 4A

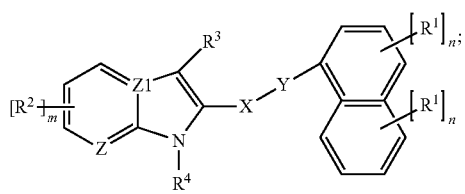
Formula A3B

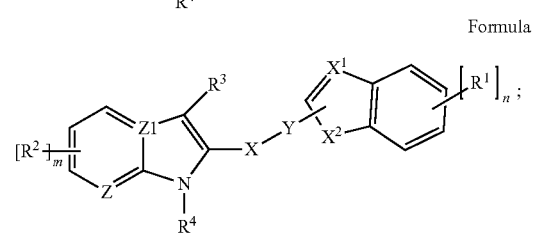
Formula 4B

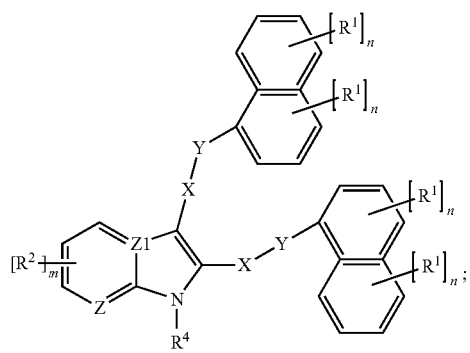
Formula A3C

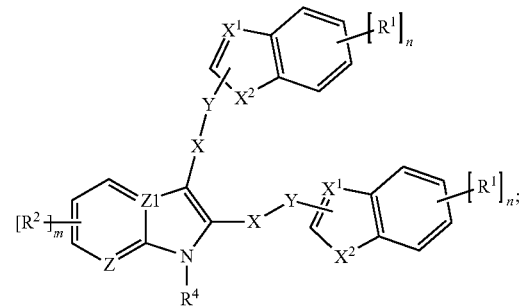
Formula 4C

Formula 4D

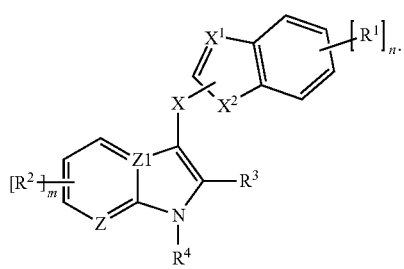

Formula A4D

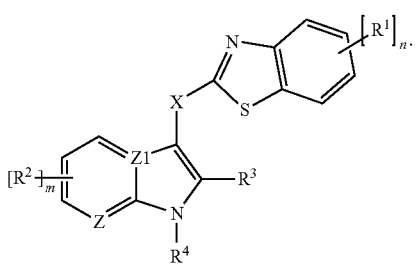

In the Formulae 4-4D, $X^1$ is CH or N; and $X^2$ is CH, $CH_2$ or S.

In some embodiments, the antimicrobial can include a structure under Formula A4, A4A, A4B, A4C, or A4D, or derivative, salt thereof, or stereoisomer thereof, or having any chirality at any chiral center, or tautomer, polymorph, solvate, or combination thereof, as presented herein.

In some embodiments, the antimicrobial has a structure of Formula B4, B4A, B4B, B4C, or B4D, or derivative, salt thereof, or stereoisomer thereof, or having any chirality at any chiral center, or tautomer, polymorph, solvate, or combination thereof, as presented herein.

Formula A4

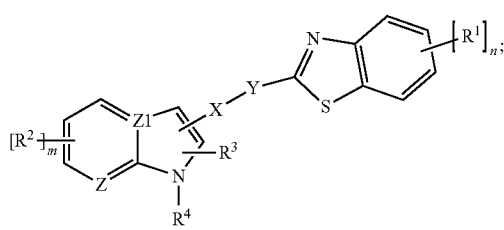

Formula B4

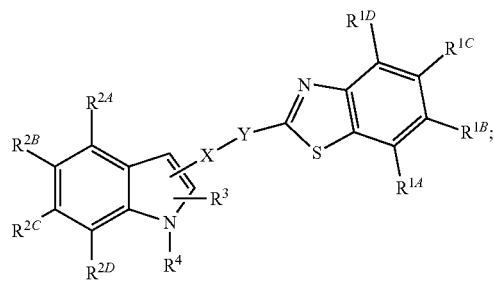

Formula A4A

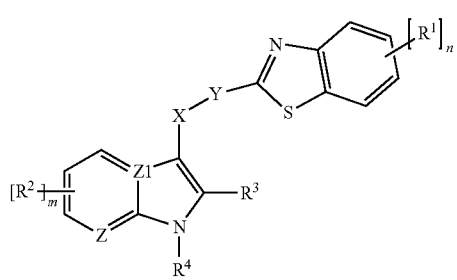

Formula A4B

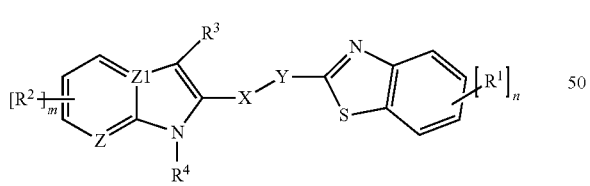

Formula B4A

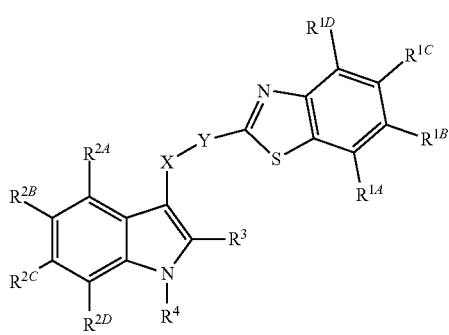

Formula A4C

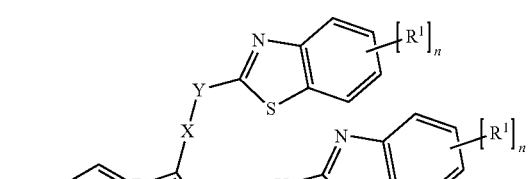

Formula B4B

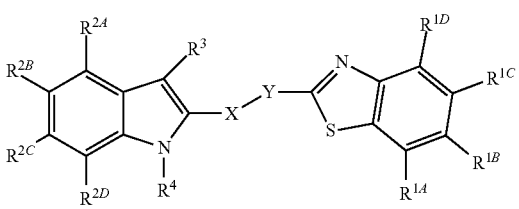

Formula B4C

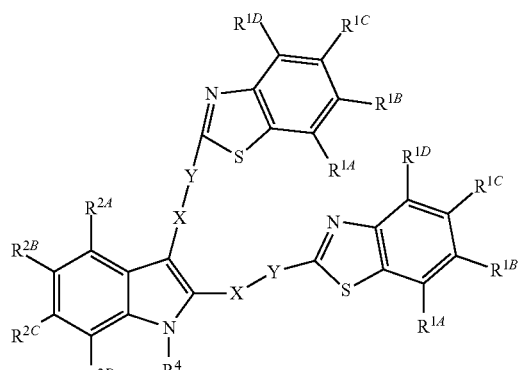

Formula B4D

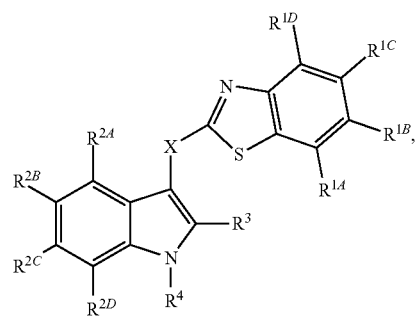

In the formulae, each $R^{1A}$, $R^{1B}$, $R^{1C}$, and/or $R^{1D}$ is independently a substituent; and each $R^{2A}$, $R^{2B}$, $R^{2C}$, and/or $R^{2D}$ is independently a substituent.

In some embodiments, each $R^{1A}$, $R^{1B}$, $R^{1C}$, $R^{1D}$ and/or $R^{1E}$ is independently as defined for $R^1$.

In some embodiments, each $R^{2A}$, $R^{2B}$, $R^{2C}$, and/or $R^{2D}$ is independently as defined for $R^2$.

In some embodiments, $R^3$ can be a hydrogen, $C_1$-$C_6$ alkyl, or a substituted $C_1$-$C_6$ alkylamine. In some embodiments, $R^3$ can be a hydrogen, $C_1$-$C_5$ alkyl, or a substituted $C_1$-$C_5$ alkylamine. In some embodiments, $R^3$ can be a hydrogen, $C_1$-$C_4$ alkyl, or a substituted $C_1$-$C_4$ alkylamine. In some embodiments, $R^3$ can be a hydrogen, $C_1$-$C_3$ alkyl, or a substituted $C_1$-$C_3$ alkylamine.

In some embodiments, the antimicrobial can include a structure under Formula 5, 5A, 5B, 5C, or 5D, or derivative, salt thereof, or stereoisomer thereof, or having any chirality at any chiral center, or tautomer, polymorph, solvate, or combination thereof, as presented herein.

Formula 5

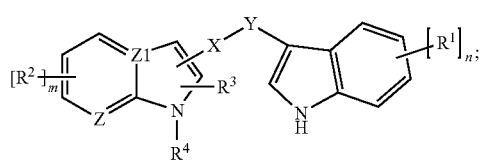

Formula 5A

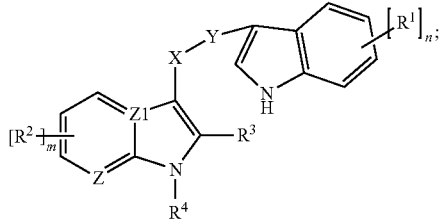

Formula 5B

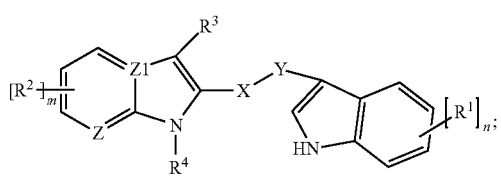

Formula 5C

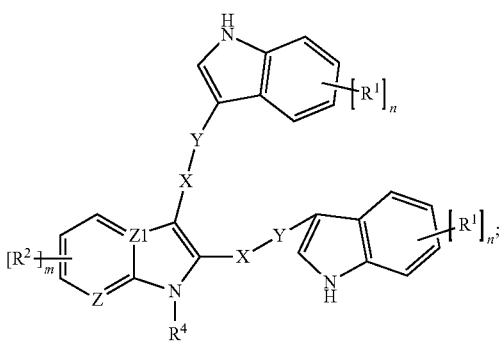

Formula 5D

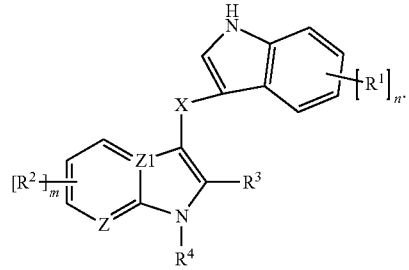

In some embodiments, the antimicrobial can include a structure under Formula 6, 6A, 6B, 6C, or 6D, or derivative, salt thereof, or stereoisomer thereof, or having any chirality at any chiral center, or tautomer, polymorph, solvate, or combination thereof, as presented herein.

Formula 6

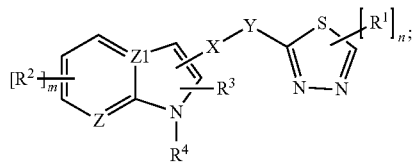

Formula 6A

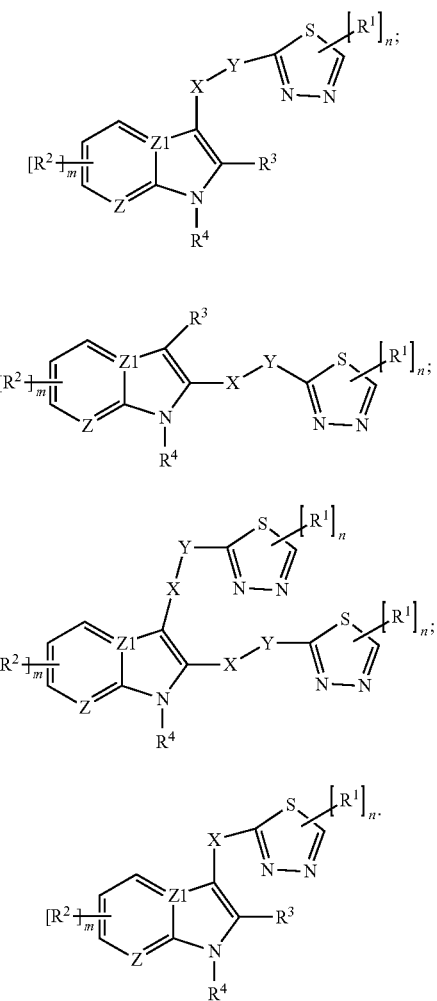

Formula 6B

Formula 6C

Formula 6D

In some embodiments, the antimicrobial can include a structure under Formula 7, 7A, 7B, 7C, or 7D, or derivative, salt thereof, or stereoisomer thereof, or having any chirality at any chiral center, or tautomer, polymorph, solvate, or combination thereof, as presented herein.

Formula 7

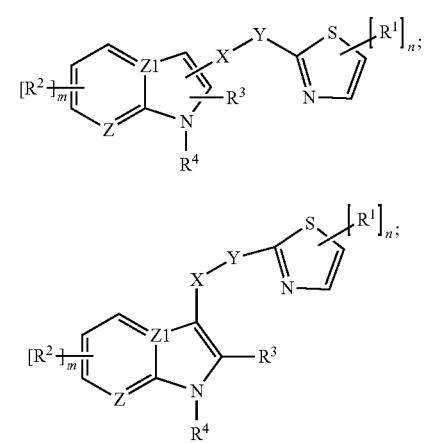

Formula 7A

Formula 7B

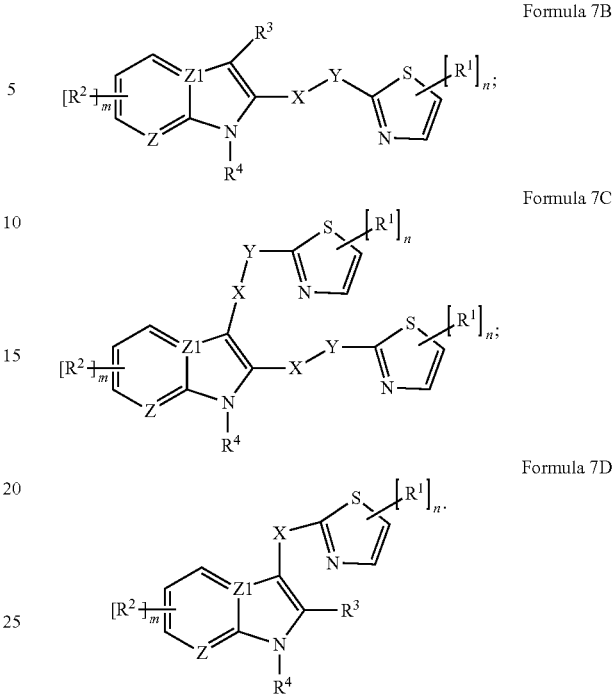

Formula 7C

Formula 7D

In some embodiments, Y is a linker or a bond between the X atom and the ring A, or the ring structure shown in the formulae, the linker can have a linker chain having one or more chain atoms. In some embodiments, Y is a bond (e.g., sometimes considered "nothing" as there is no atom for Y). Accordingly, each Y can be removed from each formulae herein when Y is a bond or Y does not include any atoms. When Y is one chain atom or more than one chain atom, there may be a R substituent on one or more of the chain atoms. The linker can be a hydrocarbon chain with or without one or more hetero atoms, such as O, N, or S. The linker may include straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, derivatives thereof, substituted or unsubstituted, or combinations. In some aspects, the linker can include $C_1$-$C_{24}$ alkyl, $C_2$-$C_{24}$ alkenyl, $C_2$-$C_{24}$ alkynyl, $C_6$-$C_{20}$ aryl, $C_7$-$C_{24}$ alkaryl, $C_7$-$C_{24}$ aralkyl, amino, mono- and di-(alkyl)-substituted amino, mono- and di-(aryl)-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, phosphino, any with or without hetero atoms, derivatives thereof, and combinations thereof. In some aspects, the linker can include $C_1$-$C_{12}$ alkyl, $C_2$-$C_{12}$ alkenyl, $C_2$-$C_{12}$ alkynyl, any with or without hetero atoms, derivatives thereof, and combinations thereof. In some aspects, the linker can include $C_1$-$C_{10}$ alkyl, $C_2$-$C_{10}$ alkenyl, $C_2$-$C_{10}$ alkynyl, any with or without hetero atoms, derivatives thereof, and combinations thereof. In some aspects, the linker can include $C_1$-$C_8$ alkyl, $C_2$-$C_8$ alkenyl, $C_2$-$C_8$ alkynyl, any with or without hetero atoms, derivatives thereof, and combinations thereof. In some aspects, the linker can include $C_1$-$C_6$ alkyl, $C_2$-$C_6$ alkenyl, $C_2$-$C_6$ alkynyl, any with or without hetero atoms, derivatives thereof, and combinations thereof. In some aspects, the linker can include $C_1$-$C_4$ alkyl, $C_2$-$C_4$ alkenyl, $C_2$-$C_4$ alkynyl, any with or without hetero atoms, derivatives thereof, and combinations thereof. In some aspects, the linker can include $C_1$-$C_3$ alkyl any with or without hetero atoms, derivatives thereof, and combinations thereof. In some aspects, the linker can include $C_1$-$C_2$ alkyl any with or without hetero atoms, derivatives thereof, and combinations thereof.

In the formulae, ring A can be any ring structure with a single ring or two or more fused rings, which can be cycloaliphatic, hetero cycloaliphatic, aryl, hetero aryl, polyaryl, poly hetero aryl, polycycloalkylaryl, or combinations thereof with 4, 5, 6, 7, 8, 9, 10, 11, or more 12 atoms. When including hetero atoms, they can be C, O, N, S, or P and depend on the number of bonds therewith, and any ring A can include 1, 2, 3, 4, 5, 6 or more hetero atoms. Ring A can be substituted with one or more $R^1$ groups. The number of $R^1$ group substituents for ring A are determined by the number of atoms in the ring when single rings being n−1 (not fused rings) where n is the number of ring atoms. Each R group substituent on a ring can be different from the others.

In the formulae, the Q and/or Z ring atoms can be carbon (C) or a hetero atom, such as O, N, S, P or other with appropriate hydrogens or R group substituents. As noted, when carbon, the Q and/or Z ring atom may or may not have a substituent, which can be on any atom of the respective ring, such as on the Q and/or Z ring atom.

In some embodiments, $X^2$ can be a C (e.g., $CH_2$) or O or N (e.g., NH) or S or P (e.g., PH), with the appropriate hydrogen atoms. The $X^1$ can be a C (e.g., CH) or N or P, with the appropriate hydrogen atoms.

In the formulae, the R substituent groups, such as $R^1$, $R^2$, $R^3$, and $R^4$ can be any possible substituent or one substituent or a combination of the substituents recited herein. Depending on the ring atom of conjugation, there may or may not be an R substituent group. These R substituent groups can be on one or more ring atoms or linker atom (e.g., Y). As such, each atom of a ring or linker atom may include a substituent as shown in Formula A. Each R substituent for a specific atom can be any possible substituent or one substituent or a combination of substituents.

In some embodiments, each $R^1$, $R^2$, $R^3$ and/or $R^4$ is independently hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, polymers, conjugation moieties, derivatives thereof, substituted or unsubstituted, or combinations thereof as well as other well-known chemical substituents, and combinations thereof. When on a hetero atom, the $R^1$, $R^2$, $R^3$, or $R^4$ may be devoid of a substituent, and thereby nothing but electrons, such as electron pairs etc.

In some embodiments, each $R^1$, $R^2$, $R^3$ and/or $R^4$ is independently hydrogen, alkyl, alkenyl, alkynyl, aryl, alkaryl, aralkyl, halo, hydroxyl, sulfhydryl, alkoxy, alkenyloxy, alkynyloxy, aryloxy, acyl, alkylcarbonyl, arylcarbonyl, acyloxy, alkoxycarbonyl, aryloxycarbonyl, ether, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-(alkyl)-substituted amino, mono- and di-(aryl)-substituted amino, alkylamido, arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, phosphine, polymers, conjugation moieties, any with or without hetero atoms, any including straight chains, any including branches, and any including rings, derivatives thereof, and combinations thereof.

In some embodiments, each $R^1$, $R^2$, $R^3$ and/or $R^4$ is independently any one or more of the substituents selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, $C_1$-$C_{24}$ polyether (e.g., PEG), halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halogenated $C_1$-$C_{24}$ alkyls, halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), di-substituted arylcarbamoyl (—(CO)—NH-aryl)$_2$, thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-substituted arylthiocarbamoyl (—(CS)—NH-aryl), di-substituted arylthiocarbamoyl (—(CS)—NH-aryl)$_2$, carbamido (—NH—(CO)—$NH_2$),), mono-($C_1$-$C_{24}$ alkyl)-substituted carbamido (—NH—(CO)—NH($C_1$-$C_{24}$ alkyl)), di-($C_1$-$C_{24}$ alkyl)-substituted carbamido (—NH—(CO)—N($C_1$-$C_{24}$ alkyl)$_2$), mono-substituted aryl carbamido (—NH—(CO)—NH-aryl), di-substituted aryl carbamido (—NH—(CO)—N-(aryl)$_2$) cyano(—C≡N), isocyano (—N$^+$≡C$^-$), cyanato (—O—C≡N), isocyanato (—O—N$^+$≡C$^-$), thiocyanato (—S—C≡N), isothiocyanato (—S—N$^+$≡C$^-$), azido (—N=N$^+$=N$^-$), formyl (—(CO)—H), thioformyl (—(CS)—H), amino (—$NH_2$), mono- and di-($C_1$-$C_{24}$ alkyl)-substituted amino, mono- and di-($C_6$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, $C_1$-$C_{24}$ alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfonic acid (—$SO_2$—OH), sulfonato (—$SO_2$—O$^-$), $C_1$-$C_{24}$ alkylsulfanyl (—S-alkyl; also termed "alkylthio"), $C_5$-$C_{20}$ arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O—)), phospho (—$PO_2$), phosphine (—$PH_2$), diazirine (N=N), alkyl diazirine, polymers, conjugation moieties, any with or without hetero atoms (e.g., N, O, P, S, or other) where the hetero atoms can be substituted (e.g., hetero atom substituted for carbon in chain or ring) for the carbons or in addition thereto (e.g., hetero atom added to carbon chain or ring) swapped, any including straight chains, any including branches, and any inducing rings, derivatives thereof, and combinations thereof.

In some embodiments, each $R^1$, $R^2$, $R^3$ and/or $R^4$ is independently a substituent as described herein that further includes an end group that is functional as a conjugation moiety. That is, any substituent recited herein can further include a conjugation moiety at a terminal end, which conjugation moiety can be used to link the antimicrobial to a substrate or any material. The examples of conjugation moieties can include alkoxy silanes (e.g., triethoxy silane), biotin, carboxylic acid, amine, halide, or any other common reactive chemical moiety that can be used to form a covalent bond with a substrate. In some aspects, only $R^2$ or $R^3$ may be a substituent as described herein that further includes an end group that is functional to function as a conjugation moiety. In some aspects, $R^4$ is hydrogen.

In some embodiments, each $R^1$, $R^2$, $R^3$ and/or $R^4$ is independently a substituent as described herein that further includes a polymer, such as a water soluble polymer, such as a poly ether (e.g., PEG). The polymer can be attached to the ring structure, within the substituent, or as a terminal portion of the substituent. For example, the antimicrobials can be PEGylated for improved water solubility. In some aspects, only $R^2$ or $R^3$ may be a substituent as described herein that further includes a polymer. In some aspects, $R^4$ is hydrogen.

In some embodiments, ring A includes: at least one phenyl group, pyrimidyl group, triazinyl group, or pyridyl group; a thiazole fused to a phenyl group, pyrimidyl group, triazinyl group, or pyridyl group; indolyl group; naphthyl group; a benzothiazole group; thiadiazol group; thiazole group; or at least two fused rings including a phenyl group, pyrimidyl group, triazinyl group, and/or pyridyl group.

In some embodiments, Y is a bond or an aliphatic linker.

In some embodiments, each $R^1$, $R^2$, $R^3$ and/or $R^4$ is independently H, F, Br, Cl, I, methyl, ethyl, propyl, butyl, pentyl, hexyl, heptyl, octyl, isopropyl, tert-butyl, methoxy (e.g., ether), ethoxy, propoxy, butoxy, pentoxy, hexoxy, heptoxy, octoxy, acetyl (i.e., CH3C=O), propionyl, butyryl, acetamide (i.e., acetylamino), propionamide, butyramide, pentanamide, hexanamide, heptanamide, octanamide, fluoromethyl, bifluoromethyl, trifluoromethyl, fluoromethoxy, bifluoromethoxy, trifluoromethoxy, methyl ester, ethyl ester, propyl ester, butyl ester, pentyl ester, hexyl ester, heptyl ester, octyl ester, methylsulfanyl (i.e., thiomethyl), ethylsulfanyl, propylsulfanyl, butylsulfanyl, pentylsulfanyl, hexylsulfanyl, heptylsulfanyl, or octylsulfanyl.

In some embodiments, each $R^1$ is independently H, hydroxyl, Br, Cl, F, carboxyl, alkyl ester, alkyoxy, or combination thereof; each $R^2$ is independently H, OH, Br, Cl, F, carboxyl, alkyl ester, alkyoxy, nitrogen dioxide, or combination thereof; $R^3$ is independently H, alkyl, alkyl ester, or combinations thereof or $R^3$ is

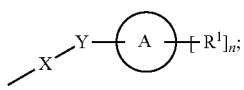

and $R^4$ is independently H or alkyl.

In some embodiments, each $R^1$ is independently H, hydroxyl, halogen (e.g., Br, Cl, F), carboxyl, alkyl ester, alkyoxy, amino, nitro, halogenated alkyl (e.g., $CF_3$), or combination thereof.

In some embodiments, each $R^1$ is independently H, OH, Br, Cl, F, —COOH, —COOCH$_3$, —OCH$_3$, halogenated alkyl (e.g., $CF_3$), amino, nitro, or combination thereof.

In some embodiments, each $R^2$ is independently H, OH, Br, Cl, F, carboxyl, alkyl ester, alkyoxy, halogenated alkyl (e.g., $CF_3$), amino, nitro, or combination thereof.

In some embodiments, each $R^2$ is independently H, OH, Br, Cl, F, —COOH, —COOCH$_3$, —OCH$_3$, NO$_2$, halogenated alkyl (e.g., $CF_3$), amino, nitro, or combination thereof.

In some embodiments, $R^3$ is independently H, alkyl, alkyl ester, halogenated alkyl, or combinations thereof.

In some embodiments, $R^3$ is independently H, methyl, ethyl, propyl, butyl, —COOCH$_3$, $CF_3$, or combination thereof.

In some embodiments, $R^4$ is independently H or alkyl.

In some embodiments, $R^4$ is independently H, methyl, ethyl, propyl, or butyl.

In some embodiments, X is NH, O, CH$_2$, CH$_2$CH$_2$, N=N, S, SO, or SO$_2$.

In some embodiments, X is a variable other than S.

In some embodiments, at least one Q is a NH$^+$, and the compound is a salt.

In some embodiments, wherein the salt includes a negative counter ion associated with the Q when a NH$^+$.

In some embodiments, wherein the salt includes a CH$_3$COO$^-$.

In some embodiments, wherein each $R^1$, $R^2$, $R^3$ and/or $R^4$ is independently selected from hydrogen, halogen, cyano, hydroxyl, —NO$_2$, —NH$_2$, —SF$_5$, —O(C$_1$-C$_6$ alkyl), —S(C$_1$-C$_6$ alkyl), C$_1$-C$_6$ haloalkyl, and C$_1$-C$^6$ hydroxyalkyl, or combination thereof.

In some embodiments, each $R^1$, $R^2$, $R^3$ and/or $R^4$ independently can include a diazirine group, such as an alkyl diazirine. An example is 3-isopropyl-3-methyl-3H-diazirine.

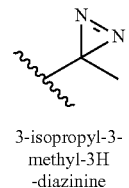

3-isopropyl-3-
methyl-3H
-diazinine

In some embodiments, $R^2$ or $R^3$ includes a terminal alkoxy silane group. The alkoxy silane can be a di-alkoxy silane or tri-alkoxy silane. For example, the alkoxy silane can be triethoxy silane. An example of the triethoxy silane-containing substituent is provided as

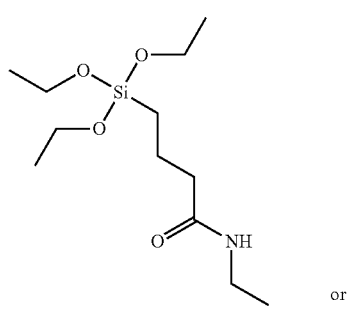

or

-continued

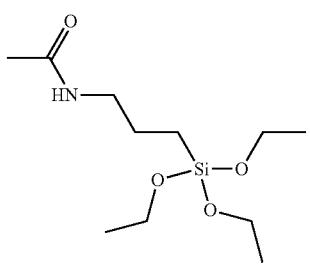

or

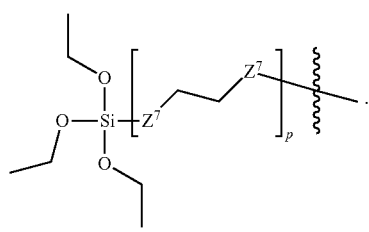

$Z^7 = CH_2$ or O
p = integer

In some embodiments, the antimicrobials can include (showing the Compound Number, e.g., 156I, referenced to the table below):

| Compound structure | Compound ID |
|---|---|
| 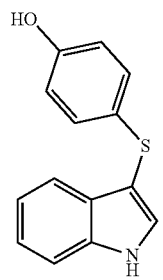<br>4-((1H-indol-3-yl)thio)phenol | 156I |
| 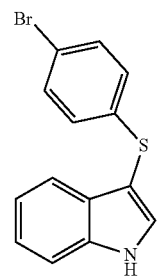<br>3-((4-bromo-phenyl)thio)-1H-indole | 156K |

| Compound structure | Compound ID |
|---|---|
| 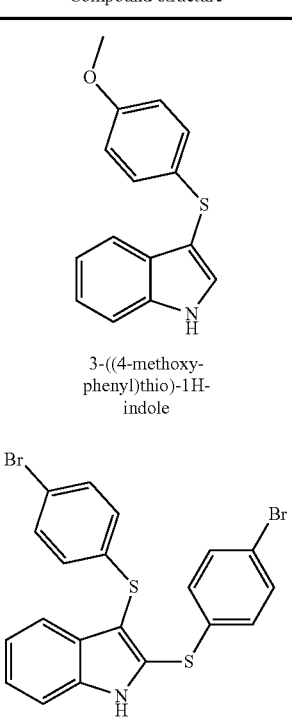<br>3-((4-methoxy-phenyl)thio)-1H-indole | 156O |
| 2,3-bis((4-bromophenyl)thio)-1H-indole | 156P |
| 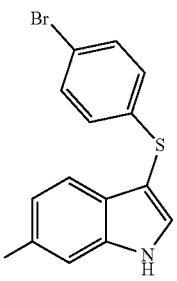<br>3-((4-bromophenyl)thio)-6-fluoro-1H-indole | 172A |
| 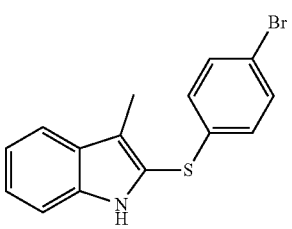<br>2-((4-bromophenyl)thio)-3-methyl-1H-indole | 172B |

| Compound structure | Compound ID |
|---|---|
| 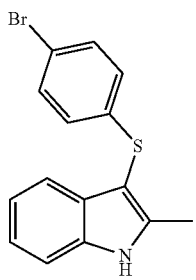<br>3-((4-bromophenyl)thio)-2-methyl-1H-indole | 172C |
| 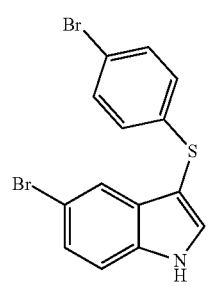<br>5-bromo-3-((4-bromophenyl)thio)-1H-indole | 172D |
| 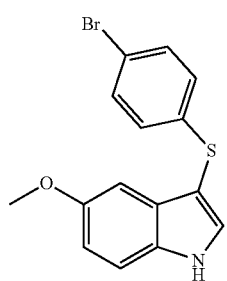<br>3-((4-bromophenyl)thio)-5-methoxy-1H-indole | 172E |
| 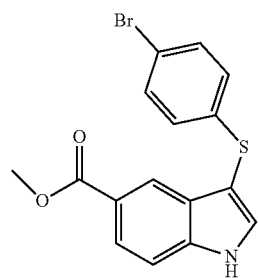<br>methyl 3-((4-bromophenyl)thio)-1H-indole-5-carboxylate | 172G |

| Compound structure | Compound ID |
|---|---|
| 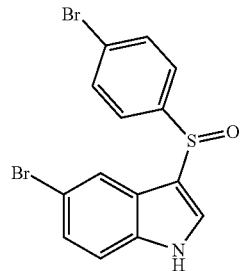<br>5-bromo-3-((4-bromophenyl)sulfinyl)-1H-indole | 172I |
| 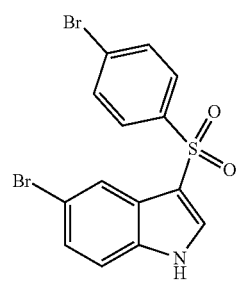<br>5-bromo-3-((4-bromophenyl)sulfonyl)-1H-indole | 172J |
| 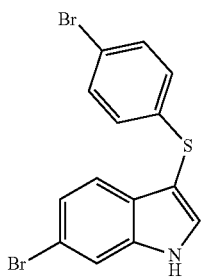<br>6-bromo-3-((4-bromophenyl)thio)-1H-indole | 174A |
| 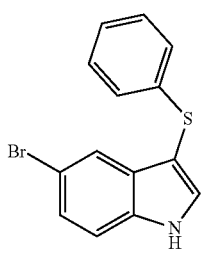<br>5-bromo-3-(phenylthio)-1H-indole | 174AA |

| Compound structure | Compound ID |
|---|---|
| 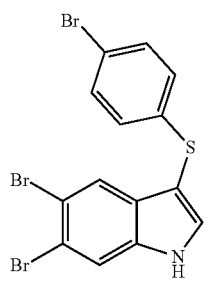 5,6-dibromo-3-((4-bromophenyl)thio)-1H-indole | 174AB |
| 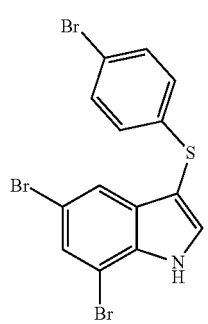 5,7-dibromo-3-((4-bromophenyl)thio)-1H-indole | 174AC |
| 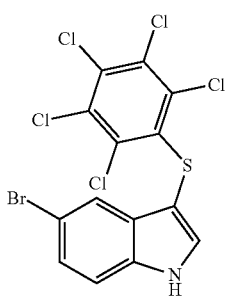 5-bromo-3-((perchloro-phenyl)thio)-1H-indole | 174AD |
| 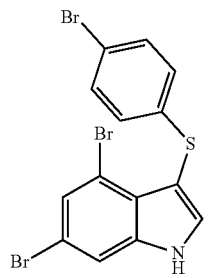 4,6-dibromo-3-((4-bromophenyl)thio)-1H-indole | 174AE |

| Compound structure | Compound ID |
|---|---|
| 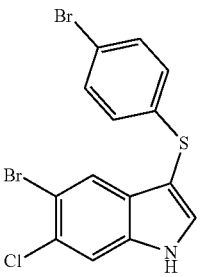 5-bromo-3-((4-bromophenyl)thio)-6-chloro-1H-indole | 174AF |
| 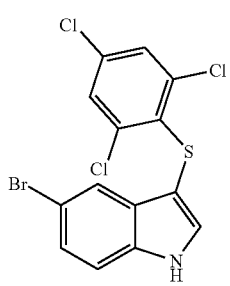 5-bromo-3-((2,4,6-trichlorophenyl)thio)-1H-indole | 174AG |
| 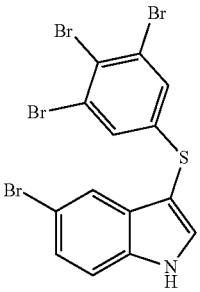 5-bromo-3-((3,4,5-tribromophenyl)thio)-1H-indole | 174AH |
| 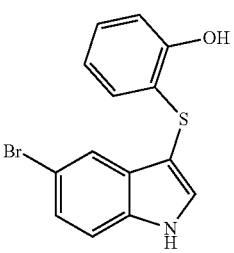 2-((5-bromo-1H-indol-3-yl)thio)phenol | 174AI |

TABLE -continued

| Compound structure | Compound ID |
|---|---|
| 5-bromo-3-((2-chlorophenyl)thio)-1H-indole | 174AJ |
| 3-((2-aminophenyl)thio)-2-methyl-1H-indol-5-ol | 174AK |
| 3-((1H-indol-3-yl)thio)-5-bromo-1H-indole | 174AL |
| 3-((4-bromophenyl)thio)imidazo[1,2-a]pyridine | 174AN |
| 3-((2-hydroxyphenyl)thio)-2-methyl-1H-indol-5-ol | 174AO |
| 3-((2-hydroxyphenyl)thio)-1H-indol-5-ol | 174AP |
| 2-((5-methoxy-1H-indol-3-yl)thio)phenol | 174AQ |
| 3-((2-bromophenyl)thio)-1H-indol-5-ol | 174AR |
| 3-((2-bromophenyl)thio)-5-methoxy-1H-indole | 174AS |

-continued

| Compound structure | Compound ID |
|---|---|
| 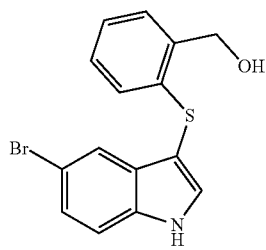<br>(2-((5-bromo-1H-indol-3-yl)thio)phenyl)methanol | 174AT |
| 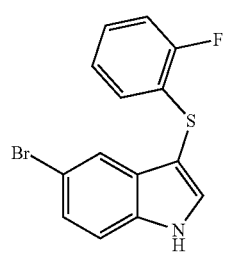<br>5-bromo-3-((2-fluorophenyl)thio)-1H-indole | 174AU |
| 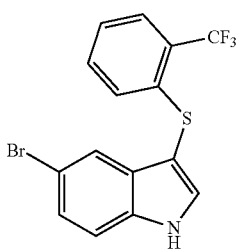<br>5-bromo-3-((2-(trifluoromethyl)phenyl)thio)-1H-indole | 174AV |
| 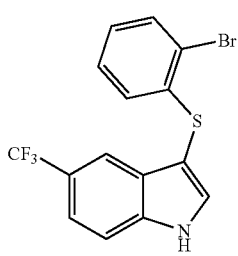<br>3-((2-bromophenyl)thio)-5-(trifluoromethyl)-1H-indole | 174AX |

-continued

| Compound structure | Compound ID |
|---|---|
| 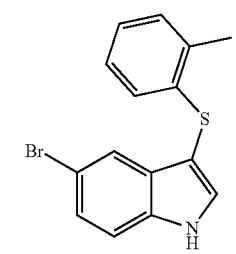<br>5-bromo-3-(o-tolylthio)-1H-indole | 174AY |
| 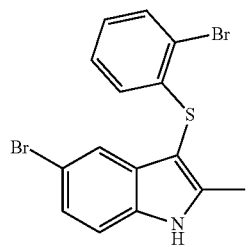<br>5-bromo-3-((2-bromophenyl)thio)-2-methyl-1H-indole | 174AZ |
| 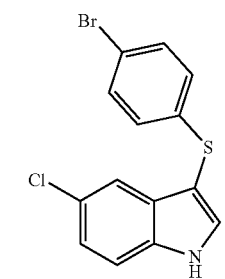<br>3-((4-bromophenyl)thio)-5-chloro-1H-indole | 174C |
| 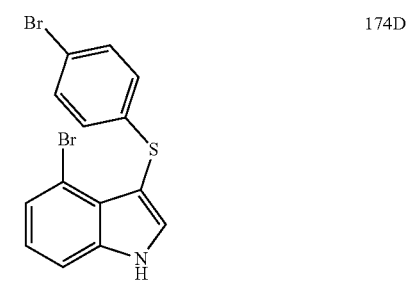<br>4-bromo-3-((4-bromophenyl)thio)-1H-indole | 174D |

| Compound structure | Compound ID |
|---|---|
| 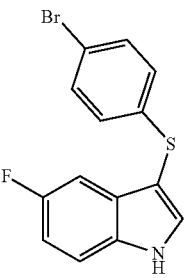<br>3-((4-bromophenyl)thio)-5-fluoro-1H-indole | 174E |
| 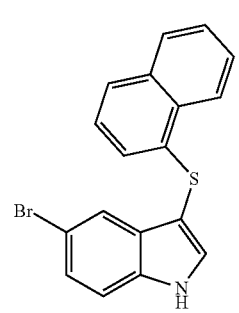<br>5-bromo-3-(naphthalen-1-ylthio)-1H-indole | 174G |
| 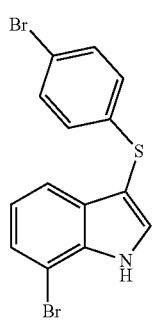<br>7-bromo-3-((4-bromophenyl)thio)-1H-indole | 174H |
| 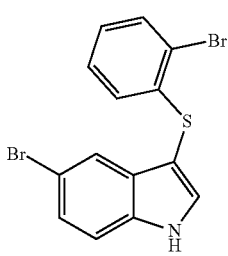<br>5-bromo-3-((2-bromophenyl)thio)-1H-indole | 174I |

| Compound structure | Compound ID |
|---|---|
| 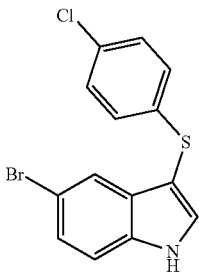<br>5-bromo-3-((4-chlorophenyl)thio)-1H-indole | 174J |
| 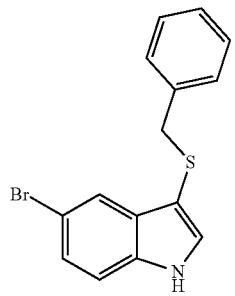<br>3-(benzylthio)-5-bromo-1H-indole | 174K |
| 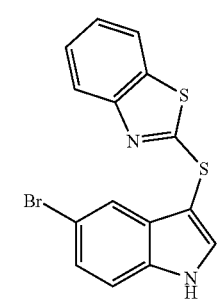<br>2-((5-bromo-1H-indol-3-yl)thio)benzo[d]thiazole | 174L |
| 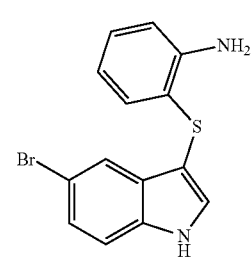<br>2-((5-bromo-1H-indol-3-yl)thio)aniline | 174M |

| Compound structure | Compound ID |
|---|---|
| 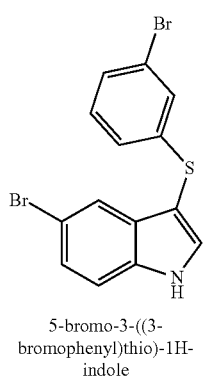 [SMILES: Brc1cccc(Sc2c[nH]c3ccc(Br)cc23)c1] 5-bromo-3-((3-bromophenyl)thio)-1H-indole | 174N |
| 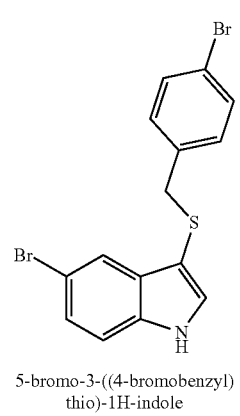 [SMILES: Brc1ccc(CSc2c[nH]c3ccc(Br)cc23)cc1] 5-bromo-3-((4-bromobenzyl)thio)-1H-indole | 174O |
| 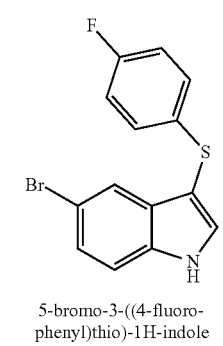 [SMILES: Fc1ccc(Sc2c[nH]c3ccc(Br)cc23)cc1] 5-bromo-3-((4-fluorophenyl)thio)-1H-indole | 174P |
| 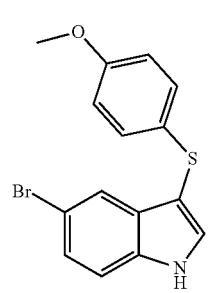 5-bromo-3-((4-methoxyphenyl)thio)-1H-indole | 174Q |
| Compound structure | Compound ID |
|---|---|
| 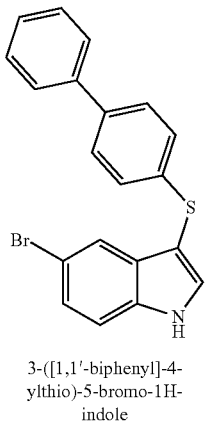 [SMILES: Brc1ccc2[nH]cc(Sc3ccc(-c4ccccc4)cc3)c2c1] 3-([1,1'-biphenyl]-4-ylthio)-5-bromo-1H-indole | 174R |
| 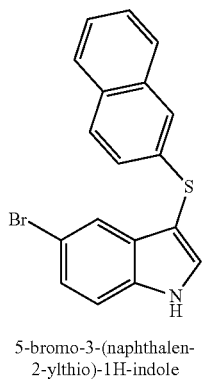 [SMILES: Brc1ccc2[nH]cc(Sc3ccc4ccccc4c3)c2c1] 5-bromo-3-(naphthalen-2-ylthio)-1H-indole | 174S |
| 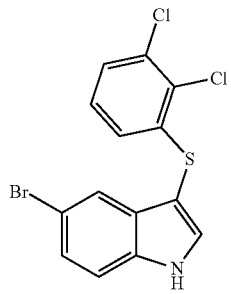 5-bromo-3-((2,3-dichlorophenyl)thio)-1H-indole | 174T |
| 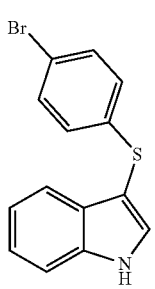 3-((4-bromophenyl)thio)-1H-indole | 174U |

| Compound structure | Compound ID |
|---|---|
| 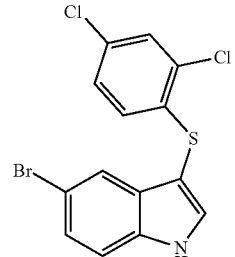 5-bromo-3-((2,4-dichloro-phenyl)thio)-1H-indole | 174V |
| 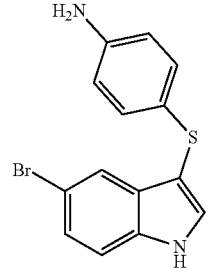 5-bromo-3-((3,4-dichlorophenyl)thio)-1H-indole | 174W |
| 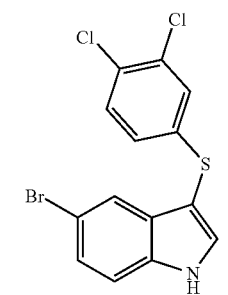 5-bromo-2-((5-bromo-1H-indol-3-yl)thio)aniline | 174X |
| 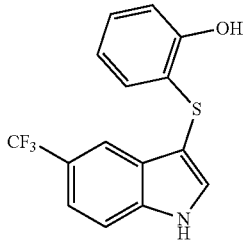 3-((5-bromo-1H-indol-3-yl)thio)aniline | 174Y |
| 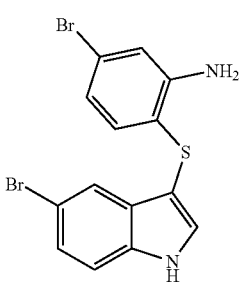 4-((5-bromo-1H-indol-3-yl)thio)aniline | 174Z |
| 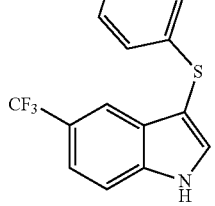 2-((5-(trifluoromethyl)-1H-indol-3-yl)thio)phenol | 177A |
| 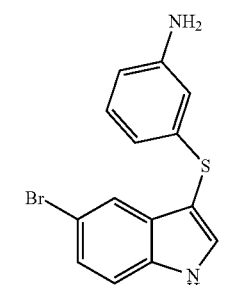 4-((5-(trifluoromethyl)-1H-indol-3-yl)thio)phenol | 177B |
| 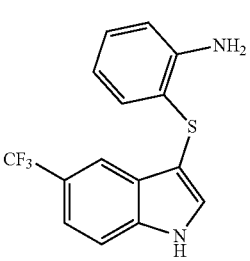 2-((5-(trifluoromethyl)-1H-indol-3-yl)thio)aniline | 177C |

| Compound structure | Compound ID |
|---|---|
| 3-((2-fluorophenyl)thio)-5-(trifluoromethyl)-1H-indole | 177D |
| 3-((2-bromophenyl)thio)-5-fluoro-1H-indole | 177E |
| 5-(trifluoromethyl)-3-((2-(trifluoromethyl)phenyl)thio)-1H-indole | 177F |
| 3-((2-ethylphenyl)thio)-5-(trifluoromethyl)-1H-indole | 177G |
| (5-bromo-3-((2-bromophenyl)thio)-1H-indol-2-yl)methanol | 177H |
| (3-((2-ethylphenyl)thio)-5-(trifluoromethyl)-1H-indol-2-yl)methanol | 177I |
| 3-(phenylthio)-1H-indole | 156L |
| 3-(pyridin-2-ylthio)-1H-indole | 156M |

| Compound structure | Compound ID |
|---|---|
| 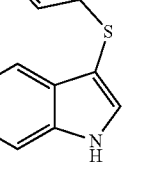 2-((1H-indol-3-yl)thio)benzoic acid | 156N |
| 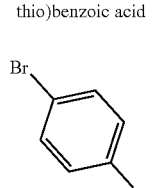 3-((4-bromophenyl)thio)-1H-pyrrolo[2,3-b]pyridine | 172F |
|  3-((4-bromophenyl)thio)-1-methyl-1H-indole | 174B |
| 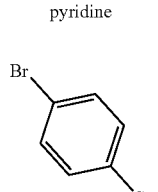 ethyl 3-((4-bromophenyl)thio)-1H-indole-2-carboxylate | 172H |

| Compound structure | Compound ID |
|---|---|
| 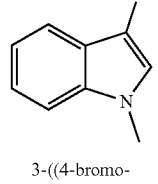 N-((3-((4-hydroxyphenyl)thio)-1H-indol-5-yl)methyl)-4-(triethoxysilyl)butanamide | 156SI |
| 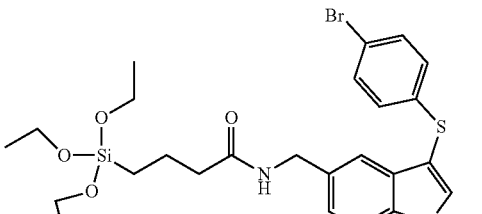 3-((2-aminophenyl)thio)-5-bromo-N-(3-(triethoxysilyl)propyl)-1H-indole-2-carboxamide | 174SI |

In some embodiments, the antimicrobial methods include using a compound that is selected from the group of (structure name (Compound No.)): 3-((4-bromophenyl)thio)-6-fluoro-1H-indole (172A); 2-((4-bromophenyl)thio)-3-methyl-1H-indole (172B); methyl 3-((4-bromophenyl)thio)-1H-indole-5-carboxylate (172G); 5-bromo-3-((4-bromophenyl)sulfinyl)-1H-indole (172I); 5-bromo-3-((4-bromophenyl)sulfonyl)-1H-indole (172J); 6-bromo-3-((4-bromophenyl)thio)-1H-indole (174A); 5,6-dibromo-3-((4-bromophenyl)thio)-1H-indole (174AB); 5,7-dibromo-3-((4-bromophenyl)thio)-1H-indole (174AC); 5-bromo-3-((perchlorophenyl)thio)-1H-indole (174AD); 4,6-dibromo-3-((4-bromophenyl)thio)-1H-indole (174AE); 5-bromo-3-((4-bromophenyl)thio)-6-chloro-1H-indole (174AF); 5-bromo-3-((2,4,6-trichlorophenyl)thio)-1H-indole (174AG); 5-bromo-3-((3,4,5-tribromophenyl)thio)-1H-indole (174AH); 2-((5-bromo-1H-indol-3-yl)thio)phenol (174AI); 5-bromo-3-((2-chlorophenyl)thio)-1H-indole (174AJ); 3-((2-aminophenyl)thio)-2-methyl-1H-indol-5-ol (174AK); 3-((1H-indol-3-yl)thio)-5-bromo-1H-indole (174AL); 3-((4-bromophenyl)thio)imidazo[1,2-a]pyridine (174AN); 3-((2-hydroxyphenyl)thio)-2-methyl-1H-indol-5-ol (174AO); 3-((2-hydroxyphenyl)thio)-1H-indol-5-ol (174AP); 2-((5-methoxy-1H-indol-3-yl)thio)phenol (174AQ); 3-((2-bromophenyl)thio)-1H-indol-5-ol (174AR); 3-((2-bromophenyl)thio)-5-methoxy-1H-indole (174AS); (2-((5-bromo-1H-indol-3-yl)thio)phenyl)methanol (174AT); 5-bromo-3-((2-fluorophenyl)thio)-1H-indole (174AU); 5-bromo-3-((2-(trifluoromethyl)phenyl)thio)-1H-indole (174AV); 3-((2-bromophenyl)thio)-5-(trifluoromethyl)-1H-indole (174AX); 5-bromo-3-(o-tolylthio)-1H-indole (174AY); 5-bromo-3-((2-bromophenyl)thio)-2-methyl-1H-indole (174AZ); 4-bromo-3-((4-bromophenyl)thio)-1H-indole (174D); 3-((4-bromophenyl)thio)-5-fluoro-1H-indole (174E); 5-bromo-3-(naphthalen-1-ylthio)-1H-indole (174G); 7-bromo-3-((4-bromophenyl)thio)-1H-indole (174H); 5-bromo-3-((3-bromophenyl)thio)-1H-indole (174N); 5-bromo-3-((4-bromobenzyl)thio)-1H-indole (174O); 3-([1,1'-biphenyl]-4-ylthio)-5-bromo-1H-indole (174R); 5-bromo-3-((2,3-dichlorophenyl)thio)-1H-indole (174T); 5-bromo-3-((2,4-dichlorophenyl)thio)-1H-indole (174V); 5-bromo-3-((3,4-dichlorophenyl)thio)-1H-indole (174W); 5-bromo-2-((5-bromo-1H-indol-3-yl)thio)aniline (174X); 3-((5-bromo-1H-indol-3-yl)thio)aniline (174Y); 2-((5-(trifluoromethyl)-1H-indol-3-yl)thio)phenol (177A); 4-((5-(trifluoromethyl)-1H-indol-3-yl)thio)phenol (177B); 2-((5-(trifluoromethyl)-1H-indol-3-yl)thio)aniline (177C); 3-((2-fluorophenyl)thio)-5-(trifluoromethyl)-1H-indole (177D); 3-((2-bromophenyl)thio)-5-fluoro-1H-indole (177E); 5-(trifluoromethyl)-3-((2-(trifluoromethyl)phenyl)thio)-1H-indole (177F); 3-((2-ethylphenyl)thio)-5-(trifluoromethyl)-1H-indole (177G); (5-bromo-3-((2-bromophenyl)thio)-1H-indol-2-yl)methanol (177H); (3-((2-ethylphenyl)thio)-5-(trifluoromethyl)-1H-indol-2-yl)methanol (177I); 4-((1H-indol-3-yl)thio)phenol (156I); 3-((4-bromophenyl)thio)-1H-indole (156K); 3-((4-methoxyphenyl)thio)-1H-indole (156O); 2,3-bis((4-bromophenyl)thio)-1H-indole (156P); 3-((4-bromophenyl)thio)-2-methyl-1H-indole (172C); 5-bromo-3-((4-bromophenyl)thio)-1H-indole (172D); 3-((4-bromophenyl)thio)-5-methoxy-1H-indole (172E); 5-bromo-3-(phenylthio)-1H-indole (174AA); 3-((4-bromophenyl)thio)-5-chloro-1H-indole (174C); 5-bromo-3-((2-bromophenyl)thio)-1H-indole (174I); 5-bromo-3-((4-chlorophenyl)thio)-1H-indole (174J); 3-(benzylthio)-5-bromo-1H-indole (174K); 2-((5-bromo-1H-indol-3-yl)thio)benzo[d]thiazole (174L); 2-((5-bromo-1H-indol-3-yl)thio)aniline (174M); 5-bromo-3-((4-fluorophenyl)thio)-1H-indole (174P); 5-bromo-3-((4-methoxyphenyl)thio)-1H-indole (174Q); 5-bromo-3-(naphthalen-2-ylthio)-1H-indole (174S); 3-((4-bromophenyl)thio)-1H-indole (174U); 4-((5-bromo-1H-indol-3-yl)thio)aniline (174Z); 3-(phenylthio)-1H-indole (156L); 3-(pyridin-2-ylthio)-1H-indole (156M); 2-((1H-indol-3-yl)thio)benzoic acid (156N); 3-((4-bromophenyl)thio)-1H-pyrrolo[2,3-b]pyridine (172F); ethyl 3-((4-bromophenyl)thio)-1H-indole-2-carboxylate (172H); and/or 3-((4-bromophenyl)thio)-1-methyl-1H-indole (174B); N-((3-((4-hydroxyphenyl)thio)-1H-indol-5-yl)methyl)-4-(triethoxysilyl)butanamide (156SI); and/or 3-((2-aminophenyl)thio)-5-bromo-N-(3-(triethoxysilyl)propyl)-1H-indole-2-carboxamide (174SI).

In some embodiments, the antimicrobial methods can include contacting a pathogenic microbe with the compound such that the pathogenic microbe is selectively inhibited over a commensal microbe that contacts the compound. In some aspects, the method can include administering the selective antimicrobial compound to a subject.

In some embodiments, the methods can include applying the compound to a surface or within a body of an object. In some aspect, the object includes fabrics, bandages, tarps, flooring, mats, carpets, towels, linens, furniture, mattress, cabinet, countertop, bath tub, sink, faucet, hot tub, toys, underwear, socks, pants, shorts, skirt, dress, shirt, blouse, jersey, hat, scarf, medical devices, medical dressings, medical clothing, bed linens, privacy curtains, toys, bottles, crib, athletic equipment, handles, grips, camping items, pharmaceutical dosage form, or combinations thereof.

In some embodiments, the pathogenic microbe is a bacterium, virus, or a fungus. As such, the antimicrobial compound can be antibacterial, antiviral, or antifungal.

In some embodiments, the method can include contacting a pathogenic microbe with the compound such that the pathogenic microbe is selectively inhibited over a commensal microbe that contacts the compound.

In some embodiments, the method can include administering the compound to a subject.

In some embodiments, the method can include applying the compound to the skin of a subject.

In some embodiments, the method can include applying the compound to the skin of a subject at or around a groin area and/or feet area.

In some embodiments, the method can include applying the compound to a surface of an object.

In some embodiments, the subject has a pathogenic microbe infection.

In some embodiments, the method can include diagnosing the subject to have the pathogenic microbe infection.

In some embodiments, the pathogenic microbe is a bacterium or a fungus.

In some embodiments, the selective antimicrobial is applied to a solid object, whether particulate, porous, non-porous.

In some embodiments, the solid object is contacted to the skin of the subject.

In some embodiments, the method includes applying the selective antimicrobial to a surface of an object.

In some embodiments, the object includes fabrics, bandages, tarps, flooring, mats, carpets, towels, linens, furniture, mattress, cabinet, countertop, bathtub, sink, faucet, hot tub, toys, or combinations thereof.

In some embodiments, the object includes underwear, socks, pants, shorts, skirt, dress, shirt, blouse, jersey, hat, scarf, or combinations thereof.

In some embodiments, object includes children or baby items.

In some embodiments, the object includes athletic equipment.

In some embodiments, the object includes camping items.

In some embodiments, the invention is a compound of one of the embodiments.

In some embodiments, the invention is a composition having the compound of one of the embodiments.

In some embodiments, the invention is an object or article of manufacture having the compound of one of the embodiments.

In some embodiments, the object or pharmaceutical composition can include any of the compounds described herein that can be antimicrobial.

In some embodiments, the methods can include any of the compounds described herein that can be antimicrobial.

In one embodiment, a pharmaceutical composition can include a compound of one of the embodiments, and a pharmaceutically acceptable carrier containing the compound. In one aspect, the compound is present in a therapeutically effective amount to treat or inhibit a disease state. In one aspect, the disease state is a microbial infection.

Pharmaceutical compositions can include the compounds of the invention, and can include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (e.g., Tween®), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), dioleysl-phosphotidyl-ethanolamine (DOPE), and liposomes. Such compositions should contain a therapeutically effective amount of the compound, together with a suitable amount of carrier so as to provide the form for direct administration to the patient.

The compositions described herein can be administered for example, by parenteral, intravenous, subcutaneous, intramuscular, intracranial, intraorbital, ophthalmic, intraventricular, intracapsular, intraspinal, intracistemal, intraperitoneal, intranasal, aerosol or oral administration. Common carriers or excipients can be used for preparing pharmaceutical compositions designed for such routes of administration.

In some embodiments, the methods omit use of Compound 156I (4-((1H-indol-3-yl)thio)phenol) in any methods or in any composition or in any article of manufacture. Accordingly, the compounds used in the invention may omit a hydroxyl as a para-substituent on the ring A of the compound. In some aspects, the compounds may omit a hydroxyl as a para-substituent on the ring A of the compound when there is no $R^2$ substituent. In some aspects, the compounds may omit a hydroxyl as a para-substituent on the ring A of the compound when there is no $R^3$ substituent. In some aspects, the compounds may omit a hydroxyl as a para-substituent on the ring A as the only $R^1$ substituent of the compound. In some aspects, the compounds may omit a hydroxyl as a para-substituent on the ring A, unless there is another $R^1$ substituent, a $R^2$ substituent, or a $R^3$ substituent. In some aspects, the compounds may omit a hydroxyl as a para-substituent on the ring A when linked to the $Z^5$ carbon. In some aspects, the compounds may omit a hydroxyl as a substituent on the ring A.

In some embodiments, the compounds may omit a para-substituent on the ring A when there is no other $R^1$ substituent. In some aspects, the compounds may omit a para-substituent on the ring A when there is a $R^2$ substituent on the $Z^3$ carbon. In some aspects, the compounds may omit a para-substituent on the ring A. In some aspects, the compounds may omit a para-substituent on the ring A when there is only a $R^2$ substituent on the $Z^3$ carbon.

In some embodiments, the methods omit using the antimicrobial compounds to inhibit *B. subtilis, S. aurens, S. viridochromogenes, E. coli, C. alicans*, and/or *M. miehei*. In some aspects, the methods omit using Compound 156I or other compound having a hydroxy as a $R^1$ para-substituent on ring A. In some aspects, the methods omit using any compound recited herein as omitted.

In some embodiments, a method is provided to inhibit a microbe by contacting the compound to the microbe. The contacting may include having the compound on a surface of an object, such as an article of manufacture.

In some embodiments, the microbe is only a bacterium. In some embodiments, the microbe is only a fungus. In some embodiments, the microbe is only a virus. In these embodiments, the microbes are inhibited by the compounds. In these embodiments, the microbes are pathogenic microbes that are inhibited. In these embodiments, the pathogenic microbes are inhibited more than commensal microbes.

In some embodiments, the microbes that are inhibited are recited in the tables herein.

Compounds

In some embodiments, the present invention includes select compounds, which can be used as antimicrobials as recited herein. In these embodiments, the present invention includes the compounds and compositions thereof. These compounds and compositions can be used in the methods recited herein. The compounds that are provided herein are recited to be inventive compounds. While all of the compounds can be used in the methods, the compounds recited in this section are novel and can be provided as compounds or in compositions for use in the recited methods or in other methods.

In some embodiments, a compound can have a structure of Formula A, or derivative thereof, salt thereof, or stereoisomer thereof, or having any chirality at any chiral center, or tautomer, polymorph, solvate, or combination thereof:

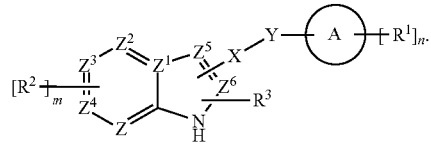

Formula A

The variables of the compounds of the formulae can include the following: ring A is a phenyl, indolyl, naphthyl, or benzothiazolyl; X is NH, O, $CH_2$, $CH_2CH_2$, N=N, S, SO, or $SO_2$; Y is a linker or bond; Z is CH, $CR^2$, or N; $Z^1$ is C or N to form an imidazopyridine; each $Z^2$, $Z^3$, or $Z^4$ is independently CH, $CR^2$, or N; each $Z^5$ or $Z^6$ is C or CH; each $R^1$, $R^2$, and $R^3$ is independently a substituent, and at least one of $R^1$, $R^2$, or $R^3$ is a substituent other than a hydrogen; m is 0, 1, 2, 3, or 4; and n is 0 or a positive integer. In some aspects, the following criteria apply to the compounds: when X is S and ring A is a phenyl, $R^1$ is a substituent other than a hydrogen; when X is S and ring A is a benzothiazolyl and linked to the $Z^5$ carbon and $R^3$ is hydrogen or alkyl, $R^2$ is not only a substituent on the $Z^3$ carbon or only a hydrogen; when X is S and ring A is phenyl and linked to the $Z^5$ carbon and $R^2$ is only a substituent on the $Z^3$ carbon or hydrogen and $R^3$ is hydrogen or alkyl, $R^1$ is not a para-substituent when $R^1$ is a halogen, alkoxy, hydroxyl, or amine and $R^2$ is a halogen or alkoxy; when X is S and ring A is phenyl and linked to the $Z^5$ carbon and $R^2$ is only a halogen substituent on the $Z^3$ carbon or a hydrogen, $R^1$ is not a ortho-substituent when $R^1$ is an amine or halogen and $R^2$ is a halogen or alkoxy; when X is S and ring A is a naphthyl and linked to the $Z^5$ carbon, $R^2$ is not only a substituent on the $Z^3$ carbon or hydrogen, when X is S and ring A is phenyl and linked to the $Z^5$ carbon and $R^1$ is a para-substituent halogen, $R^3$ is not an alkyl or

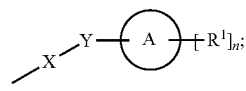

and when X is S and ring A is a phenyl and $Z^1$ is N and $R^2$ is hydrogen and $R^3$ is hydrogen, $R^1$ is not a para-substituent halogen.

In some embodiments, the variables of the formulae of this section can be the same as defined herein.

In some embodiments, ring A is a phenyl linked to the $Z^5$ carbon and the compounds includes at least one of: Y is a bond; $R^1$ is a para-substituent halogen, alkoxy, hydroxyl, or amine when X is SO or $SO_2$; $R^2$ is a halogen or alkoxy substituent on the $Z^3$ carbon when X is SO or $SO_2$; $R^2$ is a alkyl ester or is not a substituent on $Z^3$ carbon or hydrogen; $R^2$ is not a substituent on $Z^3$ carbon or hydrogen; m is greater than 1; and n is greater than 1.

In some embodiments, ring A is linked to the $Z^6$ carbon.

In some embodiments, $R^2$ is a halogen or alkoxy substituent on the $Z^3$ carbon when X is NH, O, $CH_2$, $CH_2CH_2$, N=N, SO or $SO_2$.

In some embodiments, $R^1$ is a para-substituent halogen, alkoxy, hydroxyl, or amine when X is NH, O, $CH_2$, $CH_2CH_2$, N=N, SO or $SO_2$.

In some embodiments, $R^1$ is not only a para-substituent or ortho-substituent when X is S and $R^2$ is a substituent on the $Z^3$ carbon or a hydrogen and R3 is hydrogen or alkyl.

In some embodiments, ring A is phenyl liked to the $Z^5$ carbon, the structure is characterized by at least one of: Y is a bond; $R^1$ is not a para-substituent that is halogen, hydroxyl, or alkoxy or an ortho-substituent that is an amine or halogen; $R^2$ is not only a $Z^3$ substituent of halogen or alkoxy; $R^2$ is a $Z^4$ substituent; $R^3$ is a substituent other than hydrogen or straight chain alkyl; X is NH, O, $CH_2$, $CH_2CH_2$, N=N, SO or $SO_2$; $Z^5$ carbon and $Z^6$ carbon have different substituents; m is at least 2; or n is at least 2.

In some embodiments, the structure is characterized by at least one of: Y is a bond; ring A is a benzothiazolyl or naphthyl having at least one $R^1$ substituent; ring A is a naphthyl linked to Y through the Cl carbon (e.g., carbon adjacent to a carbon common to both rings); $R^1$, $R^2$, or $R^3$ includes an aryl; at least one $R^1$ is a meta-substituent or an ortho-substituent other than amine; at least one $R^2$ is a substituent on a carbon other than the $Z^3$ carbon; X is NH, O, $CH_2$, $CH_2CH_2$, N=N, SO or $SO_2$; m is at least 2; or n is at least 2.

In some embodiments, ring A is linked to the $Z^6$ carbon and $Z^5$ includes $R^3$ being a substituent other than hydrogen or alkyl when ring A is a phenyl.

In some embodiments, the compound has a structure of Formula B or derivative thereof, salt thereof, or stereoisomer thereof, or having any chirality at any chiral center, or tautomer, polymorph, solvate, or combination thereof:

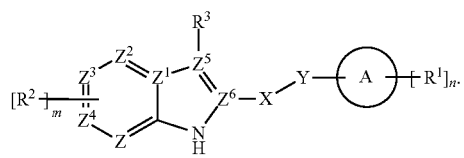

Formula B

In Formula B, wherein R is not

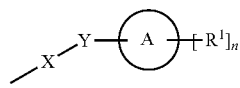

when the X, Y, Ring A, $R^1$, and n are identical to each other or when ring A is a phenyl and $R^1$ is a halogen para-substituent. Here, the two substituents are different.

In some embodiments, the compound having a structure of Formula C or derivative thereof, salt thereof, or stereoisomer thereof, or having any chirality at any chiral center, or tautomer, polymorph, solvate, or combination thereof:

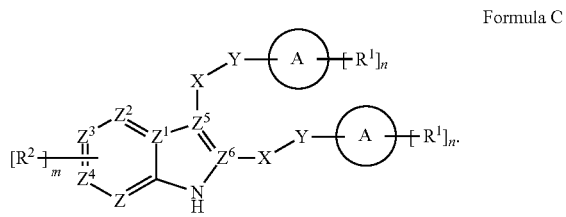

Formula C

In Formula C, each $R^1$ is different when both substituents include the same X, same Y, same n, ring A as a phenyl and $R^1$ is a halogen para-substituent. Here, the two substituents can be the same except for when include the same X, same Y, same n, ring A as a phenyl and $R^1$ is a halogen para-substituent. Otherwise, the two substituents can be the same or can be different from each other.

In some embodiments, the compound has a structure of Formula D or derivative thereof, salt thereof, or stereoisomer thereof, or having any chirality at any chiral center, or tautomer, polymorph, solvate, or combination thereof:

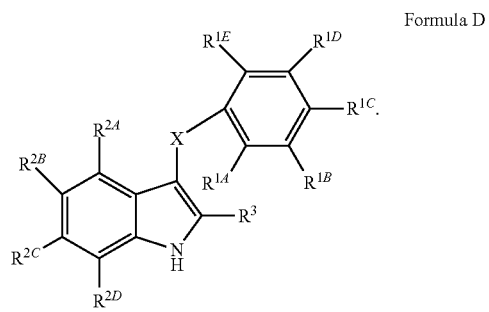

Formula D

In some embodiments of Formula D, the structure excludes at least one of: $R^{1C}$ being a halogen, hydroxyl, or alkoxy when rest of R groups are hydrogen; $R^3$ is an alkyl; $R^{1C}$ and $R^{2B}$ each independently being a halogen, hydroxyl, or alkoxy when rest of R groups are hydrogen; $R^{1A}$ and $R^{2B}$ each independently being a halogen, when rest of R groups are hydrogen; $R^{1A}$ being an amine and $R^{2B}$ being a halogen, when rest of R groups are hydrogen; $R^{2B}$ being a halogen, hydroxyl, or alkoxy when rest of R groups are hydrogen; or X is S.

In some embodiments of Formula D, the structure includes at least one of: $R^{1C}$ being halogen and $R^{2C}$ being halogen; $R^{1A}$, $R^{1C}$, and $R^{1E}$ each being a non-hydrogen substituent; $R^{1B}$, $R^{1C}$, and $R^{1D}$ each being a non-hydrogen substituent; $R^{1A}$ being halogen or hydroxyl; $R^{1A}$ being a fluorocarbon; $R^{1A}$ being an alkyl; $R^{1A}$ being a non-hydrogen substituent when $R^3$ is an alkyl; $R^{1A}$ being a non-hydrogen substituent when $R^{2B}$ is a hydroxy or alkoxy; $R^{2B}$ being an alkylester; $R^{2B}$ and $R^{2c}$ each being a non-hydrogen substituent; $R^{2A}$ and $R^{2c}$ each being a non-hydrogen substituent; $R^{2B}$ and $R^{2D}$ being a non-hydrogen substituent; $R^{2B}$ being a fluorocarbon; $R^3$ being an alkynol (e.g., alkyl alcohol); each of $R^{1A}$ through $R^{1E}$ being a non-hydrogen substituent; or X is NH, O, $CH_2$, $CH_2CH_2$, N=N, SO or $SO_2$.

In some embodiments, the novel compounds can be any of the compounds of the formulae provided herein.

In some embodiments, the novel compounds can be included in composition that includes: the novel compound of one of the embodiments; and a carrier having the compound. In some aspects, the carrier is a pharmaceutically acceptable carrier.

In some embodiments, the novel compounds can be included in an article of manufacture that includes: the novel compound of one of the embodiments; and a material having the compound. In some aspects, the material includes the compound within a body of the material. In some aspects, the material includes the compound on a surface of the material.

In some embodiments, Formula C2D includes: $R^{14}$ being F, $CF_3$, $CH_3$, carboxy (e.g., carboxylic acid C(O)OH), or methanol; $R^{1C}$ being H or F; $R^{2B}$ being Br, $CH_3$, or $CF_3$; $R^3$ being methyl, ethyl, isopropyl, or tert-butyl; $R^4$ is H; the rest of the R groups are H; and X is NH, O, $CH_2$, $CH_2CH_2$, N=N, S, SO, or $SO_2$.

In some embodiments, each $R^1$, $R^2$, $R^3$ and/or $R^4$ is independently a substituent as described herein that further includes an end group that is functional to function as a conjugation moiety. That is, any substituent recited herein can further include a conjugation moiety at a terminal end, which conjugation moiety can be used to link the antimicrobial to a substrate or any material. The examples of conjugation moieties can include alkoxy silicones (e.g., triethoxy silicon), biotin, carboxylic acid, amine, halide, or any other common reactive chemical moiety that can be used to form a covalent bond with a substrate. In some aspects, only $R^2$ or $R^3$ may be a substituent as described herein that further includes an end group that is functional to function as a conjugation moiety. In some aspects, $R^4$ is hydrogen.

In some embodiments, each $R^1$, $R^2$, $R^3$ and/or $R^4$ is independently a substituent as described herein that further includes a polymer, such as a water soluble polymer, such as a poly ether (e.g., PEG). The polymer can be attached to the ring structure, within the substituent, or as a terminal portion of the substituent. For example, the antimicrobials can be PEGylated for improved water solubility. In some aspects, only $R^2$ or $R^3$ may be a substituent as described herein that further includes a polymer. In some aspects, $R^4$ is hydrogen.

In some embodiments, an antimicrobial compound having a structure of Formula 1 or other formulae, or derivative thereof, salt thereof, or stereoisomer thereof, or having any chirality at any chiral center, or tautomer, polymorph, solvate, or combination thereof: wherein ring A is a cycloalkyl, heterocycloalkyl, aryl, heteroaryl, or polycycle combination thereof; X is NH, O, $CH_2$, $CH_2CH_2$, N=N, S, SO, or $SO_2$; Y is a linker or bond; Z is CH, $CR^2$, or N; $Z^1$ is C or N to form an imidazopyridine; each $Z^2$, $Z^3$, or $Z^4$ is independently CH, $CR^2$, or N; each $Z^5$ or $Z^6$ is C or CH; each $R^1$, $R^2$, and $R^3$ is independently a substituent; m is 0, 1, 2, 3, or 4; and n is 0 or a positive integer, wherein at least one $R^1$, $R^2$, $R^3$ and/or $R^4$ independently includes —$R^5$-$R^6$-$R^7$, wherein: $R^5$ is O, NH, or a saturated or unsaturated hydrocarbon spacer of $C_0$-$C_{10}$; $R^6$ is a functional linker; $R^7$ is a PEG or conjugation moiety.

Figure 4:
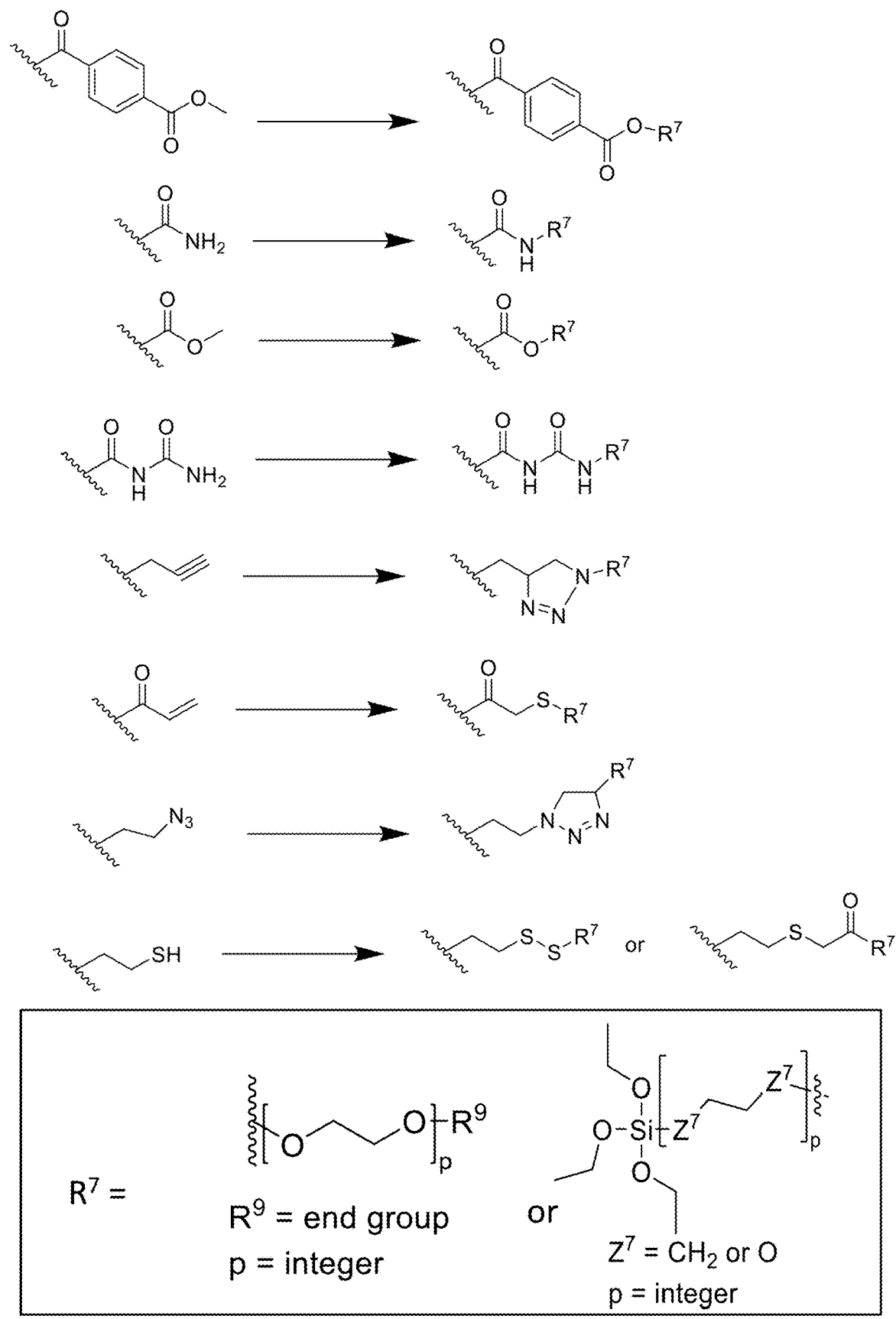
FIG. 4 shows examples of substituents for the compounds to include a PEG polymer or a trimethoxy silane for use as a conjugation moiety.

For example, FIG. 4 shows a reaction scheme for the above $R^6$ functional groups that can be reacted with a group having a PEG or a conjugation group, such as $R^7$. As a result, Fig. shows an example of at least one $R^1$, $R^2$, $R^3$ and/or $R^4$ that independently includes —$R^6$-$R^7$, wherein: $R^6$ is a functional linker and $R^7$ is a PEG or conjugation moiety. For example, the —$R^7$ can include the following structure that has a PEG.

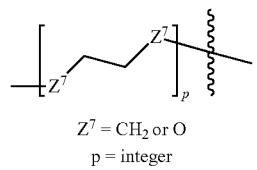

$Z^7 = CH_2$ or O
p = integer

In some embodiments, at least one $R^1$, $R^2$, $R^3$ and/or $R^4$ independently includes —$R^5$-$R^6$, wherein: $R^5$ is O, NH, or a saturated or unsaturated hydrocarbon spacer of $C_0$-$C_{10}$; $R^6$ is an end group that is functional for use in PEGylation. Here, the $R^6$ is capable of reacting with and being conjugated to a PEG or conjugation moiety as $R^7$. For example, the $R^6$ can be at least one of the following groups:

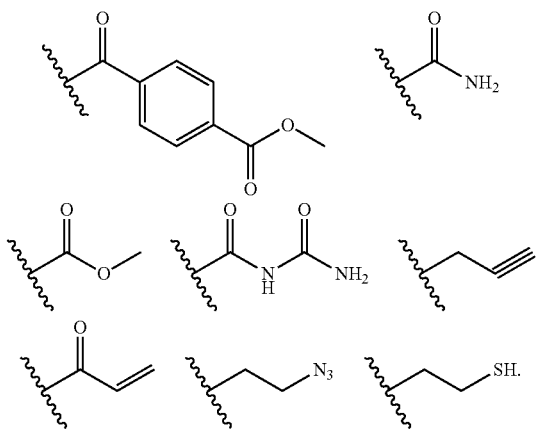

In some embodiments, at least one $R^1$, $R^2$, $R^3$ and/or $R^4$ independently includes —$R^5$-$R^8$, wherein: $R^5$ is O, NH, or a saturated or unsaturated hydrocarbon spacer of $C_0$-$C_{10}$; $R^8$ is an end group that is non-functional for PEGylation. For example, the $R^8$ can be at least one of the following groups:

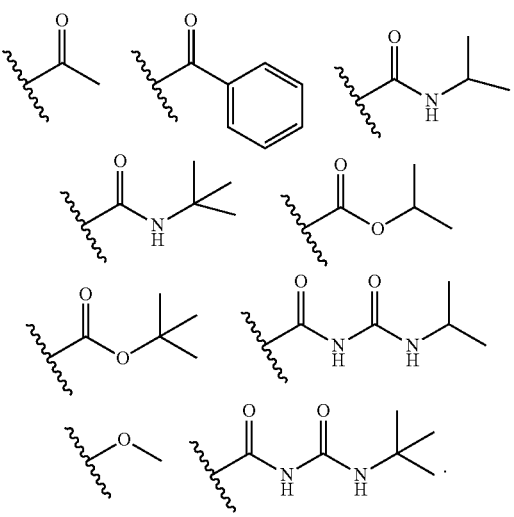

In some embodiments, each $R^1$, $R^2$, $R^3$ and/or $R^4$ independently can include a diazirine group, such as an alkyl diazirine. An example is 3-isopropyl-3-methyl-3H-diazirine.

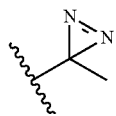

3-isopropyl-3-methyl-3H-diazirine

In some embodiments, $R^2$ or $R^3$ includes a terminal alkoxy silicone group. The alkoxy silicon can be a di-alkoxy silicon or tri-alkoxy silicone. For example, the alkoxy silicone can be triethoxy silicone. An example of the triethoxy silicon-containing substituent is provided as follows:

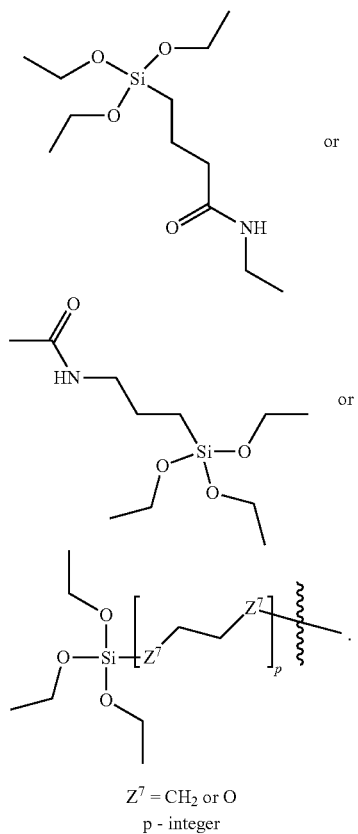

$Z^7$ = CH$_2$ or O
p - integer

In some embodiments, the ring A of the formulae provided herein can include a thiadiazole or a thiazole, which can be substituted with an $R^1$ group as defined herein. The R1 group can be on any possible atom of the thiadiazole or thiazole. The thiadiazole and thiazole structures for ring A are shown below.

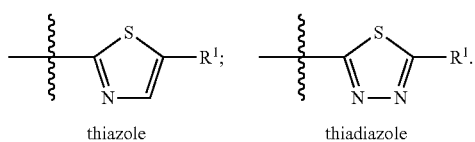

thiazole      thiadiazole

For example, the thiazole and thiadiazole for ring A with the $R^1$ substituent can be present as follows:

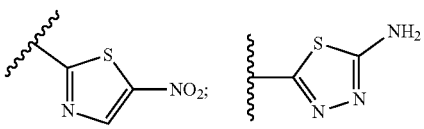

In some embodiments, the compounds can be selected from the group of (structure name (Compound No.)): 3-((4-bromophenyl)thio)-6-fluoro-1H-indole (172A); 2-((4-bromophenyl)thio)-3-methyl-1H-indole (172B); methyl 3-((4-bromophenyl)thio)-1H-indole-5-carboxylate (172G); 5-bromo-3-((4-bromophenyl)sulfinyl)-1H-indole (172I); 5-bromo-3-((4-bromophenyl)sulfonyl)-1H-indole (172J); 6-bromo-3-((4-bromophenyl)thio)-1H-indole (174A); 5,6-dibromo-3-((4-bromophenyl)thio)-1H-indole (174AB); 5,7-dibromo-3-((4-bromophenyl)thio)-1H-indole (174AC); 5-bromo-3-((perchlorophenyl)thio)-1H-indole (174AD); 4,6-dibromo-3-((4-bromophenyl)thio)-1H-indole (174AE); 5-bromo-3-((4-bromophenyl)thio)-6-chloro-1H-indole (174AF); 5-bromo-3-((2,4,6-trichlorophenyl)thio)-1H-indole (174AG); 5-bromo-3-((3,4,5-tribromophenyl)thio)-1H-indole (174AH); 2-((5-bromo-1H-indol-3-yl)thio)phenol (174AI); 5-bromo-3-((2-chlorophenyl)thio)-1H-indole (174AJ); 3-((2-aminophenyl)thio)-2-methyl-1H-indol-5-ol (174AK); 3-((1H-indol-3-yl)thio)-5-bromo-1H-indole (174AL); 3-((4-bromophenyl)thio)imidazo[1,2-a]pyridine (174AN); 3-((2-hydroxyphenyl)thio)-2-methyl-1H-indol-5-ol (174AO); 3-((2-hydroxyphenyl)thio)-1H-indol-5-ol (174AP); 2-((5-methoxy-1H-indol-3-yl)thio)phenol (174AQ); 3-((2-bromophenyl)thio)-1H-indol-5-ol (174AR); 3-((2-bromophenyl)thio)-5-methoxy-1H-indole (174AS); (2-((5-bromo-1H-indol-3-yl)thio)phenyl)methanol (174AT); 5-bromo-3-((2-fluorophenyl)thio)-1H-indole (174AU); 5-bromo-3-((2-(trifluoromethyl)phenyl)thio)-1H-indole (174AV); 3-((2-bromophenyl)thio)-5-(trifluoromethyl)-1H-indole (174AX); 5-bromo-3-(o-tolylthio)-1H-indole (174AY); 5-bromo-3-((2-bromophenyl)thio)-2-methyl-1H-indole (174AZ); 4-bromo-3-((4-bromophenyl)thio)-1H-indole (174D); 3-((4-bromophenyl)thio)-5-fluoro-1H-indole (174E); 5-bromo-3-(naphthalen-1-ylthio)-1H-indole (174G); 7-bromo-3-((4-bromophenyl)thio)-1H-indole (174H); 5-bromo-3-((3-bromophenyl)thio)-1H-indole (174N); 5-bromo-3-((4-bromobenzyl)thio)-1H-indole (174O); 3-([1,1'-biphenyl]-4-ylthio)-5-bromo-1H-indole (174R); 5-bromo-3-((2,3-dichlorophenyl)thio)-1H-indole (174T); 5-bromo-3-((2,4-dichlorophenyl)thio)-1H-indole (174V); 5-bromo-3-((3,4-dichlorophenyl)thio)-1H-indole (174W); 5-bromo-2-((5-bromo-1H-indol-3-yl)thio)aniline (174X); 3-((5-bromo-1H-indol-3-yl)thio)aniline (174Y); 2-((5-(trifluoromethyl)-1H-indol-3-yl)thio)phenol (177A); 4-((5-(trifluoromethyl)-1H-indol-3-yl)thio)phenol (177B); 2-((5-(trifluoromethyl)-1H-indol-3-yl)thio)aniline (177C); 3-((2-fluorophenyl)thio)-5-(trifluoromethyl)-1H-indole (177D); 3-((2-bromophenyl)thio)-5-fluoro-1H-indole (177E); 5-(trifluoromethyl)-3-((2-(trifluoromethyl)phenyl)thio)-1H-indole (177F); 3-((2-ethylphenyl)thio)-5-(trifluoromethyl)-1H-indole (177G); (5-bromo-3-((2-bromophenyl)thio)-1H-indol-2-yl)methanol (177H); (3-((2-ethylphenyl)thio)-5-(trifluoromethyl)-1H-indol-2-yl)methanol (177I); N-((3-((4-hydroxyphenyl)thio)-1H-indol-5-yl)methyl)-4-(triethoxysilyl)butanamide (156SI); and/or 3-((2-aminophenyl)thio)-5-bromo-N-(3-(triethoxysilyl)propyl)-1H-indole-2-carboxamide (174SI), and combinations thereof.

In some aspects, 4-(1H-indol-3-yl-sulfanyl)phenol and its close derivatives (e.g., para $R^1$ hydroxyl substituent) are specifically omitted. In some aspects, the omitted compounds have an $R^1$ hydroxyl in the para position. In some aspects, the omitted compounds have an $R^1$ hydroxyl in any position. In some aspects, the included compounds include a $R^2$, $R^3$, or $R^4$ substituent other than hydrogen with $R^1$ is a hydroxyl, such as the para position.

In some embodiments, the compounds exclude the following compounds: 4-((1H-indol-3-yl)thio)phenol (156I); 3-((4-bromophenyl)thio)-1H-indole (156K); 3-((4-methoxyphenyl)thio)-1H-indole (156O); 2,3-bis((4-bromophenyl)thio)-1H-indole (156P); 3-((4-bromophenyl)thio)-2-methyl-1H-indole (172C); 5-bromo-3-((4-bromophenyl)thio)-1H-indole (172D); 3-((4-bromophenyl)thio)-5-methoxy-1H-indole (172E); 5-bromo-3-(phenylthio)-1H-indole (174AA); 3-((4-bromophenyl)thio)-5-chloro-1H-indole (174C); 5-bromo-3-((2-bromophenyl)thio)-1H-indole (174I); 5-bromo-3-((4-chlorophenyl)thio)-1H-indole (174J); 3-(benzylthio)-5-bromo-1H-indole (174K); 2-((5-bromo-1H-indol-3-yl)thio)benzo[d]thiazole (174L); 2-((5-bromo-1H-indol-3-yl)thio)aniline (174M); 5-bromo-3-((4-fluorophenyl)thio)-1H-indole (174P); 5-bromo-3-((4-methoxyphenyl)thio)-1H-indole (174Q); 5-bromo-3-(naphthalen-2-ylthio)-1H-indole (174S); 3-((4-bromophenyl)thio)-1H-indole (174U); 4-((5-bromo-1H-indol-3-yl)thio)aniline (174Z); and combinations thereof. While these compounds can be used in the methods, they are specifically excluded from some embodiments of compounds and compositions.

In some embodiments, the compounds (and the methods) can exclude the following compounds: 3-(phenylthio)-1H-indole (156L); 3-(pyridin-2-ylthio)-1H-indole (156M); 2-((1H-indol-3-yl)thio)benzoic acid (156N); 3-((4-bromophenyl)thio)-1H-pyrrolo[2,3-b]pyridine (172F); ethyl 3-((4-bromophenyl)thio)-1H-indole-2-carboxylate (172H); 3-((4-bromophenyl)thio)-1-methyl-1H-indole (174B); and combinations thereof. In some aspects, these compounds are specifically excluded from the inventive compounds, compositions, and methods.

In some embodiments, the compounds of this section that are not indicted to be omitted or excluded in any way can be used in methods for treating, preventing, or inhibiting a microbial infection.

In some embodiments, a method of inhibiting microbes (e.g., bacteria, fungi, or virus) can include contacting a microbe (e.g., pathogenic) with the compound such that the microbe is selectively inhibited. In some aspects, the compound is any compound recited herein that is not omitted or excluded.

EXAMPLES

A library of antimicrobial bacterial extracts were tested for antifungal activity against *T. rubrum*. The compounds provided herein emerged as the most potent. Targeted potency against pathogenic microbes was desired, and the compounds demonstrated significantly less potency against skin commensals *M. furfur*, *S. epidermidis*, and *Micrococcus* sp. Subsequent purification using bioassay guided fractionation, HPLC, and LC-MS produced a potent and pure compound from 8 liters of CFD-110 extract. NMR was used to determine the molecular structure of CFD-110.

Generally, the compounds were synthesized using the method as previously described [Tetrahedron 71 (2015) 8885-8891]. Briefly, a mixture of indole (1 eq.), 4-hydroxythiophenol (1 eq.) and TBHP (1 eq.) were dissolved in MeCN at 60° C. in a flask, then iodine (0.2 eq.) was added. The reaction proceeded under an air atmosphere for 0.5-1.0 h until complete consumption of starting material as monitored by TLC. The reaction mixture was quenched by the addition of saturated aqueous $Na_2S_2O_3$ and then extracted with EtOAc. The combined organic layer was concentrated under vacuum and the crude product was purified by prep-HPLC to produce compound CFD-110 (90% yield).

The Table 1 shows selectivity of CFD-174M, CFD-156I and CFD-156K against pathogens and skin commensals. Table 9 also shows the selectivity index (SI) for various compounds using *B. subtilis* MICs.

Table 2 shows the MBC (minimum bactericidal concentration) and MFC (minimum fungicidal concentration) of some of the antimicrobial compounds with *Bacillus subtilis*, *Bacillus thuringiensis*, *Burkholderia cenocepacia*, *Burkholderia thailandensis*, *Candida glabrata*, *Trichophyton rubrum* (Castellani Sabouraud), and *Francisella tularensis* subsp. Holarctica Strain LVSR NR-597.

Table 3 shows the MIC values for *Staphylococcus aureus* with VSSA (Vancomycin sensitive *S. aureus*), VRSA (Vancomycin resistant *S. aureus*), and MRSA (Methicillin resistant *S. aureus*).

Table 4 shows the MIC values for *Bacillus subtilis* strains.

Table 5 shows the MIC values for *Bacillus thuringiensis* strains.

Table 6 shows the MIC values for *TV. gonorrhoeae* strains.

Table 7 shows the MIC values for *Candida* sp. with species *C. glabrata* strains and *C. albicans* strains.

Table 8 shows the MIC values for *Francisella tularensis* strains.

Table 10 shows an experimental protocol for studies for toxicity of the antimicrobial compounds in mice, where the dosing route, dose, dosing solution concentration, and dosing volume are described. The vehicle is 40% PEG300 solution in 0.9% NaCl. In Table 10, Compound 1 is Compound 174AU, Compound 2 is Compound 174AZ, and Compound 3 is Compound 174AI. The mice had an average weight of 22-23 grams and were 6-week-old Balb/c mice. Table 11 shows the result of the body weight over 7 days. As shown, these antimicrobial compounds did not have significant toxicity as evidenced by the weight staying consistent with small reductions. Thus, the compounds are useful for in vivo antimicrobial administration.

Additionally, the antimicrobial compounds were analyzed for cytotoxicity. The compounds underwent cytotoxicity testing in the HepG2 liver cell line, and some of the best compounds based on selectivity index moved into the human HepaRG primary-like cell line for further cytotoxicity testing in more predictive cells with a natural drug metabolism enzyme (DME) profile. We utilized the standard MTT assay (Promega CellTiter 96) and GraphPad Prism 7 software to determine EC50 values for each analogue. Briefly, 20,000 HepG2 cells in 200 μl of the ATCC recommended media were seeded in each well of a 96-well plate with a moisture barrier created in the outermost wells. The cells were allowed to attach overnight at 37° C., and then observed under phase contrast microscopy for proper morphological characteristics. If cells appeared healthy and attached, test compounds were added in 7 concentrations from 1-64 μg/ml (n=3) from freshly prepared DMSO stock plates. The cells were incubated for 48 h and then stained with [3-(4,5-dimethylthiazol-2-yl)-2,5-diphenyltetrazolium bromide (MTT)] and incubated at 37° C. for 4 h. Once incubations were complete, the spectrophotometric absorbance of the samples was measured at a wavelength of 595 nm. Acetaminophen EC50 served as the positive control and 1% DMSO samples are considered negative control and are used as reference for subsequent IC50 calculations. For the HepaRG assay, NoSpin HepaRG™ cells (Lonza, cat #NSH-PRG) were thawed and plated with 20,000 cells per well. They were allowed to attach for 4 h (optimal DME profile per Lonza's testing) before dosing following the identical protocol as above. Table 9 below provides results for the EC50.

Additionally, an extensive study to explore the mechanism of action (MOA) has revealed that the series likely has 2 MOAs with varying degrees of each in different analogues. Fluorescence microscopy and radiolabeling studies have clearly shown cell wall synthesis inhibition as a MOA for the series of compounds with Compound No. 174I. Transcriptomic and metabolic studies have demonstrated branched chain amino acid biosynthesis inhibition as another MOA for 174I and 174M. The combination of cell wall synthesis inhibition and BCAA synthesis inhibition is the novel, dual mechanism behind our potent, broad-spectrum compounds. Multiple MOAs are ideal for combating AMR because the pathogen has to evolve 2 resistance mechanisms simultaneously to survive treatment with a dual MOA antimicrobial (e.g., antibiotic).

Figure 1B:
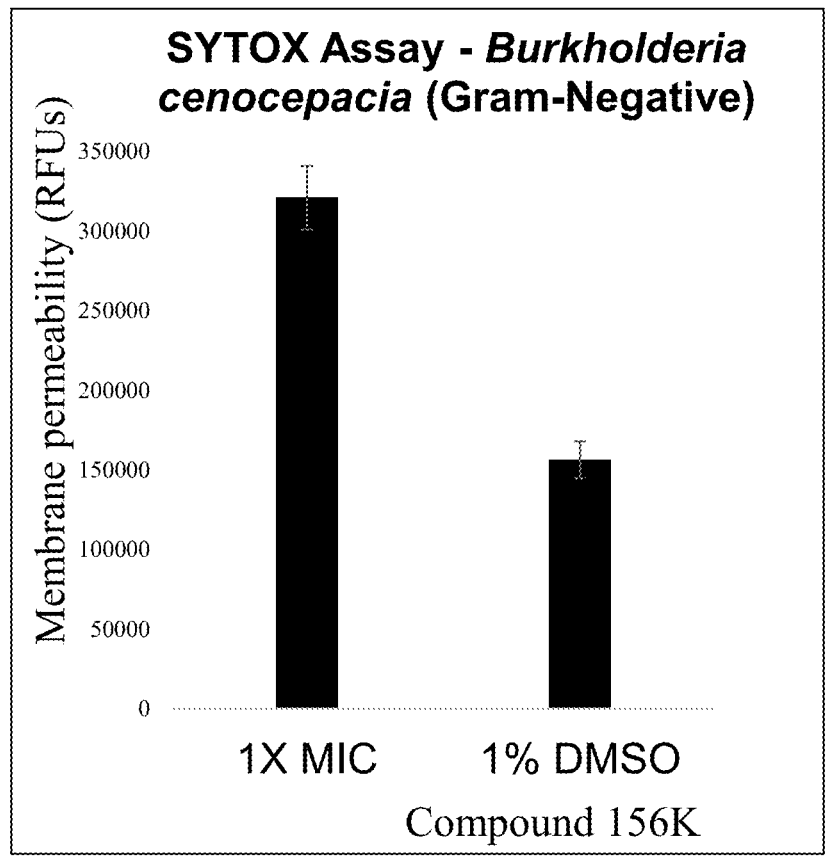
FIG. 1B includes a graph that shows the cytotoxicity of an antimicrobial Compound 156K by membrane permeability compared to the MIC or DMSO.
Figure 1C:
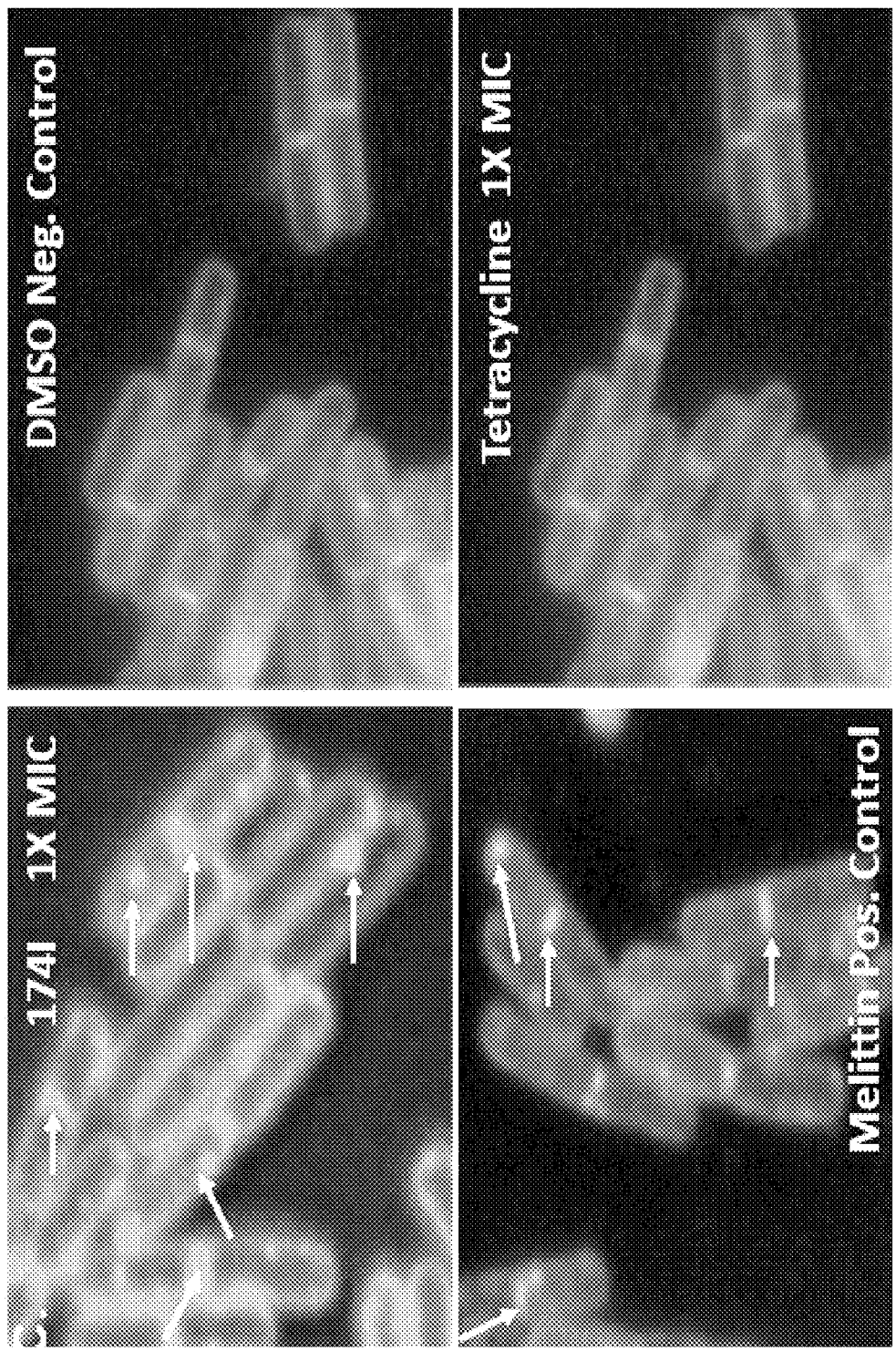
FIG. 1C shows an image with FM 4-64 stained *B. subtilis* cells imaged with a fluorescence microscope.

Cell wall permeability/disruption measured by SYTOX green fluorescence assay which emits only when able to enter the cell and bind DNA; FM 4-64 dye (red) which aggregates in disrupted cell walls. FIG. 1A shows SYTOX assay on *S. aureus* with analogue 174I. Concentrations are relative to the MIC, and a clear dose-dependent increase in permeability is demonstrated by the data. MEL is the positive control melittin which permeabilizes cells. FIG. 1B shows SYTOX assay with *B. cenocepacia* demonstrating cell permeabilization. FIG. 1C shows an image with FM 4-64 stained *B. subtilis* cells imaged with a fluorescence microscope. The arrows point to areas of aggregation and cell wall disruption seen in both analogue 174I and melittin treated cells only.

Figure 2A:
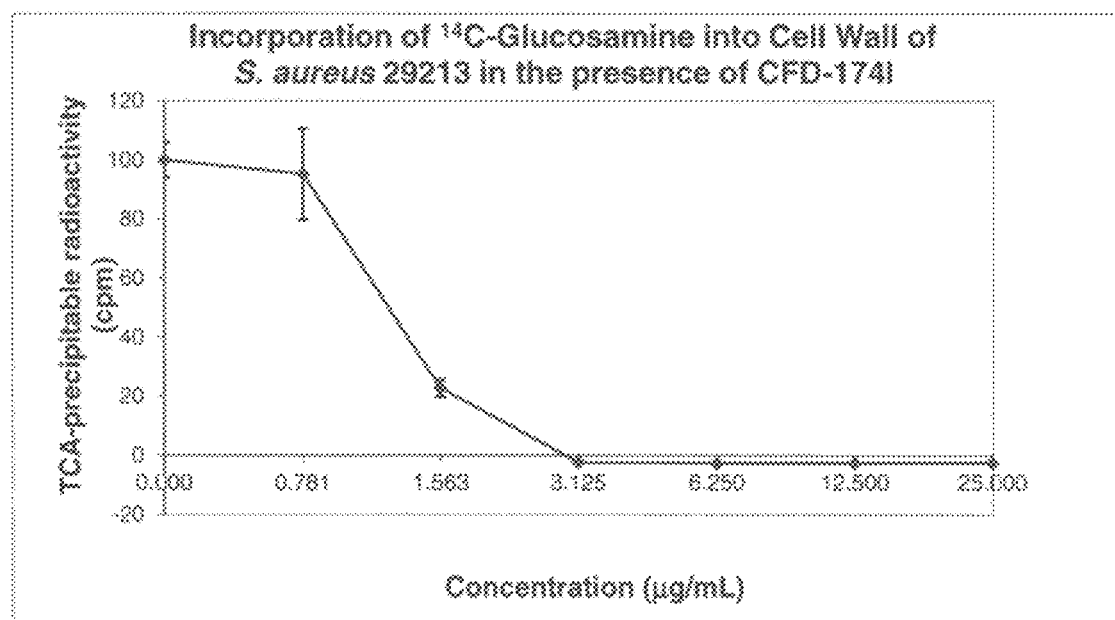
FIG. 2A includes a graph that shows Compound 174I increasingly inhibits glucosamine from incorporating into a cell wall of *S. aureus* strain with increasing concentration.
Figure 2B:
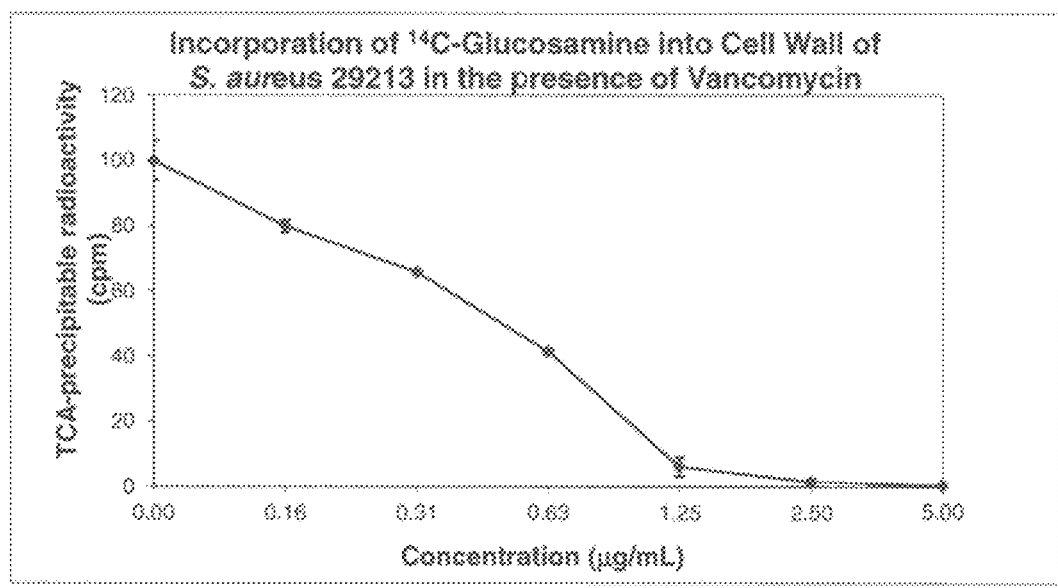
FIG. 2B includes a graph that shows vancomycin increasingly inhibits glucosamine from incorporating into a cell wall of *S. aureus* strain with increasing concentration.

FIG. 2A-2B show the macromolecular synthesis assay dose-response curve demonstrating substantial cell wall synthesis inhibition with 174I (FIG. 2A) compared to vancomycin (FIG. 2B).

Figure 2C:
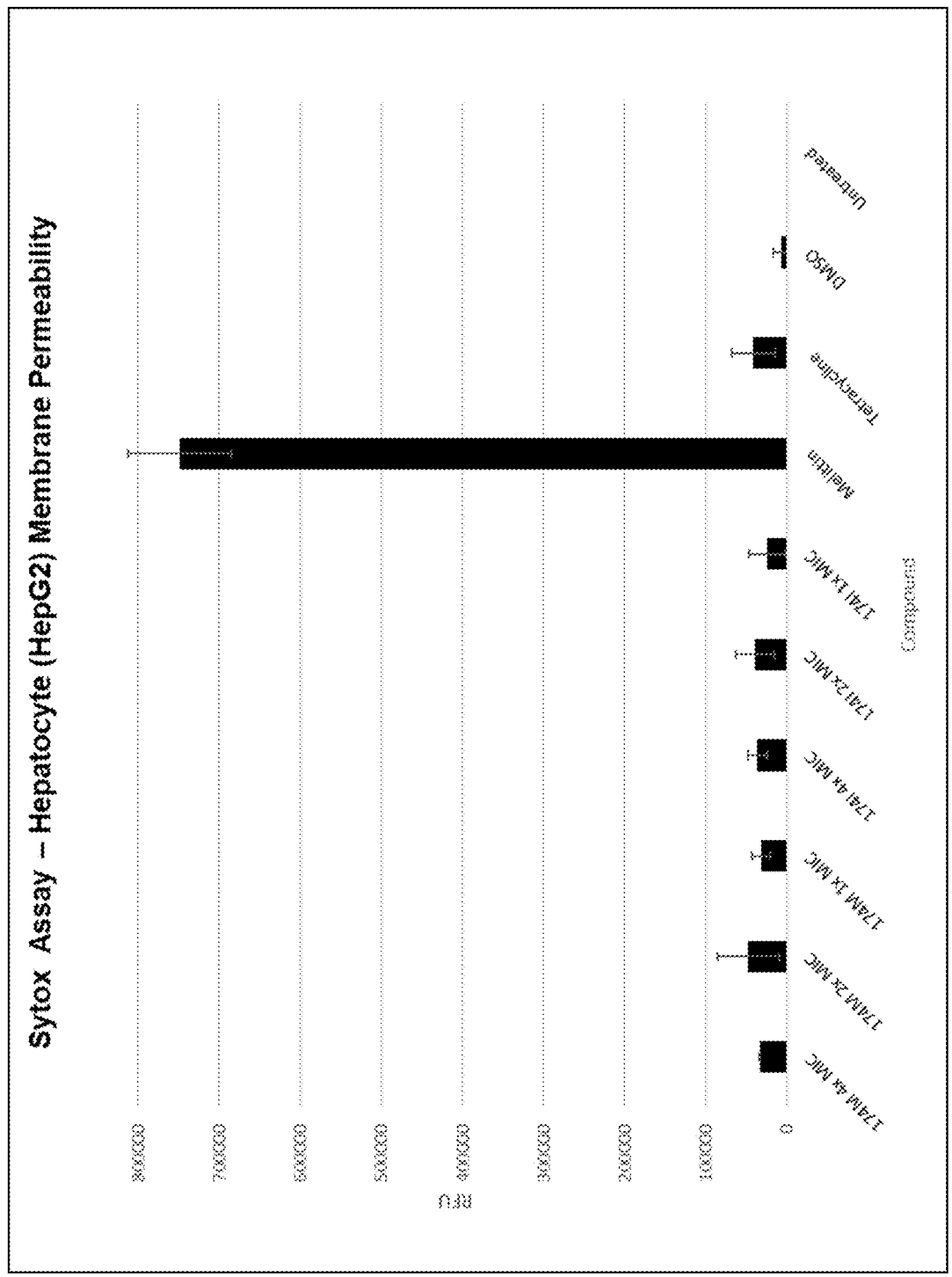
FIG. 2C includes a graph that shows the membrane permeability for Compound 174I and 174M by factors of MIC concentrations versus controls.

FIG. 2C shows the SYTOX assay indicates no permeabilization of HepG2 cells by up to 4×MIC of analogues 174I and 174M. Additionally, data with HepG2 cells also indicates no cell membrane damage by the analogues by minimal staining in treated cells.

Figure 3:
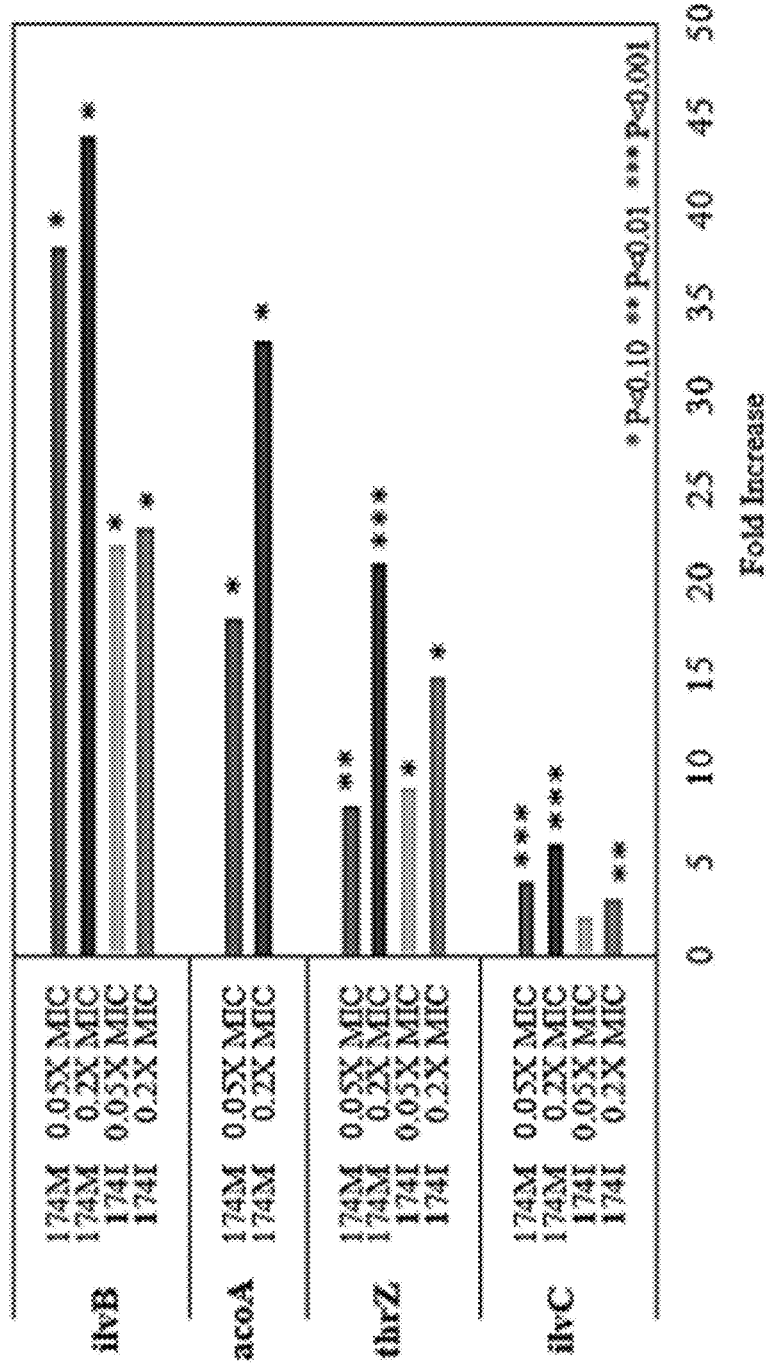
FIG. 3 includes a graph that shows the top upregulated genes by 174I and 174M.

FIG. 3 shows a dose-dependent upregulation RNAseq data expressed in fold increase based on RNA sequencing experiments. The increase in these genes' expression suggests that when these analogues are given to the cells, a pathway is triggered which causes increased transcription of these genes. It could be that the compounds are inhibiting this pathway by binding a protein in the pathway and a feedback mechanism detects reduced pathway products or build-up of intermediates leading to increased expression to combat these effects. The branched chain amino acid synthesis pathway gene, ILVB is highly upregulated. ILVB's inhibition causes a build-up of 2-ketobutyrate which can be toxic at very high concentrations. We demonstrated a synergy between 174M and 2-ketobutyrate as shown in FIG. 3.

Figure 5A:
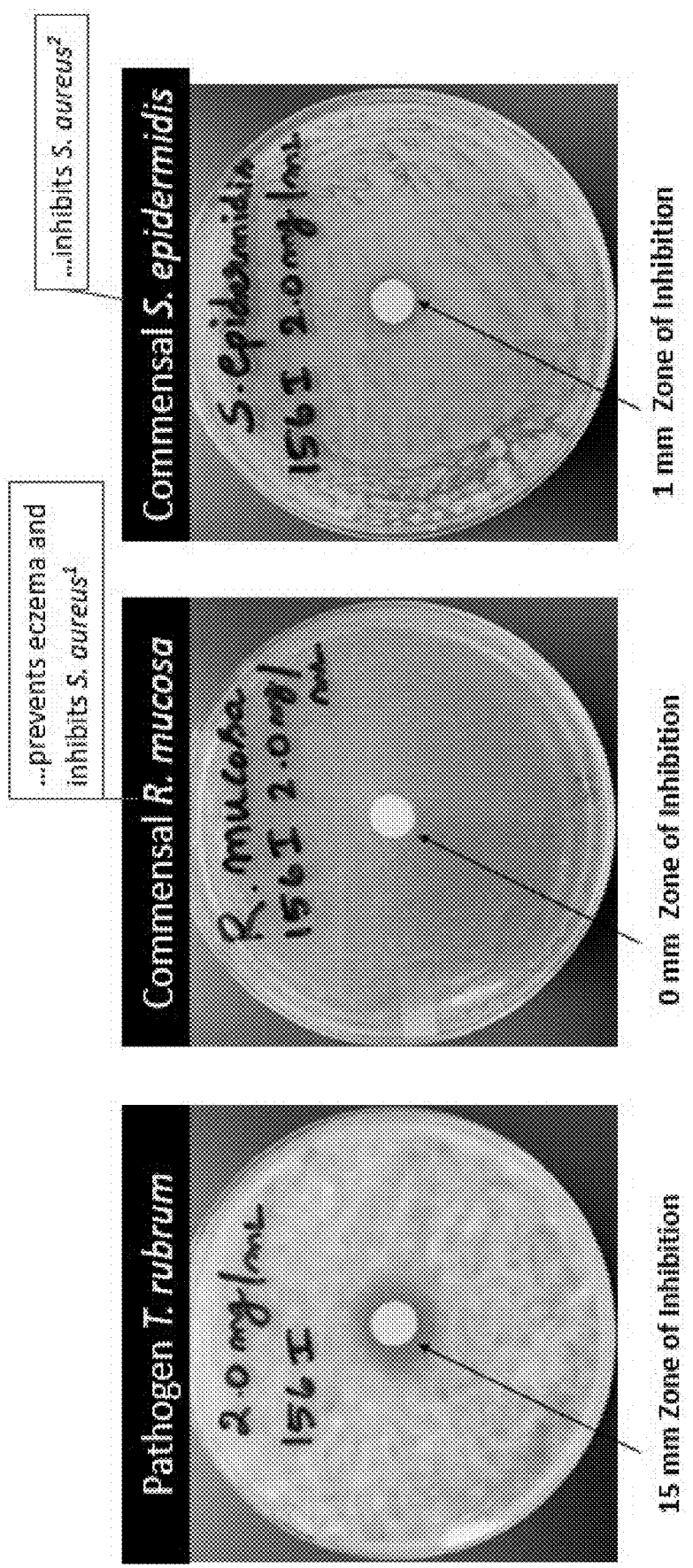
FIGS. 5A-5B show that selective antimicrobials selectively inhibit pathogenic microbes over commensal microbes.
Figure 5B:
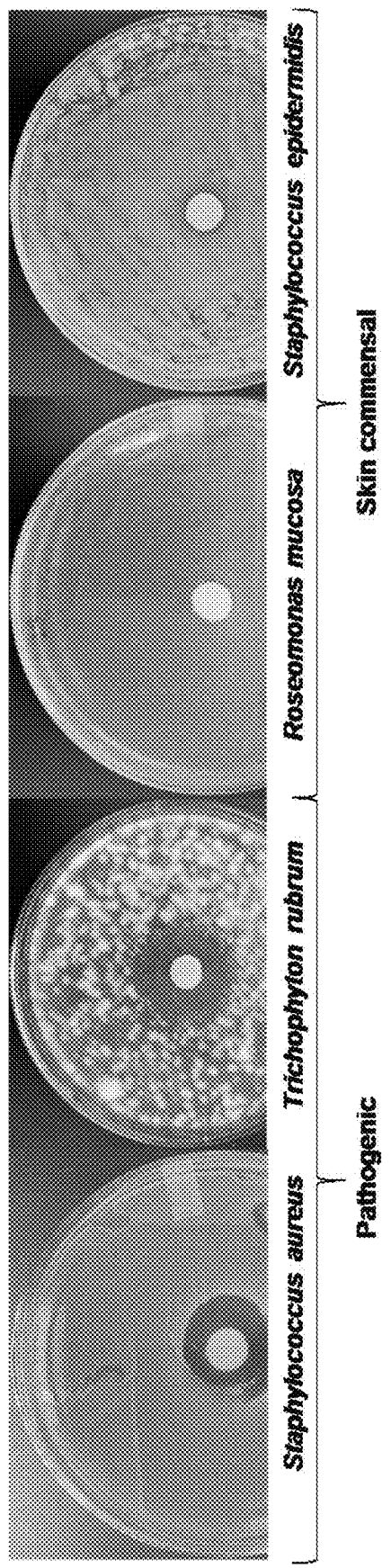

FIGS. 5A-5B show selectivity for inhibiting pathogenic microbes over commensal microbes on polyester fabric. FIG. 5A shows that Compound 156I selectively inhibits pathogens *T. rubrum* over commensal microbes *R. mucosa* and *S. epidermidis*. FIG. 5B shows that Compound 156K inhibits the pathogens *T. rubrum* and *S. Aureus* over commensal microbes *R. mucosa* and *S. epidermidis*

Additionally, an experiment was performed to determine synergistic effect of the compounds with 2-ketobutyrate compared to those of tetracycline with 2-ketobutyrate. Without ketobutyrate, the MIC of Compound 174M is 3.124 µg/mL and the MIC of tetracycline is 6.25. With 200 µg/mL 2-ketobutyrate, the MIC of 174M dropped to 0.781 and with 800 µg/mL 2-ketobutyrate, the MIC of 174M dropped to less than 0.39. However, the MIC for tetracycline did not change with either concentration of 2-ketobutyrate. Thus, at least Compound 174M provides a synergistic effect with 2-ketobutyrate. It is expected that the other compounds, especially those similar to Compound 174M, also can have a synergistic effect with 2-ketobutyrate.

Definitions

As used herein, the term "infection" is encompassed by the term "colonization" and includes disease associated colonization and/or undesirable colonization.

In some embodiments the treatment, mitigation, or prevention for Parkinson's disease in a subject in need thereof comprises physical removal or reduction (e.g. debridement) of the microbial infection.

The term "administered," "administering" or "administration" includes routes of administration which allow the antimicrobial agents to perform their intended function(s) of preventing, mitigating, or treating disease in a subject. Examples of routes of administration include parenteral (e.g., subcutaneous, intramuscular, intraorbital, intracapsular, intraspinal, intrastemal, intravenous, intradermal, intraperitoneal, intraportal, intra-arterial, intrathecal, transmucosal, intra-articular, and intrapleural,), transdermal, topical, epidural, and mucosal injection or infusion, as well as oral, intranasal, inhalation, insufflation, pulmonary, and rectal administration Examples of preferred routes of administration which may be used include injection, topical, oral, intranasal, subcutaneous, intravenous, inhalation and transdermal.

In some embodiments, the antimicrobial agent is administered in combination with a pharmaceutically acceptable carrier. Examples of such carriers include those suitable for injection, topical, oral, intranasal, subcutaneous, intravenous, inhalation and/or transdermal administration.

When used herein, the term "therapeutically effective amount" or "effective amount" includes an amount of the therapeutic or treatment composition that provides a prophylactic or therapeutic benefit in the treatment, prevention, or management of a disease or a symptom of a disease. The therapeutically effective amount may treat a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease. The term "therapeutically effective amount" or "effective amount" of the antimicrobial agent includes an amount of the antimicrobial agent that is sufficient in treating, mitigating, or preventing a microbial infection, such as jock itch or athlete's foot or other.

The dosage ranges for the administration are those that produce the desired effect. Generally, the dosage will vary with the age, weight, condition, and sex of the patient, and the extent of disease. A person of ordinary skill in the art, given the teachings of the present specification, may readily determine suitable dosage ranges.

As used herein, the term "antimicrobial agent" is any substance that has a significant biocidal and/or biostatic activity against a fungus for use in the treatment, mitigation, or prevention of disease. In some embodiments, the antimicrobial agent inhibits the growth of one or more microbial organisms in a subject receiving said agent. In some embodiments, the antimicrobial agent kills one or more microorganisms in a subject receiving said agent.

In some embodiments, the antimicrobial agent is a substance that has a biocidal and/or biostatic activity for microbes. In further embodiments, the antimicrobial agent is a substance that has a biocidal and/or biostatic activity that is relatively specific and selective for pathogenic microbes over commensal microbes.

By "substituted" as in "substituted alkyl," "substituted aryl," and the like, as alluded to in some of the definitions provided herein, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, heteroatom-containing alkenyl, and heteroatom-containing aryl."

As used herein, "optionally substituted" indicates that a chemical structure may be optionally substituted with a substituent group, such as defined herein. That is, when a chemical structure includes an atom that is optionally substituted, the atom may or may not include the optional substituent group, and thereby the chemical structure may be considered to be substituted when having a substituent on the atom or unsubstituted when omitting a substituent from the atom. A substituted group, referred to as a "substituent" or "substituent group", can be coupled (e.g., covalently) to a previously unsubstituted parent structure, wherein one or more hydrogen atoms (or other substituent groups) on the parent structure have been independently replaced by one or more of the substituents. The substituent is a chemical moiety that is added to a base chemical structure, such as a chemical scaffold. As such, a substituted chemical structure may have one or more substituent groups on the parent structure, such as by each substituent group being coupled to an atom of the parent structure. The substituent groups that can be coupled to the parent structure can be any possible substituent group. In examples of the present technology, the substituent groups (e.g., R groups) can be independently selected from an alkyl, —O-alkyl (e.g. —OCH$_3$, —OC$_2$H$_5$, —OC$_3$H$_7$, —OC$_4$H$_9$, etc.), —S-alkyl (e.g., —SCH$_3$, —SC$_2$H$_5$, —SC$_3$H$_7$, —SC$_4$H$_9$, etc.), —NR'R", —OH, —SH, —CN, —NO$_2$, or a halogen, wherein R' and R" are independently H or an optionally substituted alkyl. Wherever a substituent is described as "optionally substituted," that substituent can also be optionally substituted with the above substituents.

The term amino refers to the overall charged or net uncharged chemical group, where the R group can be a substituent, such as the substituents described herein:

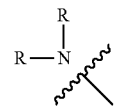

The term "alkyl" or "aliphatic" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, or 1 to about 12 carbon atoms. The term "lower alkyl" intends an alkyl group of 1 to 6 carbon atoms. Substituents identified as "C$_1$-C$_6$ alkyl" or "lower alkyl" contain 1 to 3 carbon atoms, and such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The terms "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, or 2 to 12 carbon atoms. The term "lower alkenyl" intends an alkenyl group of 2 to 6 carbon atoms, and the specific term "cycloalkenyl" intends a cyclic alkenyl group, or having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, or 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein contain 1 to 3 carbon atoms, and such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Examples of aryl groups contain 5 to 20 carbon atoms, and aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Examples of aryloxy groups contain 5 to 20 carbon atoms, and aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Examples of aralkyl groups contain 6 to 24 carbon atoms, and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethyinaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, and fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidine, morpholine, piperazine, piperidine, etc.

The term "hydrocarbyl" refers to univalent hydrocarbyl radicals containing 1 to about 30 carbon atoms, or 1 to about 24 carbon atoms, or 1 to about 18 carbon atoms, or about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

The atoms recited herein include their isotopes. For example, the term "hydrogen" specifically includes the isotopes thereof, such as deuterium. Thus, deuteration of the compounds is contemplated.

All other chemistry terms are defined as known in the art.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

Tables:

TABLE 1

Selectivity of CFD-174M, CFD-156I and CFD-156K against pathogens and skin commensals

| Compounds | Pathogens MIC µg/mL | | Skin Commensals-MIC µg/mL | | Selectivity | Cytotoxicity | |
| --- | --- | --- | --- | --- | --- | --- | --- |
| | *Staphylococcus aureus* (SA) | *Trichophyton rubrum* (TR) | *Roseomonas mucosa* (RM) | *Staphylococcus epidermidis* (SE) | Pathogens to commensal | HepaRG EC50 µg/mL | Selectivity Index (SI) |
| CFD-174M | 2.0 | 0.9 | >50 | 16 | 80->55.5 | 85 | 43->85 |
| CFD-156K | 3.1 | 0.9 | >50 | >50 | 16->55.5 | 32 | 10->32 |
| CFD-156I | | 16 | >64 | >64 | >4 | >20 | >1 |

TABLE #2

| Comp. No. (μg/mL) | *Bacillus subtilis* (Ehrenberg 1835) Cohn 1872 NRRL: B-571 MIC | MBC | *Bacillus thuringiensis* Berliner ATCC: 10792 MIC | MBC | *Burkholderia cenocepacia* NRRL: B-59561 MIC | MBC | *Burkholderia thailandensis* Brett et al ATCC: 700388 MIC | MBC | *Candida glabrata* #584 MIC | MFC | *Trichophyton rubrum* CastellaniSabouraud ATCC: 28188 MIC | *Francisella tularensis* subsp. *Holarctica* Strain LVSR NR-597 MIC |
|---|---|---|---|---|---|---|---|---|---|---|---|---|
| 156I | 20 | 40 | 20 | 40 | 50 | 150 | 50 | 100 | 50 | — | 12.05 | 20 |
| 156O | 6.25 | 12.5 | 6.25 | >50 | >50 | — | — | — | 50 | — | 3.19 | 3.13 |
| 156P | 12.5 | >50 | 3.13 | >50 | >50 | — | — | — | >50 | — | 6.11 | >50 |
| 172A | 1.56 | >50 | 1.56 | 1.56 | >50 | — | >50 | — | 1.56 | 3.13 | 9.52 | 0.78 |
| 172B | 6.25 | 25 | 6.25 | 25 | >50 | — | — | — | 50 | — | 15.6 | 3.13 |
| 172C | 1.56 | 6.25 | 1.56 | 1.56 | >50 | — | >50 | — | 3.13 | >50 | 1.98 | 1.56 |
| 172D | 1.25 | 5 | 1.25 | 10 | 100 | >150 | 100 | >150 | >50 | — | 1.18 | 1.25 |
| 172E | 1.56 | 6.25 | 1.56 | 12.5 | >50 | — | >50 | — | 6.25 | >50 | 2.08 | 0.78 |
| 172G | 11.3 | 45 | 11.3 | >45 | >45 | — | — | — | >50 | — | 18.1 | — |
| 172I | 10 | 10 | 10 | 40 | >40 | — | — | — | >40 | — | 9.92 | 20 |
| 172J | 3.13 | 6.25 | 1.56 | 3.13 | >50 | — | >50 | — | >50 | — | 10.3 | 6.25 |
| 174A | 3.13 | 6.25 | 3.13 | 3.13 | >50 | — | >50 | — | 12.5 | — | — | 1.56 |
| 174AA | 4 | 16 | 8 | 16 | >50 | — | >50 | — | 3.13 | 6.25 | — | 4 |
| 174AB | 4 | 16 | 2 | 8 | >50 | — | >50 | — | 3.13 | — | — | 4 |
| 174AC | 8 | 16 | 8 | 50 | >50 | — | >50 | — | 25 | — | — | — |
| 174AD | 16 | 50 | 32 | >50 | >50 | — | >50 | — | >50 | — | — | — |
| 174AE | 2 | 4 | 2 | >50 | >50 | — | >50 | — | 25 | — | — | 4 |
| 174AF | 4 | 50 | 2 | 4 | >50 | — | >50 | — | >50 | — | — | 4 |
| 174AG | 4 | >50 | 4 | >50 | >50 | — | >50 | — | 6.25 | >50 | — | — |
| 174AH | 8 | >50 | 8 | >50 | >50 | — | >50 | — | >50 | — | — | — |
| 174AI | 0.78 | 6.25 | 0.78 | >50 | 12.5 | >50 | 12.5 | >50 | 6.25 | 25 | — | 2 |
| 174AJ | 0.78 | 3.13 | 0.78 | 1.56 | >50 | — | >50 | — | 6.25 | 25 | — | — |
| 174AK | 50 | >50 | >50 | N/A | >50 | — | >50 | — | >50 | — | — | — |
| 174AL | 0.78 | 1.56 | 1.56 | >50 | >50 | — | >50 | — | 6.25 | 25 | — | — |
| 174AN | 16 | — | — | — | — | — | — | — | 50 | — | — | — |
| 174AO | 50 | — | — | — | — | — | — | — | >50 | — | — | 50 |
| 174AP | 50 | — | — | — | — | — | — | — | >50 | — | — | 50 |
| 174AQ | 32 | — | — | — | — | — | — | — | 50 | — | — | 16 |
| 174AR | 8 | — | — | — | — | — | — | — | 50 | — | — | 4 |
| 174AS | 2 | — | — | — | — | — | — | — | >50 | — | — | 1 |
| 174AT | 8 | 16 | 8 | 16 | — | — | — | — | 50 | — | — | 8 |
| 174AU | 1 | 2 | 1 | 2 | — | — | — | — | 3.13 | 50 | — | 0.25 |
| 174AV | 1 | 2 | 1 | 1 | — | — | — | — | 25 | — | — | 1 |
| 174AX | 0.5 | 8 | 1 | 2 | — | — | — | — | 12.5 | — | — | 1 |
| 174AY | 1 | 2 | 2 | 4 | — | — | — | — | — | — | — | 1 |
| 174AZ | 1 | 4 | 1 | 8 | — | — | — | — | >50 | — | — | 1 |
| 174C | 1.56 | 3.13 | 1.56 | 1.56 | >50 | — | >50 | — | 3.13 | — | 2.11 | 1.56 |
| 174D | 1.56 | 3.13 | 1.56 | 3.13 | >50 | — | >50 | — | 3.13 | — | 2.38 | 1.56 |
| 174E | 1.56 | 3.13 | 1.56 | 3.13 | >50 | — | >50 | — | 3.13 | — | 2.01 | 0.78 |
| 174G | 1.56 | 50 | 1.56 | 3.13 | >50 | — | >50 | — | >50 | — | 2.21 | — |
| 174H | 3.13 | >50 | 6.25 | 12.5 | >50 | — | >50 | — | 12.5 | — | 2.38 | 3.13 |
| 174I | 0.78 | 3.13 | 0.78 | 1.56 | >50 | — | >50 | — | 3.13 | >50 | 1.19 | <0.39 |
| 174J | 1.56 | 3.13 | 1.56 | 1.56 | >50 | — | >50 | — | 6.25 | >50 | 1.05 | — |
| 174K | 3.13 | 6.25 | 3.13 | 6.25 | >50 | — | >50 | — | 6.25 | 12.5 | 1.98 | — |
| 174L | 1.56 | >50 | 1.56 | 50 | >50 | — | >50 | — | >50 | — | >18 | — |
| 174M | 0.63 | 10 | 1.25 | 5 | 150 | >150 | 150 | >150 | 12.5 | — | 0.99 | 2.5 |
| 174N | 1.25 | 10 | 1.25 | 10 | 50 | >150 | 50 | >150 | 6.25 | 50 | <0.57 | 1.25 |
| 174O | 3.13 | >50 | 3.13 | 3.13 | >50 | — | >50 | — | >50 | — | 1.24 | — |
| 174P | 1.56 | 3.13 | 1.56 | >50 | >50 | — | >50 | — | 3.13 | >50 | 2.01 | — |
| 174Q | 1.56 | >50 | 1.56 | 12.5 | >50 | — | >50 | — | 3.13 | >50 | 2.08 | — |
| 174R | >50 | N/A | >50 | N/A | >50 | — | >50 | — | >50 | — | >9.50 | — |
| 174S | >50 | N/A | >50 | N/A | >50 | — | >50 | — | >50 | — | >8.82 | — |
| 174T | 1.25 | >10 | 1.25 | 2.5 | >50 | — | >50 | — | 3.13 | 25 | 1.16 | — |
| 174U | >50 | >10 | 12.5 | 12.5 | >50 | — | >50 | — | >50 | — | 0.95 | 1.56 |
| 174V | 1.25 | 2.5 | 1.25 | 2.5 | >50 | — | >50 | — | 3.13 | 12.5 | 0.58 | — |
| 174W | 1.25 | >10 | 1.25 | 5 | >50 | — | >50 | — | 25 | — | 1.16 | — |
| 174X | 1.56 | >10 | 2.5 | 2.5 | >50 | — | >50 | — | 6.25 | 6.25 | 0.62 | — |
| 174Y | 10 | >10 | 10 | >10 | >50 | — | >50 | — | 25 | — | 3.97 | — |
| 174Z | 10 | >10 | 10 | >10 | >50 | — | >50 | — | 25 | — | 3.97 | — |
| 177A | 0.39 | — | — | — | 25 | >50 | >50 | >50 | >50 | — | — | 0.78 |
| 177B | 1.56 | — | — | — | 25 | >50 | 25 | >50 | >50 | — | — | 3.13 |
| 177C | 0.39 | — | — | — | >50 | >50 | >50 | >50 | >50 | — | — | 3.13 |
| 177D | 1.56 | — | — | — | 12.5 | >50 | >50 | >50 | 25 | — | — | 0.78 |
| 177E | 1.56 | — | — | — | >50 | >50 | >50 | >50 | 25 | — | — | 0.78 |
| 177F | 1.56 | — | — | — | 6.25 | >50 | >50 | >50 | 50 | — | — | 1.56 |
| 177G | 1.56 | — | — | — | >50 | >50 | >50 | >50 | >50 | — | — | 0.78 |
| 177H | 1.56 | — | — | — | 25 | >50 | >50 | >50 | 50 | — | — | 3.13 |
| 177I | 3.13 | — | — | — | >50 | >50 | >50 | >50 | >50 | — | — | 3.13 |

*MBC = Minimum bactericidal concentration,
MFC = Minimum fungicidal concentration

TABLE 3

Staphylococcus aureus MIC

| Comp. No. | VSSA* | VRSA* | MRSA* strains | | | | | | | |
|---|---|---|---|---|---|---|---|---|---|---|
| (µg/mL) | NR-49121 | NR-49120 | NK-41886 | HM-467 | NR-13533 | NR-28983 | NR-41875 | NR-41876 | NR-41877 | NR-41878 |
| 172D | 1.56 | 1.56 | 1.56 | 12.5 | 1.56 | 1.56 | 3.13 | 1.56 | 3.13 | 1.56 |
| 174M | 12.5 | 12.5 | 12.5 | 12.5 | 12.5 | 12.5 | 12.5 | 12.5 | 25 | 12.5 |
| 174N | 1.56 | 3.13 | 3.13 | 3.13 | 3.13 | 3.13 | 3.13 | 3.13 | 3.13 | 3.13 |
| 174AI | 8 | 8 | 8 | 16 | 8 | 8 | 8 | 8 | 8 | 8 |
| 174AT | 16 | 16 | 16 | 32 | 16 | 16 | 16 | 16 | 16 | 16 |
| 174AU | 4 | 2 | 2 | 2 | 2 | 2 | 2 | 2 | 4 | 2 |
| 174AV | 2 | 2 | 2 | 2 | 1 | 1 | 1 | 2 | 2 | 2 |
| 174AX | 1 | 1 | 2 | 2 | 1 | 2 | 1 | 2 | 2 | 1 |
| 174AY | 2 | 2 | 4 | 4 | 4 | 4 | 4 | 2 | 2 | 2 |
| 174AZ | 2 | 2 | — | — | — | — | 4 | 2 | — | — |

*VSSA—Vancomycin sensitive *S. aureus*,
VRSA—Vancomycin resistant *S. aureus*,
MRSA—Methicillin resistant *S. aureus*

TABLE 4

Bacillus subtilis MIC

| Comp. | B. subtilis strains | | | | | | |
|---|---|---|---|---|---|---|---|
| (µg/mL) | BD-594 | B-14322 | B-41090 | B-41581 | B-3665 | B-1985 | B-571 |
| 174AB | 4 | 2 | 4 | 2 | 2 | 4 | — |
| 156K | >50 | >50 | >50 | 3.13 | >50 | >50 | >50 |
| 174M | 5 | 2.5 | 5 | 5 | 10 | 5 | 0.625 |
| 174N | 2.5 | 1.25 | 2.5 | 0.625 | 1.25 | 1.25 | 1.25 |
| 174I | 3.13 | 3.13 | 3.13 | 3.13 | 3.13 | 3.13 | 3.13 |
| 174AI | 6.25 | 3.13 | 6.25 | 6.25 | 6.25 | 0.78 | 0.78 |
| 172D | 2.5 | 1.25 | 2.5 | 1.25 | 1.25 | 1.25 | 1.25 |

TABLE 5

Bacillus thuringiensis MIC

| Comp. | B. thuringiensis strains | | | | | |
|---|---|---|---|---|---|---|
| (µg/mL) | B-23149 | B-23133 | B-41596 | HD-268 | HD-34 | ATCC 10792 |
| 174AB | 2 | 2 | 4 | 4 | 4 | — |
| 156K | >50 | >50 | >50 | >50 | >50 | — |
| 174M | 1.25 | 0.625 | 1.25 | 1.25 | 2.5 | 0.625 |
| 174N | 2.5 | 1.25 | 2.5 | 2.5 | 1.25 | 1.25 |
| 174I | 1.56 | 1.56 | 1.56 | 1.56 | 1.56 | 1.56 |
| 174AI | 1.56 | 0.78 | 0.78 | 2.56 | 1.56 | 0.78 |
| 172D | 5 | 1.25 | 2.5 | 2.5 | 2.5 | 1.25 |

TABLE 6

N. gonorrhoeae MIC

| Comp. | N. gonorrhoeae strains | | |
|---|---|---|---|
| (µg/mL) | #167 | #203 | #205 |
| 174I | 1.56 | — | — |
| 174AI | <0.39 | — | — |
| 172E | <0.39 | 3.13 | 3.13 |
| 174AV | 3.125 | — | — |
| 174AZ | 3.125 | — | — |
| 174E | <0.39 | 1.56 | 1.56 |
| 174N | 1.56 | — | — |
| 174M | 1.56 | — | — |
| 177A | — | 3.13 | 3.13 |
| 177C | — | 3.13 | 3.13 |

TABLE 7

| Candida sp. MIC's | | | | | | | | |
|---|---|---|---|---|---|---|---|---|
| | *C. glabrata* strains | | | | *C. albicans* strains | | | |
| Comp. | #584 | | #325 | | #761 | | #762 | |
| (μg/mL) | MIC | MFC | MIC | MFC | MIC | MFC | MIC | MFC |
| 156I | 50 | >50 | >50 | — | >50 | — | 50 | >50 |
| 172A | 156 | 3.13 | 6.25 | 12.5 | 3.13 | 12.5 | 1.56 | 6.25 |
| 174AB | 3.13 | — | >50 | — | >50 | — | >50 | — |
| 174AE | 25 | — | 12.5 | >50 | 50 | >50 | 6.25 | 25 |
| 174AX | 12.5 | — | >50 | — | 12.5 | 50 | 6.25 | 12.5 |
| 174D | 3.13 | — | >50 | — | >50 | — | 3.13 | 12.5 |
| 174I | 3.13 | >50 | 25 | 50 | 12.5 | 25 | 3.13 | 6.25 |
| 174M | 12.5 | — | 25 | >50 | 12.5 | 25 | 3.13 | 25 |
| 174N | 6.25 | 50 | >50 | — | 12.5 | >50 | 3.13 | 6.25 |
| 174W | 25 | — | >50 | — | >50 | — | >50 | — |
| 174X | 6.25 | 6.25 | 12.5 | >50 | 12.5 | >50 | 12.5 | >50 |

MFC = Minimum fungicidal concentration

TABLE 8

| *F. tularensis* BSL-3 MIC | | | | | | | | | | | | | |
|---|---|---|---|---|---|---|---|---|---|---|---|---|---|
| | *Francisella tularensis* strains | | | | | | | | | | | | |
| Comp. (μg/mL) | SCHU S4 | LVS | MA00-2987 | MO #1 | MO #2 | MO #3 | WY-96 | Strain 100 | OR-96 | HN-63 | MIC50 | MIN | MAX |
| 172E | 4 | >8 | 8 | 5.33 | 3.33 | 8 | >8 | >8 | 8 | 8 | 8 | 3.33 | >8 |
| 174AI | 4 | 4 | 1.67 | 1.33 | 1.33 | 2 | 6 | 6 | 4 | 2 | 3 | 1.33 | 6 |
| 174AU | 4 | 2 | 2 | 1.83 | 1.67 | 2 | 1.5 | 8 | 4 | 2 | 2 | 1.5 | 8 |
| 174AV | 4 | 4 | 3.67 | 3 | 2 | 4 | 4 | 6 | 4 | 4 | 4 | 2 | 6 |
| 174X | 4 | >8 | 4 | 2.67 | 2 | 4 | 3 | 8 | 4 | 4 | 4 | 2 | >8 |
| 174AY | 4 | 4 | 3.67 | 2 | 3.33 | 3.67 | 4 | 4 | 4 | 2 | 3.83 | 2 | 4 |
| 174AZ | 4 | 2.67 | 2 | 1.33 | 1 | 2 | 2 | 4 | 2 | 2 | 2 | 1 | 4 |
| 174I | 8 | 2 | 1.33 | 2 | 1 | 2 | 2 | 8 | 4 | 4 | 2 | 1 | 8 |
| 174M | 8 | 2 | 2 | 2 | 1.67 | 4 | 4 | >8 | 4 | 4 | 4 | 1.67 | >8 |
| 174N | >8 | 6.67 | 6.67 | 3.33 | 3.67 | 4 | 4 | 8 | 4 | 4 | 4 | 3.33 | >8 |

TABLE 9

| Compound | EC50 | SI |
|---|---|---|
| 174C | 25.4 | 16.3 |
| 174D | 23.2 | 14.9 |
| 174E | 23.6 | 14.2 |
| 174P | 38.3 | 24.6 |
| 174V | 24.8 | 19.8 |
| 172C | 26.8 | 17.2 |
| 174AL | 26.1 | 33.5 |
| 174AI | 27.4 | 35.1 |
| 174AU | 26.8 | 26.8 |
| 174AZ | 25.8 | 25.7 |
| 174X | 30.2 | 19.3 |
| 174J | 25.3 | 16.2 |
| 177A | 24.1 | 61.8 |
| 177B | 27.7 | 17.8 |

TABLE 9-continued

| Compound | EC50 | SI |
|---|---|---|
| 177C | 48.2 | 123.6 |
| 177D | 27.1 | 17.4 |
| 177E | 31.6 | 20.3 |
| 177F | 29.8 | 19.1 |
| 177G | 29.5 | 18.9 |
| 177H | 31.8 | 20.4 |
| 177I | 31.3 | 10.0 |
| 156K | 27.6 | ⁻0.6 |
| 174I | 25.4 | 32.6 |
| 174M | 26.5 | 42.4 |
| 174N | 29.5 | 23.6 |
| 172E | 23.3 | 14.9 |
| 156I | 12.1 | 0.6 |

TABLE 10

| Group # | Test Article | Dosing Route | Total Animals N= | Dose mg/kg[1] | Dosing Solution Conc. ug/mL[1] | Dosing Volume mL/kg |
|---|---|---|---|---|---|---|
| 1 | Compound 1 | IP | 3 | 0.1 | 6.8 | 15 |
| 2 | | IP | 3 | 1 | 68 | 15 |
| 3 | | IP | 3 | 10 | 680 | 15 |
| 4 | Compound 2 | IP | 3 | 0.1 | 6.8 | 15 |
| 5 | | IP | 3 | 1 | 68 | 15 |
| 6 | | IP | 3 | 10 | 680 | 15 |

TABLE 10-continued

| Group # | Test Article | Dosing Route | Total Animals N= | Dose mg/kg[1] | Dosing Solution Conc. ug/mL[1] | Dosing Volume mL/kg |
|---|---|---|---|---|---|---|
| 7 | Compound 3 | IP | 3 | 0.1 | 6.8 | 15 |
| 8 | | IP | 3 | 1 | 68 | 15 |
| 9 | | IP | 3 | 10 | 680 | 15 |
| 10 | Vehicle Control | IP | 3 | NA | NA | 15 |

TABLE 11

| | | Animal body weight (kg) | | | | | | | |
|---|---|---|---|---|---|---|---|---|---|
| Group # | Animal # | Day 0 | Day 1 | Day 2 | Day 3 | Day 4 | Day 5 | Day 6 | Day 7 |
| Group 1 | 99 | 0.026 | 0.024 | 0.025 | 0.025 | 0.025 | 0.025 | 0.025 | 0.024 |
| | 100 | 0.023 | 0.022 | 0.022 | 0.022 | 0.022 | 0.023 | 0.022 | 0.022 |
| | 101 | 0.024 | 0.023 | 0.023 | 0.023 | 0.023 | 0.024 | 0.023 | 0.023 |
| Group 2 | 102 | 0.022 | 0.022 | 0.022 | 0.022 | 0.023 | 0.023 | 0.023 | 0.024 |
| | 103 | 0.025 | 0.025 | 0.025 | 0.025 | 0.025 | 0.025 | 0.025 | 0.025 |
| | 104 | 0.026 | 0.025 | 0.026 | 0.026 | 0.026 | 0.026 | 0.025 | 0.026 |
| Group 3 | 105 | 0.024 | 0.023 | 0.023 | 0.024 | 0.023 | 0.023 | 0.022 | 0.022 |
| | 106 | 0.024 | 0.023 | 0.023 | 0.023 | 0.023 | 0.023 | 0.023 | 0.023 |
| | 107 | 0.025 | 0.024 | 0.025 | 0.025 | 0.025 | 0.026 | 0.026 | 0.026 |
| Group 4 | 108 | 0.023 | 0.022 | 0.022 | 0.022 | 0.023 | 0.022 | 0.022 | 0.022 |
| | 109 | 0.025 | 0.024 | 0.025 | 0.025 | 0.025 | 0.025 | 0.025 | 0.025 |
| | 110 | 0.023 | 0.023 | 0.023 | 0.023 | 0.023 | 0.023 | 0.023 | 0.022 |
| Group 5 | 111 | 0.024 | 0.023 | 0.024 | 0.025 | 0.025 | 0.025 | 0.025 | 0.025 |
| | 112 | 0.024 | 0.024 | 0.024 | 0.024 | 0.024 | 0.023 | 0.024 | 0.023 |
| | 113 | 0.025 | 0.024 | 0.024 | 0.024 | 0.025 | 0.024 | 0.024 | 0.024 |
| Group 6 | 114 | 0.023 | 0.022 | 0.022 | 0.022 | 0.023 | 0.023 | 0.022 | 0.023 |
| | 115 | 0.024 | 0.023 | 0.023 | 0.022 | 0.023 | 0.023 | 0.023 | 0.023 |
| | 116 | 0.023 | 0.022 | 0.023 | 0.023 | 0.023 | 0.023 | 0.022 | 0.022 |
| Group 7 | 117 | 0.023 | 0.022 | 0.023 | 0.024 | 0.024 | 0.024 | 0.024 | 0.023 |
| | 118 | 0.023 | 0.022 | 0.022 | 0.022 | 0.022 | 0.022 | 0.022 | 0.022 |
| | 119 | 0.022 | 0.021 | 0.021 | 0.022 | 0.022 | 0.022 | 0.022 | 0.023 |
| Group 8 | 120 | 0.022 | 0.023 | 0.023 | 0.023 | 0.022 | 0.022 | 0.022 | 0.022 |
| | 121 | 0.024 | 0.024 | 0.025 | 0.025 | 0.025 | 0.025 | 0.024 | 0.024 |
| | 122 | 0.026 | 0.026 | 0.026 | 0.027 | 0.026 | 0.026 | 0.026 | 0.026 |
| Group 9 | 123 | 0.022 | 0.021 | 0.022 | 0.022 | 0.022 | 0.023 | 0.022 | 0.022 |
| | 124 | 0.026 | 0.024 | 0.024 | 0.025 | 0.026 | 0.026 | 0.026 | 0.026 |
| | 125 | 0.024 | 0.022 | 0.023 | 0.023 | 0.024 | 0.024 | 0.024 | 0.023 |
| Group 10 | 126 | 0.024 | 0.023 | 0.023 | 0.023 | 0.023 | 0.024 | 0.024 | 0.024 |
| | 127 | 0.023 | 0.023 | 0.024 | 0.024 | 0.023 | 0.024 | 0.024 | 0.024 |
| | 128 | 0.024 | 0.024 | 0.024 | 0.024 | 0.024 | 0.024 | 0.024 | 0.024 |

The invention claimed is:
1. A compound selected from the group consisting of:
3-((4-bromophenyl)thio)-6-fluoro-1H-indole (172A);
2-((4-bromophenyl)thio)-3-methyl-1H-indole (172B);
methyl 3-((4-bromophenyl)thio)-1H-indole-5-carboxylate (172G);
5-bromo-3-((4-bromophenyl) sulfinyl)-1H-indole (172I);
5-bromo-3-((4-bromophenyl) sulfonyl)-1H-indole (172J);
6-bromo-3-((4-bromophenyl)thio)-1H-indole (174A);
5,6-dibromo-3-((4-bromophenyl)thio)-1H-indole (174AB);
5,7-dibromo-3-((4-bromophenyl)thio)-1H-indole (174AC);
5-bromo-3-((perchlorophenyl)thio)-1H-indole (174AD);
4,6-dibromo-3-((4-bromophenyl)thio)-1H-indole (174AE);
5-bromo-3-((4-bromophenyl)thio)-6-chloro-1H-indole (174AF);
5-bromo-3-((2,4,6-trichlorophenyl)thio)-1H-indole (174AG);
5-bromo-3-((3,4,5-tribromophenyl)thio)-1H-indole (174AH);
2-((5-bromo-1H-indol-3-yl)thio)phenol (174AI);
5-bromo-3-((2-chlorophenyl)thio)-1H-indole (174AJ);
3-((2-aminophenyl)thio)-2-methyl-1H-indol-5-ol (174AK);
3-((1H-indol-3-yl)thio)-5-bromo-1H-indole (174AL);
3-((2-hydroxyphenyl)thio)-2-methyl-1H-indol-5-ol (174AO);
3-((2-hydroxyphenyl)thio)-1H-indol-5-ol (174AP);
2-((5-methoxy-1H-indol-3-yl)thio)phenol (174AQ);
3-((2-bromophenyl)thio)-1H-indol-5-ol (174AR);
3-((2-bromophenyl)thio)-5-methoxy-1H-indole (174AS);
(2-((5-bromo-1H-indol-3-yl)thio)phenyl) methanol (174AT);
5-bromo-3-((2-(fluorophenyl)thio)-1H-indole (174AU);
5-bromo-3-((2-(trifluoromethyl)phenyl)thio)-1H-indole (174AV);
3-((2-bromophenyl)thio)-5-(trifluoromethyl)-1H-indole (174AX);
5-bromo-3-(o-tolylthio)-1H-indole (174AY);
5-bromo-3-((2-bromophenyl)thio)-2-methyl-1H-indole (174AZ);
4-bromo-3-((4-bromophenyl)thio)-1H-indole (174D);

3-((4-bromophenyl)thio)-5-fluoro-1H-indole (174E);
7-bromo-3-((4-bromophenyl)thio)-1H-indole (174H);
5-bromo-3-((3-bromophenyl)thio)-1H-indole (174N);
5-bromo-3-((4-bromobenzyl)thio)-1H-indole (174O);
3-([1,1'-biphenyl]-4-ylthio)-5-bromo-1H-indole (174R);
5-bromo-3-((2,3-dichlorophenyl)thio)-1H-indole (174T);
5-bromo-3-((2,4-dichlorophenyl)thio)-1H-indole (174V);
5-bromo-3-((3,4-dichlorophenyl)thio)-1H-indole (174W);
5-bromo-2-((5-bromo-1H-indol-3-yl)thio)aniline (174X);
3-((5-bromo-1H-indol-3-yl)thio)aniline (174Y);
2-((5-(trifluoromethyl)-1H-indol-3-yl)thio)phenol (177A);
4-((5-(trifluoromethyl)-1H-indol-3-yl)thio)phenol (177B);
2-((5-(trifluoromethyl)-1H-indol-3-yl)thio)aniline (177C);
3-((2-fluorophenyl)thio)-5-(trifluoromethyl)-1H-indole (177D);
3-((2-bromophenyl)thio)-5-fluoro-1H-indole (177E);
5-(trifluoromethyl)-3-((2-(trifluoromethyl)phenyl)thio)-1H-indole (177F);
3-((2-ethylphenyl)thio)-5-(trifluoromethyl)-1H-indole (177G);
(5-bromo-3-((2-bromophenyl)thio)-1H-indol-2-yl) methanol (177H);
(3-((2-ethylphenyl)thio)-5-(trifluoromethyl)-1H-indol-2-yl) methanol (177I);
N-((3-((4-hydroxyphenyl)thio)-1H-indol-5-yl)methyl)-4-(triethoxysilyl) butanamide (156SI); and
3-((2-aminophenyl)thio)-5-bromo-N-(3-(triethoxysilyl) propyl)-1H-indole-2-carboxamide (174SI),
or salts thereof.

2. A composition comprising:
the compound of claim 1; and
a liquid carrier having the compound.

3. An article of manufacture comprising:
the compound of claim 2; and
a solid material having the compound on a surface or body of the solid material.

4. The compound of claim 1, wherein the compound is selected from the group consisting of:
5-bromo-3-(o-tolylthio)-1H-indole (174AY);
3-((4-bromophenyl)thio)-6-fluoro-1H-indole (172A);
2-((4-bromophenyl)thio)-3-methyl-1H-indole (172B);
methyl 3-((4-bromophenyl)thio)-1H-indole-5-carboxylate (172G);
5-bromo-3-((4-bromophenyl) sulfinyl)-1H-indole (172I);
5-bromo-3-((4-bromophenyl) sulfonyl)-1H-indole (172J);
6-bromo-3-((4-bromophenyl)thio)-1H-indole (174A);
5,6-dibromo-3-((4-bromophenyl)thio)-1H-indole (174AB);
5,7-dibromo-3-((4-bromophenyl)thio)-1H-indole (174AC);
5-bromo-3-((perchlorophenyl)thio)-1H-indole (174AD); and
4,6-dibromo-3-((4-bromophenyl)thio)-1H-indole (174AE),
or salts thereof.

5. The compound of claim 1, wherein the compound is selected from the group consisting of:
5-bromo-3-(o-tolylthio)-1H-indole (174AY);
5-bromo-3-((4-bromophenyl)thio)-6-chloro-1H-indole (174AF);
5-bromo-3-((2,4,6-trichlorophenyl)thio)-1H-indole (174AG);
5-bromo-3-((3,4,5-tribromophenyl)thio)-1H-indole (174AH);
2-((5-bromo-1H-indol-3-yl)thio)phenol (174AI);
5-bromo-3-((2-chlorophenyl)thio)-1H-indole (174AJ);
3-((2-aminophenyl)thio)-2-methyl-1H-indol-5-ol (174AK);
3-((1H-indol-3-yl)thio)-5-bromo-1H-indole (174AL);
3-((2-hydroxyphenyl)thio)-2-methyl-1H-indol-5-ol (174AO); and
3-((2-hydroxyphenyl)thio)-1H-indol-5-ol (174AP),
or salts thereof.

6. The compound of claim 1, wherein the compound is selected from the group consisting of:
5-bromo-3-(o-tolylthio)-1H-indole (174AY);
2-((5-methoxy-1H-indol-3-yl)thio)phenol (174AQ);
3-((2-bromophenyl)thio)-1H-indol-5-ol (174AR);
3-((2-bromophenyl)thio)-5-methoxy-1H-indole (174AS);
(2-((5-bromo-1H-indol-3-yl)thio)phenyl) methanol (174AT);
5-bromo-3-((2-fluorophenyl)thio)-1H-indole (174AU);
5-bromo-3-((2-(trifluoromethyl)phenyl)thio)-1H-indole (174AV);
3-((2-bromophenyl)thio)-5-(trifluoromethyl)-1H-indole (174AX);
5-bromo-3-((2-bromophenyl)thio)-2-methyl-1H-indole (174AZ);
4-bromo-3-((4-bromophenyl)thio)-1H-indole (174D); and
3-((4-bromophenyl)thio)-5-fluoro-1H-indole (174E),
or salts thereof.

7. The compound of claim 1, wherein the compound is selected from the group consisting of:
5-bromo-3-(o-tolylthio)-1H-indole (174AY);
7-bromo-3-((4-bromophenyl)thio)-1H-indole (174H);
5-bromo-3-((3-bromophenyl)thio)-1H-indole (174N);
5-bromo-3-((4-bromobenzyl)thio)-1H-indole (174O);
3-([1,1'-biphenyl]-4-ylthio)-5-bromo-1H-indole (174R);
5-bromo-3-((2,3-dichlorophenyl)thio)-1H-indole (174T);
5-bromo-3-((2,4-dichlorophenyl)thio)-1H-indole (174V);
5-bromo-3-((3,4-dichlorophenyl)thio)-1H-indole (174W);
5-bromo-2-((5-bromo-1H-indol-3-yl)thio)aniline (174X); and
3-((5-bromo-1H-indol-3-yl)thio)aniline (174Y),
or salts thereof.

8. The compound of claim 1, wherein the compound is selected from the group consisting of:
5-bromo-3-(o-tolylthio)-1H-indole (174AY);
2-((5-(trifluoromethyl)-1H-indol-3-yl)thio)phenol (177A);
4-((5-(trifluoromethyl)-1H-indol-3-yl)thio)phenol (177B);
2-((5-(trifluoromethyl)-1H-indol-3-yl)thio)aniline (177C);
3-((2-fluorophenyl)thio)-5-(trifluoromethyl)-1H-indole (177D);
3-((2-bromophenyl)thio)-5-fluoro-1H-indole (177E);
5-(trifluoromethyl)-3-((2-(trifluoromethyl)phenyl)thio)-1H-indole (177F);
3-((2-ethylphenyl)thio)-5-(trifluoromethyl)-1H-indole (177G);
(5-bromo-3-((2-bromophenyl)thio)-1H-indol-2-yl) methanol (177H);
(3-((2-ethylphenyl)thio)-5-(trifluoromethyl)-1H-indol-2-yl) methanol (177I);
N-((3-((4-hydroxyphenyl)thio)-1H-indol-5-yl)methyl)-4-(triethoxysilyl) butanamide (156SI); and 3-((2-aminophenyl)thio)-5-bromo-N-(3-(triethoxysilyl) propyl)-1H-indole-2-carboxamide (174SI),
or salts thereof.

9. The compound of claim 1, wherein the compound is selected from the group consisting of:
5-bromo-3-(o-tolylthio)-1H-indole (174AY);
3-((4-bromophenyl)thio)-6-fluoro-1H-indole (172A);
2-((4-bromophenyl)thio)-3-methyl-1H-indole (172B);
methyl 3-((4-bromophenyl)thio)-1H-indole-5-carboxylate (172G);
5-bromo-3-((4-bromophenyl) sulfinyl)-1H-indole (172I); and
5-bromo-3-((4-bromophenyl) sulfonyl)-1H-indole (172J),
or salts thereof.

10. The compound of claim 1, wherein the compound is selected from the group consisting of:
5-bromo-3-(o-tolylthio)-1H-indole (174AY);
6-bromo-3-((4-bromophenyl)thio)-1H-indole (174A);
5,6-dibromo-3-((4-bromophenyl)thio)-1H-indole (174AB);
5,7-dibromo-3-((4-bromophenyl)thio)-1H-indole (174AC);
5-bromo-3-((perchlorophenyl)thio)-1H-indole (174AD); and
4,6-dibromo-3-((4-bromophenyl)thio)-1H-indole (174AE),
or salts thereof.

11. The compound of claim 1, wherein the compound is selected from the group consisting of:
5-bromo-3-(o-tolylthio)-1H-indole (174AY);
5-bromo-3-((4-bromophenyl)thio)-6-chloro-1H-indole (174AF);
5-bromo-3-((2,4,6-trichlorophenyl)thio)-1H-indole (174AG);
5-bromo-3-((3,4,5-tribromophenyl)thio)-1H-indole (174AH);
2-((5-bromo-1H-indol-3-yl)thio)phenol (174AI); and
5-bromo-3-((2-chlorophenyl)thio)-1H-indole (174AJ),
or salts thereof.

12. The compound of claim 1, wherein the compound is selected from the group consisting of:
5-bromo-3-(o-tolylthio)-1H-indole (174AY);
3-((2-aminophenyl)thio)-2-methyl-1H-indol-5-ol (174AK);
3-((1H-indol-3-yl)thio)-5-bromo-1H-indole (174AL);
3-((2-hydroxyphenyl)thio)-2-methyl-1H-indol-5-ol (174AO); and
3-((2-hydroxyphenyl)thio)-1H-indol-5-ol (174AP),
or salts thereof.

13. The compound of claim 1, wherein the compound is selected from the group consisting of:
5-bromo-3-(o-tolylthio)-1H-indole (174AY);
2-((5-methoxy-1H-indol-3-yl)thio)phenol (174AQ);
3-((2-bromophenyl)thio)-1H-indol-5-ol (174AR);
3-((2-bromophenyl)thio)-5-methoxy-1H-indole (174AS);
(2-((5-bromo-1H-indol-3-yl)thio)phenyl) methanol (174AT); and
5-bromo-3-((2-fluorophenyl)thio)-1H-indole (174AU),
or salts thereof.

14. The compound of claim 1, wherein the compound is selected from the group consisting of:
5-bromo-3-(o-tolylthio)-1H-indole (174AY);
5-bromo-3-((2-(trifluoromethyl)phenyl)thio)-1H-indole (174AV);
3-((2-bromophenyl)thio)-5-(trifluoromethyl)-1H-indole (174AX);
5-bromo-3-((2-bromophenyl)thio)-2-methyl-1H-indole (174AZ);
4-bromo-3-((4-bromophenyl)thio)-1H-indole (174D); and
3-((4-bromophenyl)thio)-5-fluoro-1H-indole (174E),
or salts thereof.

15. The compound of claim 1, wherein the compound is selected from the group consisting of:
5-bromo-3-(o-tolylthio)-1H-indole (174AY);
7-bromo-3-((4-bromophenyl)thio)-1H-indole (174H);
5-bromo-3-((3-bromophenyl)thio)-1H-indole (174N);
5-bromo-3-((4-bromobenzyl)thio)-1H-indole (174O); and
3-([1,1'-biphenyl]-4-ylthio)-5-bromo-1H-indole (174R),
or salts thereof.

16. The compound of claim 1, wherein the compound is selected from the group consisting of:
5-bromo-3-(o-tolylthio)-1H-indole (174AY);
5-bromo-3-((2,3-dichlorophenyl)thio)-1H-indole (174T);
5-bromo-3-((2,4-dichlorophenyl)thio)-1H-indole (174V);
5-bromo-3-((3,4-dichlorophenyl)thio)-1H-indole (174W);
5-bromo-2-((5-bromo-1H-indol-3-yl)thio)aniline (174X); and
3-((5-bromo-1H-indol-3-yl)thio)aniline (174Y),
or salts thereof.

17. The compound of claim 1, wherein the compound is selected from the group consisting of:
5-bromo-3-(o-tolylthio)-1H-indole (174AY);
2-((5-(trifluoromethyl)-1H-indol-3-yl)thio)phenol (177A);
4-((5-(trifluoromethyl)-1H-indol-3-yl)thio)phenol (177B);
2-((5-(trifluoromethyl)-1H-indol-3-yl)thio)aniline (177C);
3-((2-fluorophenyl)thio)-5-(trifluoromethyl)-1H-indole (177D); and
3-((2-bromophenyl)thio)-5-fluoro-1H-indole (177E),
or salts thereof.

18. The compound of claim 1, wherein the compound is 5-bromo-3-(o-tolylthio)-1H-indole (174AY);
5-(trifluoromethyl)-3-((2-(trifluoromethyl)phenyl)thio)-1H-indole (177F);
3-((2-ethylphenyl)thio)-5-(trifluoromethyl)-1H-indole (177G);
(5-bromo-3-((2-bromophenyl)thio)-1H-indol-2-yl) methanol (177H);
(3-((2-ethylphenyl)thio)-5-(trifluoromethyl)-1H-indol-2-yl) methanol (177I);
N-((3-((4-hydroxyphenyl)thio)-1H-indol-5-yl)methyl)-4-(triethoxysilyl) butanamide (156SI); and
3-((2-aminophenyl)thio)-5-bromo-N-(3-(triethoxysilyl) propyl)-1H-indole-2-carboxamide (174SI),
or salts thereof.

19. The compound of claim 1, wherein the compound is 5-bromo-3-(o-tolylthio)-1H-indole (174AY), or salts thereof.

20. The compound of claim 1, wherein the compound is selected from the group consisting of:
3-((2-aminophenyl)thio)-2-methyl-1H-indol-5-ol (174AK);
3-((1H-indol-3-yl)thio)-5-bromo-1H-indole (174AL);
3-((2-hydroxyphenyl)thio)-2-methyl-1H-indol-5-ol (174AO);
3-((2-hydroxyphenyl)thio)-1H-indol-5-ol (174AP);
2-((5-methoxy-1H-indol-3-yl)thio)phenol (174AQ);
3-((2-bromophenyl)thio)-1H-indol-5-ol (174AR);
3-((2-bromophenyl)thio)-5-methoxy-1H-indole (174AS);

(2-((5-bromo-1H-indol-3-yl)thio)phenyl) methanol (174AT);
5-bromo-3-((2-(fluorophenyl)thio)-1H-indole (174AU);
5-bromo-3-((2-(trifluoromethyl)phenyl)thio)-1H-indole (174AV);
3-((2-bromophenyl)thio)-5-(trifluoromethyl)-1H-indole (174AX);
5-bromo-3-(o-tolylthio)-1H-indole (174AY);
5-bromo-3-((2-bromophenyl)thio)-2-methyl-1H-indole (174AZ);
4-bromo-3-((4-bromophenyl)thio)-1H-indole (174D); and
3-((4-bromophenyl)thio)-5-fluoro-1H-indole (174E), or salts thereof.

* * * * *